US00RE43282E

(19) United States
(12) Reissued Patent
Alexander et al.

(10) Patent Number: US RE43,282 E
(45) Date of Reissued Patent: Mar. 27, 2012

(54) ASSESSING THE CONDITION OF A JOINT AND DEVISING TREATMENT

(75) Inventors: Eugene J. Alexander, San Clemente, CA (US); Thomas P. Andriacchi, Los Altos Hills, CA (US); Philipp Lang, Lexington, MA (US); Daniel Steines, Palo Alto, CA (US)

(73) Assignee: The Board of Trustees of the Leland Stanford Junior University, Palo Alto, CA (US)

(21) Appl. No.: 12/193,907

(22) Filed: Aug. 19, 2008

Related U.S. Patent Documents

Reissue of:
(64) Patent No.: 7,239,908
Issued: Jul. 3, 2007
Appl. No.: 09/662,224
Filed: Sep. 14, 2000

U.S. Applications:
(63) Continuation-in-part of application No. PCT/US99/30265, filed on Dec. 16, 1999.

(60) Provisional application No. 60/112,989, filed on Dec. 16, 1998.

(51) Int. Cl.
*A61B 5/05* (2006.01)

(52) U.S. Cl. ..... 600/427; 600/407; 600/410; 600/411; 600/425; 600/437; 600/439; 382/128; 382/173; 382/190; 382/258; 378/21; 378/62; 378/63; 378/64; 378/65

(58) Field of Classification Search ..... 600/7, 10, 600/11, 25, 27, 37, 39; 382/128, 173, 190, 382/258; 378/21, 62–65
See application file for complete search history.

(56) References Cited

U.S. PATENT DOCUMENTS

| | | | | |
|---|---|---|---|---|
| 3,314,420 | A | 4/1967 | Smith et al. | 128/92 |
| 3,605,123 | A | 9/1971 | Hahn | 3/1 |
| 3,694,820 | A | 10/1972 | Scales et al. | 3/1 |
| 3,798,679 | A | 3/1974 | Ewald | 3/1 |

(Continued)

FOREIGN PATENT DOCUMENTS

| | | |
|---|---|---|
| CN | 86209787 | 11/1987 |

(Continued)

OTHER PUBLICATIONS

Brandt et al., "Crigos—Entwicklung eines Kompaktrobotersystems für die bildgeführte orthopädische Chirurgie", *Der Orthopäde,* Springer-Verlag, vol. 29, No. 7, pp. 645-649 (Jul. 2000).

(Continued)

*Primary Examiner* — Brian Casler
*Assistant Examiner* — Saurel J Selkin
(74) *Attorney, Agent, or Firm* — Sunstein Kann Murphy & Timbers LLP

(57) ABSTRACT

Methods are disclosed for assessing the condition of a cartilage in a joint, particularly *in* a human knee. The methods include converting an image such as an MRI to a three dimensional map of the cartilage. The cartilage map can be correlated to a movement pattern of the joint to assess the affect of movement on cartilage wear. Changes in the thickness of cartilage over time can be determined so that therapies can be provided. Information on thickness of cartilage and curvature of cartilage or subchondral bone can be used to plan therapy. Information on movement pattern can be used to plan therapy.

140 Claims, 20 Drawing Sheets

U.S. PATENT DOCUMENTS

| | | | | |
|---|---|---|---|---|
| 3,808,606 | A | 5/1974 | Tronzo | 3/1 |
| 3,816,855 | A | 6/1974 | Saleh | 3/1 |
| 3,843,975 | A | 10/1974 | Tronzo | 3/1 |
| 3,852,830 | A | 12/1974 | Marmor | 3/1 |
| 3,855,638 | A | 12/1974 | Pilliar | 3/1 |
| 3,938,198 | A | 2/1976 | Kahn et al. | 3/1.912 |
| 3,987,499 | A | 10/1976 | Scharbach et al. | 3/1.91 |
| 3,991,425 | A | 11/1976 | Martin et al. | 3/1.91 |
| 4,052,753 | A | 10/1977 | Dedo | 3/1 |
| 4,055,862 | A | 11/1977 | Farling | 3/1.91 |
| 4,085,466 | A | 4/1978 | Goodfellow et al. | 3/1.91 |
| 4,098,626 | A | 7/1978 | Graham et al. | 149/19.4 |
| 4,164,793 | A | 8/1979 | Swanson | 3/1.91 |
| 4,178,641 | A | 12/1979 | Grundei et al. | 3/1.911 |
| 4,203,444 | A | 5/1980 | Bonnell et al. | 128/276 |
| 4,213,816 | A | 7/1980 | Morris | 156/245 |
| 4,219,893 | A | 9/1980 | Noiles | 3/1.911 |
| 4,280,231 | A | 7/1981 | Swanson | 3/1.91 |
| 4,309,778 | A | 1/1982 | Buechel et al. | 3/1.911 |
| 4,340,978 | A | 7/1982 | Buechel et al. | 3/1.911 |
| 4,344,193 | A | 8/1982 | Kenny | 3/1.911 |
| 4,364,389 | A | 12/1982 | Keller | 128/303 R |
| 4,368,040 | A | 1/1983 | Weissman | 433/36 |
| 4,436,684 | A | 3/1984 | White | 264/138 |
| 4,459,985 | A | 7/1984 | McKay et al. | 128/303 R |
| 4,501,266 | A | 2/1985 | McDaniel | 128/69 |
| 4,502,161 | A | 3/1985 | Wall | 3/1.91 |
| 4,575,805 | A | 3/1986 | Moermann et al. | 364/474 |
| 4,586,496 | A | 5/1986 | Keller | 128/92 E |
| 4,594,380 | A | 6/1986 | Chapin et al. | 524/144 |
| 4,601,290 | A | 7/1986 | Effron et al. | 128/305 |
| 4,609,551 | A | 9/1986 | Caplan et al. | 424/95 |
| 4,627,853 | A | 12/1986 | Campbell et al. | 623/16 |
| 4,631,676 | A | 12/1986 | Pugh | 364/413 |
| 4,655,227 | A | 4/1987 | Gracovetsky | 128/781 |
| 4,673,409 | A | 6/1987 | Van Kampen | 623/23 |
| 4,699,156 | A | 10/1987 | Gracovetsky | 128/781 |
| 4,714,472 | A | 12/1987 | Averill et al. | 623/20 |
| 4,714,474 | A | 12/1987 | Brooks, Jr. et al. | 623/20 |
| 4,721,104 | A | 1/1988 | Kaufman et al. | 128/92 |
| 4,769,040 | A | 9/1988 | Wevers | 623/20 |
| 4,813,436 | A | 3/1989 | Au | 128/779 |
| 4,822,365 | A | 4/1989 | Walker et al. | 128/898 |
| 4,823,807 | A | 4/1989 | Russell et al. | 128/773 |
| 4,841,975 | A | 6/1989 | Woolson | 128/653 |
| 4,846,835 | A | 7/1989 | Grande | 623/11 |
| 4,865,607 | A | 9/1989 | Witzel et al. | 623/20 |
| 4,872,452 | A | 10/1989 | Alexson | 128/92 |
| 4,880,429 | A | 11/1989 | Stone | 623/18 |
| 4,888,021 | A | 12/1989 | Forte et al. | 623/20 |
| 4,936,862 | A | 6/1990 | Walker et al. | 623/23 |
| 4,944,757 | A | 7/1990 | Martinez et al. | 623/20 |
| 5,002,547 | A | 3/1991 | Poggie et al. | 606/88 |
| 5,021,061 | A | 6/1991 | Wevers et al. | 623/20 |
| 5,041,138 | A | 8/1991 | Vacanti et al. | 623/16 |
| 5,059,216 | A | 10/1991 | Winters | 623/20 |
| 5,067,964 | A | 11/1991 | Richmond et al. | 623/18 |
| 5,099,859 | A | 3/1992 | Bell | 128/781 |
| 5,108,452 | A | 4/1992 | DeMane et al. | 623/23 |
| 5,123,927 | A | 6/1992 | Duncan et al. | 623/20 |
| 5,129,908 | A | 7/1992 | Petersen | 606/88 |
| 5,133,759 | A | 7/1992 | Turner | 623/20 |
| 5,147,365 | A | 9/1992 | Whitlock et al. | 606/88 |
| 5,150,304 | A | 9/1992 | Berchem et al. | 700/182 |
| 5,154,178 | A | 10/1992 | Shah | 128/653.2 |
| 5,154,717 | A | 10/1992 | Matsen, III et al. | 606/53 |
| 5,162,430 | A | 11/1992 | Rhee et al. | 525/54.1 |
| 5,171,322 | A | 12/1992 | Kenny | 623/18 |
| 5,197,985 | A | 3/1993 | Caplan et al. | 623/16 |
| 5,206,023 | A | 4/1993 | Hunziker | 424/423 |
| 5,226,914 | A | 7/1993 | Caplan et al. | 623/16 |
| 5,234,433 | A | 8/1993 | Bert et al. | 606/88 |
| 5,245,282 | A | 9/1993 | Mugler, III et al. | 324/309 |
| 5,246,013 | A | 9/1993 | Frank et al. | 128/774 |
| 5,246,530 | A | 9/1993 | Bugle et al. | 156/643 |
| 5,250,050 | A | 10/1993 | Poggie et al. | 606/79 |
| 5,258,032 | A | 11/1993 | Bertin | 623/20 |
| 5,270,300 | A | 12/1993 | Hunziker | 514/12 |
| 5,274,565 | A | 12/1993 | Reuben | 364/474.24 |
| 5,282,868 | A | 2/1994 | Bahler | 623/20 |
| 5,288,797 | A | 2/1994 | Khalil et al. | 524/872 |
| 5,291,401 | A | 3/1994 | Robinson | 364/413.13 |
| 5,303,148 | A | 4/1994 | Mattson et al. | 364/413.01 |
| 5,306,307 | A | 4/1994 | Senter et al. | 623/17 |
| 5,306,311 | A | 4/1994 | Stone et al. | 623/18 |
| 5,314,478 | A | 5/1994 | Oka et al. | 623/18 |
| 5,314,482 | A | 5/1994 | Goodfellow et al. | 623/20 |
| 5,320,102 | A | 6/1994 | Paul et al. | 128/653.2 |
| 5,326,365 | A | 7/1994 | Alvine | 623/21 |
| 5,329,924 | A | 7/1994 | Bonutti | 128/653.1 |
| 5,344,459 | A | 9/1994 | Swartz | 623/18 |
| 5,360,446 | A | 11/1994 | Kennedy | 623/16 |
| 5,365,996 | A | 11/1994 | Crook | 164/45 |
| 5,368,858 | A | 11/1994 | Hunziker | 424/423 |
| 5,380,332 | A | 1/1995 | Ferrante | 606/79 |
| 5,387,216 | A | 2/1995 | Thornhill et al. | 606/88 |
| 5,413,116 | A | 5/1995 | Radke et al. | 128/777 |
| 5,423,828 | A | 6/1995 | Benson | 606/102 |
| 5,427,099 | A | 6/1995 | Adams | 128/653.1 |
| 5,433,215 | A | 7/1995 | Athanasiou et al. | 128/774 |
| 5,445,152 | A | 8/1995 | Bell et al. | 128/653.5 |
| 5,448,489 | A | 9/1995 | Reuben | 700/163 |
| 5,468,787 | A | 11/1995 | Braden et al. | 523/113 |
| 5,474,559 | A | 12/1995 | Bertin et al. | 606/89 |
| 5,478,739 | A | 12/1995 | Slivka et al. | 435/240.23 |
| 5,480,430 | A | 1/1996 | Carlisle et al. | 623/8 |
| 5,501,687 | A | 3/1996 | Willert et al. | 606/94 |
| 5,503,162 | A | 4/1996 | Athanasiou et al. | 128/774 |
| 5,507,820 | A | 4/1996 | Pappas | 623/20 |
| 5,510,121 | A | 4/1996 | Rhee et al. | 424/520 |
| 5,522,900 | A | 6/1996 | Hollister | 623/18 |
| 5,523,843 | A | 6/1996 | Yamane et al. | 356/363 |
| 5,533,519 | A | 7/1996 | Radke et al. | 128/777 |
| 5,540,696 | A | 7/1996 | Booth, Jr. et al. | 606/88 |
| 5,541,515 | A | 7/1996 | Tsujita | 324/318 |
| 5,542,947 | A | 8/1996 | Treacy | 606/88 |
| 5,549,690 | A | 8/1996 | Hollister et al. | 623/21 |
| 5,554,190 | A | 9/1996 | Draenert | 623/16 |
| 5,556,432 | A | 9/1996 | Kubein-Meesenburg et al. | 623/20 |
| 5,560,096 | A | 10/1996 | Stephens | 29/558 |
| 5,562,094 | A | 10/1996 | Bonutti | 128/653.1 |
| 5,564,437 | A | 10/1996 | Bainville et al. | 128/774 |
| 5,571,191 | A | 11/1996 | Fitz | 623/17 |
| 5,575,793 | A | 11/1996 | Carls et al. | 606/80 |
| 5,578,037 | A | 11/1996 | Sanders et al. | 606/80 |
| 5,591,165 | A | 1/1997 | Jackson | 606/61 |
| 5,593,450 | A | 1/1997 | Scott et al. | 623/20 |
| 5,597,379 | A | 1/1997 | Haines et al. | 606/80 |
| 5,601,563 | A | 2/1997 | Burke et al. | 606/86 |
| 5,609,640 | A | 3/1997 | Johnson | 623/20.2 |
| 5,616,146 | A | 4/1997 | Murray | 606/80 |
| 5,630,820 | A | 5/1997 | Todd | 606/90 |
| 5,632,745 | A | 5/1997 | Schwartz | 606/75 |
| 5,649,929 | A | 7/1997 | Callaway | 606/88 |
| 5,671,741 | A | 9/1997 | Lang et al. | 128/653.2 |
| 5,681,354 | A | 10/1997 | Eckhoff | 623/20 |
| 5,682,886 | A | 11/1997 | Delp et al. | 128/653.1 |
| 5,683,466 | A | 11/1997 | Vitale | 623/18 |
| 5,683,468 | A | 11/1997 | Pappas | 623/20 |
| 5,683,470 | A | 11/1997 | Johnson et al. | 623/20 |
| 5,684,562 | A | 11/1997 | Fujieda | 351/212 |
| 5,687,210 | A | 11/1997 | Maitrejean et al. | 378/57 |
| 5,690,635 | A | 11/1997 | Matsen, III et al. | 606/88 |
| 5,702,463 | A | 12/1997 | Pothier et al. | 623/20 |
| 5,723,331 | A | 3/1998 | Tubo et al. | 435/366 |
| 5,728,162 | A | 3/1998 | Eckhoff | 623/20 |
| 5,735,277 | A | 4/1998 | Schuster | 128/653.1 |
| 5,749,362 | A | 5/1998 | Funda et al. | 128/653.1 |
| 5,749,874 | A | 5/1998 | Schwartz | 606/75 |
| 5,749,876 | A | 5/1998 | Duvillier et al. | 606/88 |
| 5,759,205 | A | 6/1998 | Valentini | 623/16 |
| 5,768,134 | A | 6/1998 | Swaelens et al. | 364/468.28 |
| 5,769,899 | A | 6/1998 | Schwartz et al. | 623/18 |
| 5,772,595 | A | 6/1998 | Votruba et al. | 600/415 |
| 5,779,651 | A | 7/1998 | Buschmann et al. | 600/587 |
| 5,786,217 | A | 7/1998 | Tubo et al. | 435/402 |

5,788,701 A 8/1998 McCue ..... 606/88
5,810,006 A 9/1998 Votruba et al. ..... 128/653.2
5,824,085 A 10/1998 Sahay et al. ..... 623/16
5,824,102 A 10/1998 Buscayret ..... 623/20
5,827,289 A 10/1998 Reiley et al. ..... 606/86
5,832,422 A 11/1998 Wiedenhoefer ..... 702/154
5,835,619 A 11/1998 Morimoto et al. ..... 382/132
5,842,477 A 12/1998 Naughton et al. ..... 128/898
5,847,804 A 12/1998 Sarver et al. ..... 351/206
5,853,746 A 12/1998 Hunziker ..... 424/426
5,861,175 A 1/1999 Walters et al. ..... 424/486
5,871,018 A 2/1999 Delp et al. ..... 128/898
5,871,540 A 2/1999 Weissman et al. ..... 623/20
5,871,542 A 2/1999 Goodfellow et al. ..... 623/20
5,871,546 A 2/1999 Colleran et al. ..... 623/20
5,879,390 A 3/1999 Kubein-Meesenburg et al. ..... 623/20
5,880,976 A 3/1999 DiGioia, III et al. ..... 364/578
5,885,296 A 3/1999 Masini ..... 606/86
5,885,298 A 3/1999 Herrington et al. ..... 606/88
5,895,428 A 4/1999 Berry ..... 623/17
5,897,559 A 4/1999 Masini ..... 606/86
5,899,859 A 5/1999 Votruba et al. ..... 600/415
5,900,245 A 5/1999 Sawhney et al. ..... 424/426
5,906,934 A 5/1999 Grande et al. ..... 435/325
5,911,723 A 6/1999 Ashby et al. ..... 606/88
5,913,821 A 6/1999 Farese et al. ..... 600/425
5,916,220 A 6/1999 Masini ..... 606/88
5,928,945 A 7/1999 Seliktar et al. ..... 435/395
5,939,323 A 8/1999 Valentini et al. ..... 435/395
5,961,454 A 10/1999 Kooy et al. ..... 600/407
5,961,523 A 10/1999 Masini ..... 606/86
5,968,051 A 10/1999 Luckman et al. ..... 606/88
5,972,385 A 10/1999 Liu et al. ..... 424/486
5,995,738 A 11/1999 DiGioia, III et al. .... 395/500.32
6,001,895 A 12/1999 Harvey et al. ..... 523/113
6,002,859 A 12/1999 DiGioia, III et al. .... 395/500.32
6,007,537 A 12/1999 Burkinshaw et al. ..... 606/66
6,010,509 A 1/2000 Delgado et al. ..... 606/88
6,013,103 A 1/2000 Kaufman et al. ..... 623/20
6,044,289 A 3/2000 Bonutti ..... 600/415
6,046,379 A 4/2000 Stone et al. ..... 623/11
6,056,754 A 5/2000 Haines et al. ..... 606/80
6,056,756 A 5/2000 Eng et al. ..... 606/87
6,057,927 A 5/2000 Levesque et al. ..... 356/432 T
6,074,352 A 6/2000 Hynynen et al. ..... 601/3
6,078,680 A 6/2000 Yoshida et al. ..... 382/128
6,081,577 A 6/2000 Webber ..... 378/23
6,082,364 A 7/2000 Balian et al. ..... 128/898
6,090,144 A 7/2000 Letot et al. ..... 623/20
6,093,204 A 7/2000 Stone ..... 623/14.12
6,102,916 A 8/2000 Masini ..... 606/88
6,102,955 A 8/2000 Mendes et al. ..... 623/20.32
6,106,529 A 8/2000 Techiera ..... 606/88
6,110,209 A 8/2000 Stone ..... 623/16.11
6,112,109 A 8/2000 D'Urso ..... 600/407
6,120,541 A 9/2000 Johnson ..... 623/14.12
6,126,690 A 10/2000 Ateshian et al. ..... 623/18
6,132,468 A 10/2000 Mansmann ..... 623/20.16
6,139,578 A 10/2000 Lee et al. ..... 623/16.11
6,141,579 A 10/2000 Bonutti ..... 600/415
6,146,422 A 11/2000 Lawson ..... 623/17.16
6,151,521 A 11/2000 Guo et al. ..... 600/407
6,156,069 A 12/2000 Amstutz ..... 623/22.11
6,161,080 A 12/2000 Aouni-Ateshian et al. ..... 703/11
6,165,221 A 12/2000 Schmotzer ..... 623/20.11
6,171,340 B1 1/2001 McDowell ..... 623/18.11
6,175,655 B1 1/2001 George, III et al. ..... 382/257
6,178,225 B1 1/2001 Zur et al. ..... 378/98.2
6,187,010 B1 2/2001 Masini ..... 606/86
6,197,064 B1 3/2001 Haines et al. ..... 623/20.31
6,200,606 B1 3/2001 Peterson et al. ..... 424/574
6,203,546 B1 3/2001 MacMahon ..... 606/87
6,203,576 B1 3/2001 Afriat et al. ..... 623/20.27
6,205,411 B1 3/2001 DiGioia, III et al. ..... 703/11
6,206,927 B1 3/2001 Fell et al. ..... 623/20.29
6,214,369 B1 4/2001 Grande et al. ..... 424/423
6,217,894 B1 4/2001 Sawhney et al. ..... 424/426
6,219,571 B1 4/2001 Hargreaves et al. ..... 600/410
6,224,632 B1 5/2001 Pappas et al. ..... 623/20.34
6,228,116 B1 5/2001 Ledergerber ..... 623/8
6,235,060 B1 5/2001 Kubein-Meesenburg et al. ..... 623/20.31
6,249,692 B1 6/2001 Cowin ..... 600/407
6,251,143 B1 6/2001 Schwartz et al. ..... 623/23.72
6,261,296 B1 7/2001 Aebi et al. ..... 606/90
6,277,151 B1 8/2001 Lee et al. ..... 623/23.61
6,281,195 B1 8/2001 Rueger et al. ..... 514/21
6,283,980 B1 9/2001 Vibe-Hansen et al. ..... 606/151
6,289,115 B1 9/2001 Takeo ..... 382/130
6,289,753 B1 9/2001 Basser et al. ..... 73/866
6,296,646 B1 10/2001 Williamson ..... 606/90
6,299,905 B1 10/2001 Peterson et al. ..... 424/486
6,302,582 B1 10/2001 Nord et al. ..... 378/207
6,310,477 B1 10/2001 Schneider ..... 324/307
6,310,619 B1 10/2001 Rice ..... 345/420
6,311,083 B1 10/2001 Abraham-Fuchs et al. .. 600/407
6,316,153 B1 11/2001 Goodman et al. ..... 430/8
6,319,712 B1 11/2001 Meenen et al. ..... 435/395
6,322,588 B1 11/2001 Ogle et al. ..... 623/1.46
6,328,765 B1 12/2001 Hardwick et al. ..... 623/23.72
6,334,006 B1 12/2001 Tanabe ..... 385/12
6,334,066 B1 12/2001 Rupprecht et al. ..... 600/411
6,342,075 B1 1/2002 MacArthur ..... 623/20.14
6,344,043 B1 2/2002 Pappas ..... 606/96
6,344,059 B1 2/2002 Krakovits et al. ..... 623/20.31
6,352,558 B1 3/2002 Spector ..... 623/18.11
6,358,253 B1 3/2002 Torrie et al. ..... 606/96
6,365,405 B1 4/2002 Salzmann et al. ..... 435/366
6,368,613 B1 4/2002 Walters et al. ..... 424/423
6,371,958 B1 4/2002 Overaker ..... 606/72
6,373,250 B1 4/2002 Tsoref et al. ..... 324/309
6,375,658 B1 4/2002 Hangody et al. ..... 606/80
6,379,367 B1 4/2002 Vibe-Hansen et al. ..... 606/151
6,379,388 B1 4/2002 Ensign et al. ..... 623/20.34
6,382,028 B1 5/2002 Wooh et al. ..... 73/602
6,383,228 B1 5/2002 Schmotzer ..... 623/23.35
6,387,131 B1 5/2002 Miehlke et al. ..... 623/20.15
6,405,068 B1 6/2002 Pfander et al. ..... 600/407
6,425,920 B1 7/2002 Hamada ..... 623/17.16
6,429,013 B1 8/2002 Halvorsen et al. ..... 435/377
6,443,988 B2 9/2002 Felt et al. ..... 623/17.12
6,443,991 B1 9/2002 Running ..... 623/20.27
6,444,222 B1 9/2002 Asculai et al. ..... 424/484
6,450,978 B1 9/2002 Brosseau et al. ..... 600/595
6,459,948 B1 10/2002 Ateshian et al. ..... 700/117
6,468,314 B2 10/2002 Schwartz et al. ..... 623/23.72
6,478,799 B1 11/2002 Williamson ..... 606/90
6,479,996 B1 11/2002 Hoogeveen et al. ..... 324/309
6,482,209 B1 11/2002 Engh et al. ..... 606/79
6,494,914 B2 12/2002 Brown et al. ..... 623/20.3
6,500,208 B1 12/2002 Metzger et al. ..... 623/20.28
6,503,280 B2 1/2003 Repicci ..... 623/20.14
6,510,334 B1 1/2003 Schuster et al. ..... 600/407
6,514,514 B1 2/2003 Atkinson et al. ..... 424/423
6,520,964 B2 2/2003 Tallarida et al. ..... 396/567
6,533,737 B1 3/2003 Brosseau et al. ..... 600/595
6,556,855 B2 4/2003 Thesen ..... 600/419
6,558,421 B1 5/2003 Fell et al. ..... 623/14.12
6,560,476 B1 5/2003 Pelletier et al. ..... 600/410
6,569,172 B2 5/2003 Asculai et al. ..... 606/151
6,575,980 B1 6/2003 Robie et al. ..... 606/88
6,575,986 B2 6/2003 Overaker ..... 606/151
6,576,015 B2 6/2003 Geistlich et al. ..... 623/16.11
6,585,666 B2 7/2003 Suh et al. ..... 600/587
6,610,089 B1 8/2003 Liu et al. ..... 623/17.11
6,620,168 B1 9/2003 Lombardo et al. ..... 606/88
6,623,526 B1 9/2003 Lloyd ..... 623/20.28
6,626,945 B2 9/2003 Simon et al. ..... 623/17.19
6,626,948 B2 9/2003 Storer et al. ..... 623/23.14
6,632,235 B2 10/2003 Weikel et al. ..... 606/192
6,632,246 B1 10/2003 Simon et al. ..... 623/14.12
6,652,587 B2 11/2003 Felt et al. ..... 623/20.16
6,679,917 B2 1/2004 Ek ..... 623/20.14
6,689,139 B2 2/2004 Horn ..... 606/87
6,690,761 B2 2/2004 Lang et al. ..... 378/56
6,690,816 B2 2/2004 Aylward et al. ..... 382/128
6,695,848 B2 2/2004 Haines ..... 606/79

6,702,821 B2 3/2004 Bonutti ..... 606/88
6,712,856 B1 3/2004 Carignan et al. ..... 623/20.35
6,719,794 B2 4/2004 Gerber et al. ..... 623/17.11
6,726,724 B2 4/2004 Repicci ..... 623/20.29
6,743,232 B2 6/2004 Overaker et al. ..... 606/72
6,770,099 B2 8/2004 Andriacchi et al. ..... 623/20.35
6,772,026 B2 8/2004 Bradbury et al. ..... 700/98
6,799,066 B2 9/2004 Steines et al. ..... 600/407
6,811,310 B2 11/2004 Lang et al. ..... 378/169
6,816,607 B2 11/2004 O'Donnell et al. ..... 382/131
6,835,377 B2 12/2004 Goldberg et al. ..... 424/93.7
6,838,493 B2 1/2005 Williams et al. ..... 523/124
6,841,150 B2 1/2005 Halvorsen et al. ..... 424/93.7
6,855,165 B2 2/2005 Fell et al. ..... 623/14.12
6,866,668 B2 3/2005 Giannetti et al. ..... 606/99
6,866,684 B2 3/2005 Fell et al. ..... 623/20.3
6,869,447 B2 3/2005 Lee et al. ..... 623/20.15
6,873,741 B2 3/2005 Li ..... 382/266
6,893,463 B2 5/2005 Fell et al. ..... 623/14.12
6,904,123 B2 6/2005 Lang ..... 378/54
6,905,514 B2 6/2005 Carignan et al. ..... 623/20.35
6,911,044 B2 6/2005 Fell et al. ..... 623/14.12
6,916,324 B2 7/2005 Sanford et al. ..... 606/87
6,916,341 B2 7/2005 Rolston ..... 623/20.3
6,923,831 B2 8/2005 Fell et al. ..... 623/14.12
6,946,001 B2 9/2005 Sanford et al. ..... 623/20.33
6,966,928 B2 11/2005 Fell et al. ..... 623/14.12
6,984,981 B2 1/2006 Tamez-Pena et al. ..... 324/309
6,998,841 B1 2/2006 Tamez-Pena et al. ..... 324/302
7,008,430 B2 3/2006 Dong et al. ..... 606/80
7,020,314 B1 3/2006 Suri et al. ..... 382/130
7,050,534 B2 5/2006 Lang ..... 378/54
7,058,159 B2 6/2006 Lang et al. ..... 378/54
7,058,209 B2 6/2006 Chen et al. ..... 382/117
7,060,074 B2 6/2006 Rosa et al. ..... 606/88
7,104,996 B2 9/2006 Bonutti ..... 606/86
7,104,997 B2 9/2006 Lionberger et al. ..... 606/88
7,105,026 B2 9/2006 Johnson et al. ..... 623/20.14
7,115,131 B2 10/2006 Engh et al. ..... 606/79
7,117,027 B2 10/2006 Zheng et al. ..... 600/426
7,120,225 B2 10/2006 Lang et al. ..... 378/54
7,141,053 B2 11/2006 Rosa et al. ..... 606/86
7,174,282 B2 2/2007 Hollister et al. ..... 703/2
7,184,814 B2 2/2007 Lang et al. ..... 600/416
7,201,755 B2 4/2007 Faoro et al. ..... 606/88
7,239,908 B1 7/2007 Alexander et al. ..... 600/427
7,245,697 B2 7/2007 Lang ..... 378/54
7,282,054 B2 10/2007 Steffensmeier et al. ..... 606/96
7,292,674 B2 11/2007 Lang ..... 378/54
7,344,540 B2 3/2008 Smucker et al. ..... 606/87
7,344,541 B2 3/2008 Haines et al. ..... 606/88
7,379,529 B2 5/2008 Lang ..... 378/54
7,438,685 B2 10/2008 Burdette et al. ..... 600/439
7,467,892 B2 12/2008 Lang et al. ..... 378/207
7,468,075 B2 12/2008 Lang et al. ..... 623/16.11
7,520,901 B2 4/2009 Engh et al. ..... 623/20.21
7,534,263 B2 5/2009 Burdulis, Jr. et al. ..... 623/14.12
7,545,964 B2 6/2009 Lang et al. ..... 382/128
7,580,504 B2 8/2009 Lang et al. ..... 378/56
7,618,451 B2 11/2009 Berez et al. ..... 623/14.12
7,634,119 B2 12/2009 Tsougarakis et al. ..... 382/128
7,660,453 B2 2/2010 Lang ..... 382/132
7,664,298 B2 2/2010 Lang et al. ..... 382/128
7,676,023 B2 3/2010 Lang ..... 378/54
7,717,956 B2 5/2010 Lang ..... 623/14.12
7,796,791 B2 9/2010 Tsougarakis et al. ..... 382/128
7,799,077 B2 9/2010 Lang et al. ..... 623/14.12
7,840,247 B2 11/2010 Liew et al. ..... 600/407
7,881,768 B2 2/2011 Lang et al. ..... 600/407
7,981,158 B2 7/2011 Fitz et al. ..... 623/17.16
7,995,822 B2 8/2011 Lang et al. ..... 328/128
8,000,441 B2 8/2011 Lang et al. ..... 378/56
2001/0001120 A1 5/2001 Masini ..... 606/86
2001/0010023 A1 7/2001 Schwartz et al. ..... 623/23.72
2001/0039455 A1 11/2001 Simon et al. ..... 623/23.51
2001/0051830 A1 12/2001 Tuke et al. ..... 623/22.12
2002/0013626 A1 1/2002 Geistlich et al. ..... 623/23.57
2002/0016543 A1 2/2002 Tyler ..... 600/410
2002/0022884 A1 2/2002 Mansmann ..... 623/14.12
2002/0029038 A1 3/2002 Haines ..... 606/54
2002/0045940 A1 4/2002 Giannetti et al. ..... 623/11.11
2002/0049382 A1 4/2002 Suh et al. ..... 600/449
2002/0059049 A1 5/2002 Bradbury et al. ..... 703/11
2002/0067798 A1 6/2002 Lang et al. ..... 378/54
2002/0068979 A1 6/2002 Brown et al. ..... 623/20.3
2002/0082703 A1 6/2002 Repicci ..... 623/20.29
2002/0087274 A1 7/2002 Alexander et al. ..... 702/19
2002/0106625 A1 8/2002 Hung et al. ..... 435/1.1
2002/0111694 A1 8/2002 Ellingsen et al. ..... 623/23.57
2002/0114425 A1 8/2002 Lang ..... 378/56
2002/0115647 A1 8/2002 Halvorsen et al. ..... 514/171
2002/0120274 A1 8/2002 Overaker et al. ..... 606/72
2002/0120281 A1 8/2002 Overaker ..... 606/151
2002/0127264 A1 9/2002 Felt et al. ..... 424/423
2002/0133230 A1 9/2002 Repicci ..... 623/20.29
2002/0143402 A1 10/2002 Steinberg ..... 623/22.16
2002/0147392 A1 10/2002 Steines et al. ..... 600/407
2002/0151986 A1 10/2002 Asculai et al. ..... 424/484
2002/0156150 A1 10/2002 Asculai et al. ..... 623/23.75
2002/0173852 A1 11/2002 Felt et al. ..... 623/20.32
2002/0177770 A1 11/2002 Lang et al. ..... 600/410
2002/0183850 A1 12/2002 Felt et al. ..... 623/20.16
2002/0186818 A1 12/2002 Arnaud et al. ..... 378/165
2003/0015208 A1 1/2003 Lang et al. ..... 128/922
2003/0028196 A1 2/2003 Bonutti ..... 606/87
2003/0031292 A1 2/2003 Lang ..... 378/54
2003/0045935 A1 3/2003 Angelucci et al. ..... 623/17.11
2003/0055500 A1 3/2003 Fell et al. ..... 623/14.12
2003/0055501 A1 3/2003 Fell et al. ..... 623/14.12
2003/0055502 A1 3/2003 Lang et al. ..... 623/16.11
2003/0060882 A1 3/2003 Fell et al. ..... 623/14.12
2003/0060883 A1 3/2003 Fell et al. ..... 623/14.12
2003/0060884 A1 3/2003 Fell et al. ..... 623/14.12
2003/0060885 A1 3/2003 Fell et al. ..... 623/14.12
2003/0063704 A1 4/2003 Lang ..... 378/54
2003/0100907 A1 5/2003 Rosa et al. ..... 606/88
2003/0100953 A1 5/2003 Rosa et al. ..... 623/20.3
2003/0112921 A1 6/2003 Lang et al. ..... 378/54
2003/0120347 A1 6/2003 Steinberg ..... 623/22.17
2003/0158558 A1 8/2003 Horn ..... 606/87
2003/0158606 A1 8/2003 Coon et al. ..... 623/20.15
2003/0163137 A1 8/2003 Smucker et al. ..... 606/87
2003/0173695 A1 9/2003 Monkhouse et al. ..... 264/40.1
2003/0216669 A1 11/2003 Lang et al. ..... 600/587
2003/0225457 A1 12/2003 Justin et al. ..... 623/20.14
2003/0236473 A1 12/2003 Dore et al. ..... 600/587
2003/0236521 A1 12/2003 Brown et al. ..... 606/80
2004/0062358 A1 4/2004 Lang et al. ..... 378/207
2004/0081287 A1 4/2004 Lang et al. ..... 378/210
2004/0098132 A1 5/2004 Andriacchi et al. ..... 623/20.35
2004/0098133 A1 5/2004 Carignan et al. ..... 623/20.35
2004/0102851 A1 5/2004 Saladino ..... 623/20.15
2004/0102852 A1 5/2004 Johnson et al. ..... 623/20.15
2004/0106868 A1 6/2004 Liew et al. ..... 600/442
2004/0117015 A1 6/2004 Biscup ..... 623/16.11
2004/0122521 A1 6/2004 Lee et al. ..... 623/20.15
2004/0133276 A1 7/2004 Lang et al. ..... 623/14.12
2004/0138754 A1 7/2004 Lang et al. ..... 623/20.14
2004/0147927 A1 7/2004 Tsougarakis et al. ..... 606/53
2004/0153079 A1 8/2004 Tsougarakis et al. ..... 606/77
2004/0153162 A1 8/2004 Sanford et al. ..... 606/87
2004/0153164 A1 8/2004 Sanford et al. ..... 623/20.29
2004/0167390 A1 8/2004 Alexander et al. ..... 600/410
2004/0167630 A1 8/2004 Rolston ..... 623/20.3
2004/0193280 A1 9/2004 Webster et al. ..... 623/20.33
2004/0204644 A1 10/2004 Tsougarakis et al. ..... 600/410
2004/0204760 A1 10/2004 Fitz et al. ..... 623/14.12
2004/0204766 A1 10/2004 Siebel ..... 623/20.31
2004/0236424 A1 11/2004 Berez et al. ..... 623/14.12
2004/0242987 A1 12/2004 Liew et al. ..... 600/407
2004/0249386 A1 12/2004 Faoro et al. ..... 606/88
2005/0010106 A1 1/2005 Lang et al. ..... 600/425
2005/0015153 A1 1/2005 Goble et al. ..... 623/23.46
2005/0021039 A1 1/2005 Cusick et al. ..... 606/88
2005/0043807 A1 2/2005 Wood ..... 623/20.14
2005/0055028 A1 3/2005 Haines ..... 606/79
2005/0078802 A1 4/2005 Lang et al. ..... 378/207
2005/0085920 A1 4/2005 Williamson ..... 623/20.14

| | | | | |
|---|---|---|---|---|
| 2005/0107883 | A1 | 5/2005 | Goodfried et al. | 623/20.15 |
| 2005/0107884 | A1 | 5/2005 | Johnson et al. | 623/20.14 |
| 2005/0119664 | A1 | 6/2005 | Carignan et al. | 606/96 |
| 2005/0119751 | A1 | 6/2005 | Lawson | 623/17.16 |
| 2005/0143745 | A1 | 6/2005 | Hodorek et al. | 606/87 |
| 2005/0148843 | A1 | 7/2005 | Roose | 600/407 |
| 2005/0148860 | A1 | 7/2005 | Liew et al. | 600/410 |
| 2005/0171612 | A1 | 8/2005 | Rolston | 623/20.19 |
| 2005/0192588 | A1 | 9/2005 | Garcia | 606/88 |
| 2005/0226374 | A1 | 10/2005 | Lang et al. | 378/54 |
| 2005/0234461 | A1 | 10/2005 | Burdulis, Jr. et al. | 606/79 |
| 2005/0267584 | A1 | 12/2005 | Burdulis, Jr. et al. | 623/20.19 |
| 2006/0062442 | A1 | 3/2006 | Arnaud et al. | 382/128 |
| 2006/0074432 | A1 | 4/2006 | Stad et al. | 606/90 |
| 2006/0111722 | A1 | 5/2006 | Bouadi | 606/79 |
| 2006/0111726 | A1 | 5/2006 | Felt et al. | 606/86 |
| 2006/0136067 | A1 | 6/2006 | Pendleton et al. | 623/20.34 |
| 2006/0184176 | A1 | 8/2006 | Straszheim-Morley et al. | 606/88 |
| 2006/0195196 | A1 | 8/2006 | Pendleton et al. | 623/20.34 |
| 2006/0200162 | A1 | 9/2006 | Farling et al. | 606/88 |
| 2006/0210017 | A1 | 9/2006 | Lang | 378/54 |
| 2006/0210018 | A1 | 9/2006 | Lang | 378/54 |
| 2006/0235421 | A1 | 10/2006 | Rosa et al. | 606/88 |
| 2007/0015995 | A1 | 1/2007 | Lang et al. | 600/407 |
| 2007/0047794 | A1 | 3/2007 | Lang et al. | 378/132 |
| 2007/0067032 | A1 | 3/2007 | Felt et al. | 623/14.12 |
| 2007/0073305 | A1 | 3/2007 | Lionberger et al. | 606/87 |
| 2007/0083266 | A1 | 4/2007 | Lang | 623/17.11 |
| 2007/0100462 | A1 | 5/2007 | Lang et al. | 623/20.29 |
| 2007/0118141 | A1 | 5/2007 | Marchyn et al. | 606/88 |
| 2007/0118222 | A1 | 5/2007 | Lang | 623/17.12 |
| 2007/0156171 | A1 | 7/2007 | Lang et al. | 606/205 |
| 2007/0198022 | A1 | 8/2007 | Lang et al. | 606/88 |
| 2007/0203430 | A1 | 8/2007 | Lang et al. | 600/587 |
| 2007/0233269 | A1 | 10/2007 | Steines et al. | 623/20.21 |
| 2007/0250169 | A1 | 10/2007 | Lang | 623/17.12 |
| 2007/0274444 | A1 | 11/2007 | Lang | 378/54 |
| 2007/0276224 | A1 | 11/2007 | Lang et al. | 600/410 |
| 2007/0293868 | A1 | 12/2007 | Delfosse et al. | 606/88 |
| 2008/0004709 | A1 | 1/2008 | O'Neill et al. | 623/20.35 |
| 2008/0009950 | A1 | 1/2008 | Richardson | 623/20.29 |
| 2008/0015433 | A1 | 1/2008 | Alexander et al. | 600/427 |
| 2008/0025463 | A1 | 1/2008 | Lang | 378/54 |
| 2008/0031412 | A1 | 2/2008 | Lang et al. | 378/54 |
| 2008/0058613 | A1 | 3/2008 | Lang et al. | 600/300 |
| 2008/0097794 | A1 | 4/2008 | Arnaud et al. | 705/3 |
| 2008/0170659 | A1 | 7/2008 | Lang et al. | 378/56 |
| 2008/0172125 | A1 | 7/2008 | Ek | 623/14.12 |
| 2008/0195216 | A1 | 8/2008 | Philipp | 623/18.11 |
| 2008/0215059 | A1 | 9/2008 | Carignan et al. | 606/96 |
| 2008/0219412 | A1 | 9/2008 | Lang | 378/207 |
| 2008/0243127 | A1 | 10/2008 | Lang et al. | 606/87 |
| 2008/0275452 | A1 | 11/2008 | Lang et al. | 606/88 |
| 2008/0281328 | A1 | 11/2008 | Lang et al. | 606/87 |
| 2008/0281329 | A1 | 11/2008 | Fitz et al. | 623/17.16 |
| 2008/0281426 | A1 | 11/2008 | Fitz et al. | 623/17.16 |
| 2009/0076371 | A1 | 3/2009 | Lang et al. | 600/407 |
| 2009/0131941 | A1 | 5/2009 | Park et al. | 606/87 |
| 2009/0222014 | A1 | 9/2009 | Bojarski et al. | 606/88 |
| 2009/0276045 | A1 | 11/2009 | Lang | 623/14.12 |
| 2009/0306676 | A1 | 12/2009 | Lang et al. | 606/102 |
| 2009/0307893 | A1 | 12/2009 | Burdulis, Jr. et al. | 29/527.1 |
| 2009/0312805 | A1 | 12/2009 | Lang et al. | 606/86 R |
| 2010/0054572 | A1 | 3/2010 | Tsougarakis et al. | 382/131 |
| 2010/0281678 | A1 | 11/2010 | Burdulis, Jr. et al. | 29/592 |
| 2010/0298894 | A1 | 11/2010 | Bojarski et al. | 606/86 R |
| 2010/0305573 | A1 | 12/2010 | Fitz et al. | 606/87 |
| 2010/0305574 | A1 | 12/2010 | Fitz et al. | 606/88 |
| 2010/0331991 | A1 | 12/2010 | Wilkinson et al. | 623/20.32 |
| 2011/0066193 | A1 | 3/2011 | Lang et al. | 606/86 R |
| 2011/0071581 | A1 | 3/2011 | Lang et al. | 606/86 R |
| 2011/0125009 | A1 | 5/2011 | Lang et al. | 600/425 |

FOREIGN PATENT DOCUMENTS

| | | |
|---|---|---|
| CN | 2305966 | 2/1999 |
| DE | 3516743 | 11/1986 |
| DE | 3933459 | 4/1991 |
| DE | 44 34 539 | 4/1996 |
| DE | 19926083 | 12/2000 |
| DE | 10055465 | 5/2002 |
| DE | 10135771 | 2/2003 |
| DE | 20303498 | 8/2003 |
| DE | 102006037067 | 2/2008 |
| EP | 0337901 | 10/1989 |
| EP | 0528080 | 2/1993 |
| EP | 0600806 | 6/1994 |
| EP | 0 704 193 | 4/1996 |
| EP | 0780090 | 6/1997 |
| EP | 0626156 | 7/1997 |
| EP | 0613380 | 12/1999 |
| EP | 1074229 | 2/2001 |
| EP | 1077253 | 2/2001 |
| EP | 1120087 | 8/2001 |
| EP | 1129675 | 9/2001 |
| EP | 0732091 | 12/2001 |
| EP | 0896825 | 7/2002 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| EP | 1327423 | 7/2003 |
| EP | 1219269 | 4/2004 |
| EP | 0530804 | 6/2004 |
| EP | 1437101 | 7/2004 |
| EP | 1132061 | 8/2004 |
| EP | 1550416 | 7/2005 |
| EP | 1070487 | 9/2005 |
| EP | 1683593 | 7/2006 |
| EP | 1550418 | 10/2006 |
| EP | 1550419 | 2/2007 |
| FR | 2589720 | 11/1985 |
| FR | 2740326 | 4/1997 |
| FR | 2795945 | 1/2001 |
| GB | 1451283 | 9/1976 |
| GB | 2291355 | 1/1996 |
| GB | 2304051 | 3/1997 |
| GB | 2348373 | 10/2000 |
| JP | 56-83343 | 7/1981 |
| JP | 61-247448 | 11/1986 |
| JP | 1-249049 | 10/1989 |
| JP | 05-184612 | 7/1993 |
| JP | 7-236648 | 9/1995 |
| JP | 8-173465 | 7/1996 |
| JP | 9-206322 | 8/1997 |
| JP | 11-19104 | 1/1999 |
| JP | 11-276510 | 10/1999 |
| WO | WO 87/02882 | 5/1987 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 96/25123 | 8/1996 |
| WO | WO 97/25942 | 7/1997 |
| WO | WO 97/26847 | 7/1997 |
| WO | WO 97/27885 | 8/1997 |
| WO | WO 97/38676 | 10/1997 |
| WO | WO 97/46665 | 12/1997 |
| WO | WO 98/08469 | 3/1998 |
| WO | WO 98/12994 | 4/1998 |
| WO | WO 98/20816 | 5/1998 |
| WO | WO 98/30617 | 7/1998 |
| WO | WO 98/32384 | 7/1998 |
| WO | WO 98/52498 | 11/1998 |
| WO | WO 99/02654 | 1/1999 |
| WO | WO 99/08598 | 2/1999 |
| WO | WO 99/08728 | 2/1999 |
| WO | WO 99/42061 | 8/1999 |
| WO | WO 99/47186 | 9/1999 |
| WO | WO 99/51719 | 10/1999 |
| WO | WO 99/56674 | 11/1999 |
| WO | WO 00/09179 | 2/2000 |

| | | |
|---|---|---|
| WO | WO 00/15153 | 3/2000 |
| WO | WO 00/35346 | 6/2000 |
| WO | WO 00/48550 | 8/2000 |
| WO | WO 00/59411 | 10/2000 |
| WO | WO 00/68749 | 11/2000 |
| WO | WO 00/74554 | 12/2000 |
| WO | WO 00/74741 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/68800 | 9/2001 |
| WO | WO 01/70142 | 9/2001 |
| WO | WO 01/77988 | 10/2001 |
| WO | WO 01/82677 | 11/2001 |
| WO | WO 01/91672 | 12/2001 |
| WO | WO 02/00270 | 1/2002 |
| WO | WO 02/00275 | 1/2002 |
| WO | WO 02/02158 | 1/2002 |
| WO | WO 02/22013 | 3/2002 |
| WO | WO 02/22014 | 3/2002 |
| WO | WO 02/23483 | 3/2002 |
| WO | WO 02/34310 | 5/2002 |
| WO | WO 02/36147 | 5/2002 |
| WO | WO 02/096268 | 12/2002 |
| WO | WO 03/007788 | 1/2003 |
| WO | WO 03/028566 | 4/2003 |
| WO | WO 03/047470 | 6/2003 |
| WO | WO 03/051210 | 6/2003 |
| WO | WO 03/061522 | 7/2003 |
| WO | WO 2004/006811 | 1/2004 |
| WO | WO 2004/032806 | 4/2004 |
| WO | WO 2004/043305 | 5/2004 |
| WO | WO 2004/047688 | 6/2004 |
| WO | WO 2004/049981 | 6/2004 |
| WO | WO 2004/051301 | 6/2004 |
| WO | WO 2004/073550 | 9/2004 |
| WO | WO 2005/016175 | 2/2005 |
| WO | WO 2005/020850 | 3/2005 |
| WO | WO 2005/051239 | 6/2005 |
| WO | WO 2005/051240 | 6/2005 |
| WO | WO 2006/058057 | 6/2006 |
| WO | WO 2006/060795 | 6/2006 |
| WO | WO 2006/065774 | 6/2006 |
| WO | WO 2006/127283 | 11/2006 |
| WO | WO 2007/041375 | 4/2007 |
| WO | WO 2007/062079 | 5/2007 |
| WO | WO 2007/092841 | 8/2007 |
| WO | WO 2007/109641 | 9/2007 |
| WO | WO 2008/101090 | 8/2008 |
| WO | WO 2008/112996 | 9/2008 |
| WO | WO 2008/157412 | 12/2008 |
| WO | WO 2009/111639 | 9/2009 |
| WO | WO 2009/140294 | 11/2009 |

OTHER PUBLICATIONS

Brandt et al., [English Translation], "Crigos—Development of a Compact Robot System for Image-Guided Orthopedic Surgery," *Der Orthopäde,* Springer-Verlag, vol. 29, No. 7, pp. 645-649 (Jul. 2000).
Caos, "Mis meets Caos Spring 2005 Symposium Schedule," *Caos Spring 2005 Symposium,* 9 pages (May 2005).
Chelule et al., "Patient-Specific Template to Preserve Bone Stock in Total Knee Replacement: Preliminary Results," *15th Annual ISTA Symposium,* 1 page (Sep. 2002).
Hafez et al., "Computer Assisted Total Knee Replacement: Could A Two-Piece Custom Template Replace The Complex Conventional Instrumentations?", Session 6: Novel Instruments; *Computer Aided Surgery,* vol. 9, No. 3, pp. 93-94 (Jun. 2004).
Hafez et al., "Computer-assisted Total Knee Arthroplasty Using Patient-specific Templating", *Clinical Orthopaedics and Related Research,* No. 444, pp. 184-192 (Mar. 2006).
Radermacher et al., "Computer Assisted Orthopedic Surgery By Means of Individual Templates•Aspects and Analysis of Potential Applications" *Proceedings of the First International Symposium On Medical Robotics and Computer Assisted Surgery,* vol. 1: Sessions I-III, MRCAS '94, Pittsburgh, PA, pp. 42-48 (Sep. 22-24, 1994).
Reddy et al., "Triple Quantum Sodium Imaging of Articular Cartilage," Dept. of Radiology, University of Pennsylvania, pp. 279-284 (1997).
Schiffers et al., "Planung und Ausführung von orthopädischen Operationen mit Hilfe von Individualschablonen", *Der Orthopäde,* Springer-Verlag, vol. 29, No. 7, pp. 636-640, (Jul. 2000).
Schiffers et al., [English Translation], "Planning and execution of orthopedic surgery using individualized templates," *Der Orthopäde,* Springer-Verlag, vol. 29, No. 7, pp. 636-640 (Jul. 2000).
Thoma et al., "Einsatz eines neuen 3D-computertomographischen Subtraktionsverfahrens zur individuellen Versorgung von Knochendefekten an Hüften und Knie", *Journal DGPW,* No. 17, pp. 27-28 (May 1999).
Thoma et al., [English Translation], "Use of a New Subtraction Procedure Based on Three-Dimensional CT Scans for the Individual Treatment of Bone Defects in the Hip and Knee," *Journal DGPW,* No. 17, pp. 27-28 (May 1999).
Thoma et al., "Endoprothetischen Versorgung des Kniegelenks auf der Basis eines 3D-computertomographischen Subtraktionsverfahrens", *Der Orthopäde,* Springer-Verlag, vol. 29, No. 7, pp. 641-644, (Jul. 2000).
Thoma et al., [English Translation], "Custom-made knee endoprosthetics using subtraction data of three-dimensional CT scans—A new approach," *Der Orthopäde,* Springer-Verlag, vol. 29, No. 7, pp. 641-644, (Jul. 2000).
Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989).
Adam et al., "MR Imaging of the Knee: Three-Dimensional Volume Imaging Combined with Fast Processing,"J. Compt. Asst. Tomogr., 13(6): 984-988 (1989).
Adams et al., "Quantitative Imaging of Osteoarthritis," Semin Arthritis Rheum, 20(6) Suppl. 2: 26-39 (Jun. 1991).
Ahmad et al., "Biomechanical and Topographic Considerations for Autologous Osteochondral Grafting in the Knee," Am J Sports Med, 29(2): 201-206 (Mar.-Apr. 2001).
Alexander, "Estimating the motion of bones from markers on the skin," University of Illinois at Chicago (Doctoral Dissertation) (1998).
Alexander et al., "Correcting for deformation in skin-based marker systems," Proceedings of the 3rd Annual Gait and Clinical Movement Analysis Meeting, San Diego, CA (1998).
Alexander et al., "Internal to external correspondence in the analysis of lower limb bone motion," Proceedings of the 1999 ASME Summer Bioengineering Conference, Big Sky, Montana (1999) .
Alexander et al., "State estimation theory in human movement analysis," Proceedings of the ASME International Mechanical Engineering Congress (1998).
Alexander et al., "Optimization techniques for skin deformation," International Symposium on 3-D Human Movement Conference, Chattanooga, TN, (1998).
Alexander et al., "Dynamic Functional Imaging Of The Musculoskeletal System," ASME Winter International Congress and Exposition, Nashville, TN (1999).
Allen et al., "Late degenerative changes after meniscectomy 5 factors affecting the knee after operations," J Bone Joint Surg 66B: 666-671 (1984).
Alley et al., "Ultrafast contrast-enhanced three dimensional MR Aagiography: State of the art," Radiographics 18: 273-285 (1998).
Andersson et al., "MacIntosh Arthroplasty in Rheumatoid Arthritis," Acta. Orthrop. Scand. 45(2):245-259 (1974).
Andriacchi, et al., "A point cluster method for in vivo motion analysis: Applied to a study of knee kinematics," J. Biomech Eng 120(12): 743-749 (1998).
Andriacchi, et al., "Methods for evaluating the progression of Osterarthiritis," Journal of Rehabilitation Research and Development 37(2): 163-170 (2000).
Aragenson et al., "Is There a Place for Patellofemoral Arthroplasty?," Clinical Orthopaedics and Related Research No. 321, pp. 162-167 (1995).
Aro et al., "Clinical Use of Bone Allografts," Ann Med 25:403-412 (1993).

Atheshian, "A B-Spline Least-Squares Surface-Fitting Method for Articular Surfaces of Diarthrodial Joints," Journal of Biomechanical Engineering Division, Transactions of the ASME 115: 366-373 (Nov. 1993).
Atheshian et al., "Curvature Characteristics and Congruence of the Thumb Carpometacarpal Joint-Differences Between Female and Male Joints," J. Biomechanics 25(6): 591-607 (1992).
Atheshian et al., "Quantitation of Articular Surface Topography and Cartilage Thickenss in Knee Joints Using Stereophotogammetry," Biomechanics, 24(8): 761-776 (1991).
Bashir, "Validation of Gadolinium-Enhanced MRI of FAF Measurement in Human Cartilage," Intl. Soc. Mag. Resonance Med. (1998).
Beaulieu et al., "Glenohumeral relationships during physiological shoulder motion and stress testing: Initial experience with open MRI and active Scan-25 plane registration," Radiology (1999).
Beaulieu et al., "Dynamic imaging of glenohumeral instability with open MRI," Int. Society for Magnetic Resonance in Medicine Sydney, Australia (1998).
Beckmann et al., "Noninvasive 3D MR Microscopy as Tool in Pharmacological Research: Application to a Model of Rheumatoid Arthritis," Magn Reson Imaging 13(7): 1013-1017 (1995).
Blazina et al., "Patellofemoral replacement: Utilizing a customized femoral groove replacement," 5(1)53-55 (1990).
Blum et al., "Knee Arthroplasty in Patients with Rheumatoid Arthritis," ANN. Rheum. Dis. 33 (1): 1-11 (1974).
Bobic, "Arthoroscopic osteochondral autogaft transplantation in anterior cruciate ligament reconstruction: a preliminary clinical study," Knee Surg Sports Traumatol Arthrosc 3(4): 262-264 (1996).
Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).
Borgefors, "Distance Transformations in Digital Images," Computer Vision, Graphics, and Image Processing 34: 344-371 (1986).
Borthakur et al., "In Vivo Triple Quantum Filtered Sodium MRI of Human Articular Cartilage," Proc. Intl. Soc. Mag. Resonance Med., 7:549 (1999).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chrondrocyte transplantation," N. Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Proc. Intl. Soc. Mag. Resonance Med., 7:169 (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
Carano et al., "Estimation Of Erosive Changes In Rheumatoid Arthritis By Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Castriota-Scanderbeg et al., "Precision of Sonographic Measurement of Articular Cartilage: Inter-and Intraobserver Analysis," Skeletal Radiol 25: 545-549 (1996).
Chan et al., "Osteoarthritis Of The Knee: Comparison Of Radiography, CT And MR Imaging To Asses Extent And Severity," AJR Am J Roentgenol 157(4): 799-806 (1991).
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).
Cohen et al., "Knee cartilage topography, thickness, and contact areas from MRI: in-vitro calibration and in-vivo measurements," Osteoarthritis and Cartilage 7: 95-109 (1999).
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).
Dardzinski et al., "T1-T2 Comparison in Adult Articular Cartilage," ISMRM Seventh Scientific Meeting, Philadelphia, PA (May 22-28, 1999).
Dardzinski et al., "Entropy Mapping of Articular Cartilage," Proc. Intl. Soc. Mag. Resonance Med., 7:1018 (1999).
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Dougados et al., "Longitudinal radiologic evaluation of osteoarthritis of the knee," J Theumatol 19: 378-394 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "In vivo reproducibility of three-dimensional cartilage volume and thickness measurements with MR imaging," AJR 170(3): 593-597 (1998).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient And Section Orientation On Quantitative Analyses of Knee Joint Cartilage," Journal of Magnetic Resonance Imaging 11: 161-167 (2000).
Eckstein et al., "Effect Of Physical Exercise On Cartilage volume And Thickness In Vivo: An MR Imaging Study," Radiology 207: 243-248 (1998).
Eckstein et al., "Functional Analysis Of Articular Cartilage Deformation, Recovery, And Fluid Flow Following Dynamic Exercise In Vivo," Anatomy and Embryology 200: 419-424 (1999).
Eckstein et al., "New Quantitative Approaches With 3-D MRI: Cartilage Morphology, Function And Degeneration," Medical Imaging International (Nov.-Dec. 1998).
Eckstein et al., "Side Differences Of Knee Joint Cartilage Volume, Thickness, And Surface Area, And Correlation With Lower Limb Dominance—An MRI-Based Study," Osteoarthritis and Cartilage 10: 914-921 (2002).

Eckstein F, et al., "Accuracy of Cartilage Volume and Thickness Measurements with Magnetic Resonance Imaging," Clin. Orthop. 352: 137-148 (1998).
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—A Finite Element Analysis," Anat Embryol, 189: 545-552 (1994).
Eckstein et al., "The Morphology of Articular Cartilage Assessed by Magnetic Resonance Imaging: Reproducibility and Anatomical Correlation," Sur. Radiol Anat 16: 429-438 (1994).
Faber et al., "Gender Differences In Knee Joint Cartilage Thickness, Volume And Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms: Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).
Gerscovich, "A Radiologist's Guide to the Imaging in the Diagnosis and Treatment of Developmental Dysplasia of the Hip," Skeletal Radiol 26: 447-456 (1997).
Ghosh et al., "Watershed Segmentation Of High Resolution Articular Cartilage Images For Assessment Of Osteoarthritis," International Society for Magnetic Resonance in Medicine, Philadelphia, (1999).
Glaser et al., "Optimization And Validation Of A Rapid Highresolution T1-W 3-D Flash Waterexcitation MR Sequence For The Quantitative Assessment Of Articular Cartilage Volume And Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).
Graichen et al., "Three-Dimensional Analysis Of The Width Of The Subacromial Space In Healthy Subjects And Patients With Impingement Syndrome," American Journal of Roentgenology 172: 1081-1086 (1999).
Hall et al., "Quantitative MRI For Clinical Drug Trials Of Joint Diseases; Virtual Biopsy Of Articular Cartilage" NIH-FDA Conf. on Biomarkers and Surrogate Endpoints: Advancing Clinical Research and Applications (1998).
Hardy et al., "Measuring The Thickness Of Articular Cartilage From MR Images," J. Magnetic Resonance Imaging 13 (2001).
Hardy et al., "The Influence of The Resolution And Contrast On Measuring The Articular Cartilage volume In Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Hastings et al., "Double Hemiarthroplasty of the Knee in Rheumatoid Arthritis," A Survey of Fifty Consecutive Cases, J. Bone Joint Surg. Br. 55(1):112-118 (1973).
Haubner M, et al., "A Non-Invasive Technique for 3-Dimensional Assessment of Articular Cartilage Thickness Based on Mri Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Henderson et al., "Experience with the Use of the Macintosh Prosthesis in Knees of Patients with Pheumatoid Arthritis," South. Med. J. 62(11):1311-1315 (1969).
Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold et al., "In Situ Measurement Of Articular Cartilage Deformation In Intact Femorapatellar Joints Under Static Loading," Journal of biomechanics 32: 1287-1295 (1999).
Henkelman et al., "Anisotropy of NMR properties of tissues," Magn Res Med. 32: 592-601 (1994).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe et al., "Surface Size, Curvature Analysis, And Assessment Of Knee Joint Incongruity With MR Imaging In Vivo," Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radio!: 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket Location in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Jessop et al., "Follow-up of the MacIntosh Arthroplasty of the Knee Joint," Rheumatol Phys. Med. 11(5):217-224 (1972).
Johnson et al., "The distribution of load across the knee. A comparison of static and dynamic measurements," J. Bone Joint Surg 62B: 346-349 (1980).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).
Karvonen et al., "Articular Cartilage Defects of the Knee: Correlation Between Magnetic Resonance Imaging and Gross Pathology," Ann Rheum Dis. 49: 672-675 (1990).
Kass et al., "Snakes: Active contour models.," Int J Comput Vision 1: 321-331 (1988).
Kates, et al., "Experiences of Arthroplasty of the Rheumatoid Knee Using MacIntosh Prostheses," Ann. Rheum. Dis. 28(3):328 (1969).
Kaufman et al., "Articular Cartilage Sodium content as a function of compression,"Proc. Intl. Soc. Mag. Resonance Med., 7:1022 (1999).
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning And Manufacturing Of Orthopaedic Devices: A Framework," Proceedings of the SPIE—Advanced Sensor and Control-System Interface, Boston, MA, vol. 2911, pp. 9-22, 21 (Nov. 1996).
Kiryati, "On Length Estimators, Distance Tranformations and Digital Lines in Three Dimensions," Progress in Image Analysis and Processing III, Proc. Of the 7th International Conference in Image Analysis and Processing, Capitolo, Italy, pp. 22-29 (1993).

Klosterman et al., "T2 Measurements in Adult Patellar Cartilage at 1.5 and 3.0 Tesla," ISMRM Seventh Scientific Meeting, Philadelphia, PA, (May 22-28, 1999).
Knauss et al., "Self-Diffusion of Water in Cartilage and Cartilage Components as Studied by Pulsed Field Gradient NMR," Magnetic Resonance in Medicine 41:285-292 (1999).
Koh et al., "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance Of The Superficial Tissue Layer For The Indentation Stiffness Of Articular Cartilage," Med. Eng. Phys; 24(2): 99-108 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement Of Localized Cartilage Volume And Thickness Of Human Knee Joints By Computer Analysis Of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).
LaFortune et al., "Three dimensional kinematics of the human knee during walking," J. Biomechanics 25: 347-357 (1992).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24 1998).
Ledingham et al., "Factors affecting radiographic progression of knee osteoarthritis," Ann Rheum Dis 54: 53-58 (1995).
Leenslag et al., "A Porous Composite for Reconstruction of Meniscus Lesions," Biological and Biomechanical Perform. of Biomaterials, Elsevier Science Publishers Amsterdam pp. 147-152 (1986).
Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker coordinates using globals optimization with joint constraints," J Biomechanics 32: 129-134 (1999).
Lucchetti et al., "Skin movement artifact assessment and compensation in the estimation of knee-joint kinematics," J Biomechanics 31: 977-984 (1998).
Lusse et al., "Measurement Of Distribution Of Water Content Of Human Articular Cartilage Based On Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego (Feb. 2000).
MacIntosh, "Arthroplasty Of The Knee In Rheumatoid Arthritis," Proceedings and Reports of Councils and Assotions, J. Bone & Joint Surg., vol. 48B No. (1): 179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Maki et al., "SNR improvement in NMR microscopy using DEFT," J Mag Res (1988).
Marshall et al., "Quantitation Of Articular Cartilage Using Magnetic Resonance Imaging And Three-Dimensional Reconstruction," J. Orthop. Res.; 13: 814-823 (1995).
Mattila et al., "Massive Osteoarticular Knee Allografts: Structural Changes Evaluated with CT," Radiology; 196: 657-660 (1995).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly For Hetero-Nuclear Investigations Of Human Breast At 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging Of The Knee: Evaluation Of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life," Am. J. Orthop. 739-744 (Nov. 27, 1998).
Modest et al., "Optical Verification Of A Technique For In Situ Ultrasonic Measurement Of Articular Cartilage Thickness," J. Biomechanics 22(2): 171-176 (1989).
Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint lmvolvement: A CT Scan Study," Clin. Orthop.; 304: 176-183 (Jul. 1994).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation Of The Acetabular And Femoral Articular Cartilage In The Osteoarthritis Of The Hip Joint," Proc. Intl. Soc. Mag. Resonance Med., 7:1030 (1999).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Parkkinen et al., "A Mechanical Apparatus With Microprocessor Controlled Stress Profile For Cyclic Compression Of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the carpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).

Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment Of Cartilage volume In The Femorotibial Joint With Magnetic Resonance Imaging And 3D Computer Reconstruction," J. Rheumatol. 21(12): 2307-2319 (1994).
Piplani et al., "Articular cartilage volume in the knee: semiautomated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51 B, pp. 76-87 (1969).
Porter et al., "MacIntosh Arthroplasty: A Long-Term Review," J. R. Coll. Surg. Edin. (192):199-201 (1988).
Portheine et al., "Development of a Clinical Demonstrator for Computer Assisted Orthopedic Surgery with CT Image Based Individual Templates," Computer Assisted Radiology and Surgery. Amsterdam, Elsevier 944-949 (1997).
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique For Measuring The Area Of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher, K., "Computer-Assisted Planning and Execution of Orthopedic Surgery Using Individual Surgical Templates," Helmholtz Institute of Biomedical Technology (May 18, 1999).
Radermacher et al., "Computer Assisted Orthopaedic Surgery With Image Based Individual Templates" Clinical Orthopaedics, vol. 354, pp. 28-38 (Sep. 1998).
Radermacher et al., "Image Guided Orthopedic Surgery Using Individual Templates—Experimental Results and Aspects of the Development of a Demonstrator for Pelvis Surgery," Computer Vision, Virtual Reality and Robotics in Medicine and Medical Robotics and Computer Assisted Surgery, Lecture Notes in Computer Science. Berlin, Springer-Verlag 606-616 (1997).
Radermacher et al., "Computer Integrated Orthopedic Surgery—Connection of Planning and Execution in Surgical Inventions," Computer Integrated Surgery, MIT Press, pp. 451-463 (1996).
Radermacher et al., "Technique for Better Execution of CT Scan Planned Orthopedic Surgery on Bone Structures," Computer Assisted Radiology, Berlin, Springer, pp. 933-938 (1995).
Radermacher et al., "CT Image Based Planning and Execution of Interventions in Orthopedic Surgery Using Individual Templates—Experimental Results and Aspects of Clinical Applications," Computer Assisted Orthopaedic Surgery. Bern, Hans Huber (1998).
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ragnemalm, "The Euclidean Distance Transform in Arbitrary Dimensions," Pattern Recognition Letters, North-Holland, vol. 14, No. 11, pp. 883-888 (Nov. 1993).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo Flash MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance In Cartilaginous Lesions Of The Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).
Robarts Research Institute, Abstract #1028.
Robson et al., "A Combined Analysis And Magnetic Resonance Imaging Technique For Computerized Automatic Measurement Of Cartilage Thickness In Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied et al., "Assessment of Articular Cartilage and Subchondral Bone: Subtle and Progressive Changes in Experimental Osteoarthritis Using 50 MHz Echography In Vitro," J. Bone Miner Res.; 12(9): 1378-1386 (1997).
Saito et al., "New algorithms for Euclidean distance transformation of an—dimensional digitized picture with applications," Pattern Recognition 27(11): 1551-1565 (1994).
Schipplein et al., "Interaction between active and passive knee stabilizers during level walking," J Orthop Res 9: 113-119 (1991).
Schorn et al., "MacIntosh Arthroplasty in Rheumatoid Arthritis," Rheumatol Rehabil. Aug. 1978:17(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 8 (1972).
Sittek et al., "Assessment of Normal Patellar Cartilage Volume and Thickness Using MRI: an Analysis of Currently Available Pulse Sequences," Skeletal Radiol; 25: 55-61 (1996).
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method For Quantifying Tithe Dependent Changes In MR Signal Intensity Of Articular Cartilage As A Function Of Tissue Deformation In Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration Of 3D Cartilage Surfaces From MR Image Data For Detecting Local Changes Of The Cartilage Thickness," Magnetic Resonance in Medicine 44: 592-601 (2000).

Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:1022 (2000).
Steines et al., "Segmentation of osteoarthritis femoral cartilage from MR images," CARS— Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Tebben et al., "Three-Dimensional Computerized Reconstruction. Illustration Of Incremental Articula Cartilage Thinning," Invest. Radiol. 32(8): 475-484 (1997).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000).
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).
Vande Berg et al., "Assessment of Knee Cartilage In Cadavers With Dual-Detector Spiral CT Arthrography and MR Imaging," Radiology,: 222(2): 430-435 (Feb. 2002).
Van der Linden et al., "MR Imaging of Hyaline Cartilage at 0.5 T: A Quantitative and Qualitative in vitro Evaluation of Three Types of Sequences" (Jun. 1998).
Velyvis et al., "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness In The Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Woolf et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
International Searching Authority, International Preliminary Examination Report—International Application No. PCT/US01/28679, dated Aug. 5, 2002, 2 pages.
International Searching Authority, International Search Report—International Application No. PCT/US01/28679, dated Feb. 27, 2002, 2 pages.
International Searching Authority, International Preliminary Examination Report—International Application No. PCT/US01/28680, dated Jul. 29, 2002, 2 pages.
International Searching Authority, International Search Report—International Application No. PCT/US01/28680, dated Feb. 27, 2002, 2 pages.
International Searching Authority, International Preliminary Examination Report—International Application No. PCT/US01/42155, dated Jan. 3, 2003, 2 pages.
International Searching Authority, International Search Report—International Application No. PCT/US01/42155, dated Oct. 29, 2002, 2 pages.
International Searching Authority, International Search Report—International Application No. PCT/US99/30265, dated Aug. 2, 2000, 5 pages.
Argenson et al., "Is There a Place for Patellofemoral Arthroplasty?," Clinical Orthopaedics and Related Research No. 321, pp. 162-167 (1995).
Billet, Philippe, Translated Version—"Gliding Knee Prostheses—Analysis of Mechanical Failures", Thesis, Medical School of Marseilles, 1982, 64 pages.
Brown et al., "MRI Basic Principles and Applications", Second Ed., Mark A. Brown and Richard C. Semelka, 1999, Wiley-Liss Inc., Title page and Table of Contents Pages Only (ISBN 0471330620).
Delp et al., "A Graphics-Based Software System to Develop and Analyze Models of Musculoskeletal Structures," Comput. Biol. Med., vol. 25, No. 1, pp. 21-34, 1995.
De Winter et al., "The Richards Type II Patellofemoral Arthroplasty", Acta Orthop Scand 2001; 72 (5): 487-490.
Ghelman et al., "Kinematics of the Knee After Prosthetic Replacements", Clin. Orthop. May 1975: (108): 149-157.
Lam et al., "X-Ray Diagnosis: A Physician's Approach", Editor Lam, 1998, Springer-Verlag publishers, Title page and Table of Contents pgs. Only (ISBN 9813083247).
Lu et al., "In vitro degradation of porous poly(L-lactic acid) foams", Biomaterials, 21(15):1595-1605, Aug. 2000.
Marler et al., "Soft-Tissue Augmentation with Injectable Alginate and Syngeneic Fibroblasts", Plastic & Reconstructive Surgery, 105(6):2049-2058, May 2000.
Matsen, III et al., "Robotic Assistance in Orthopaedic Surgery: A Proof of Principle Using Distal Femoral Arthroplasty", Clinical Ortho. and Related Research, 296:178-186 (1993).
Portheine et al. "CT-Based Planning and Individual Template Navigation in TKA", Navigation and Robotics in Total Joint and Spine Surgery, Springer, 48:336-342 (2004).
Slone et al., "Body CT: A Practical Approach", Editor Slone, 1999 McGraw-Hill publishers, Title page and Table of Contents pgs. Only (ISBN 007058219).

Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling And Design Of A Custom Made Cranium Implant For Large Skull Reconstruction Before A Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Wiese et al., "Biomaterial properties and biocompatibility in cell culture of a novel self-inflating hydrogel tissue expander", J. Biomedical Materials Research Part A, 54(2):179-188, Nov. 2000.
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report, International Application No. PCT/US03/38158, dated Feb. 23, 2005, 7 pages.
European Searching Authority, European Search Report—Application No. EP 03790194, dated Jul. 13, 2006, 7 pages.
International Searching Authority, International Search Report, International Application No. PCT/US03/32123, dated Mar. 17, 2004, 7 pages.
International Searching Authority, International Search Report, International Application No. PCT/US04/39616, dated Mar. 28, 2005, together with the Written Opinion of the International Searching Authority, 6 pages.
International Searching Authority, International Search Report, International Application No. PCT/US04/39714, dated May 13, 2005, together with the Written Opinion of the International Searching Authority, 8 pages.
International Searching Authority, International Search Report, International Application No. PCT/US05/044008, dated Mar. 30, 2006, together with the Written Opinion of the International Searching Authority, 12 pages.
International Searching Authority, International Search Report, International Application No. PCT/US06/045172, dated Apr. 19, 2007, 12 pages.
International Searching Authority, International Search Report, International Application No. PCT/US07/061681, dated Sep. 7, 2007, together with the Written Opinion of the International Searching Authority, 12 pages.
European Searching Authority, Supplementary European Search Report—Application No. 04812187.5, dated Sep. 27, 2007, 3 pages.
International Searching Authority, International Preliminary Report on Patentability—International Application No. PCT/US2005/044008, dated Jun. 14, 2007, together with the Written Opinion of the International Searching Authority, 8 pages.
United States Patent and Trademark Office, Office Action dated Jun. 15, 2007, pertaining to U.S. Appl. No. 09/882,363, 9 pages.
Bromberg & Sunstein LLP, Response to Office Action dated Jun. 15, 2007, pertaining to U.S. Appl. No. 09/882,363, 12 pages.
United States Patent and Trademark Office, Office Action dated Mar. 21, 2008, pertaining to U.S. Appl. No. 09/882,363, 12 pages.
Bromberg & Sunstein LLP, Response to Office Action dated Jan. 30, 2007, pertaining to U.S. Appl. No. 09/882,363, 7 pages.
International Searching Authority, International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark Office, Office Action dated Jan. 9, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 9 pages.
Bromberg & Sunstein LLP, United States Patent Application—U.S. Appl. No. 12/361,213, filed Jan. 28, 2009, 76 pages.
Bromberg & Sunstein LLP, United States Patent Application—U.S. Appl. No. 12/398,753, filed Mar. 5, 2009, 141 pages.
United States Patent and Trademark Office, Office Action dated Jan. 11, 2008, pertaining to U.S. Appl. No. 10/724,010, 12 pages.
Bromberg & Sunstein LLP, Response to Office Action dated Jan. 11, 2008, pertaining to U.S. Appl. No. 10/724,010, 14 pages.
United States Patent and Trademark Office, Office Action dated May 5, 2008, pertaining to U.S. Appl. No. 10/724,010, 31 pages.
Bromberg & Sunstein LLP, Request for Continued Examination and Response dated Nov. 4, 2008, pertaining to U.S. Appl. No. 10/724,010, 15 pages.
United States Patent and Trademark Office, Notice of Allowance and Fees Due dated Sep. 22, 2009, pertaining to U.S. Appl. No. 10/724,010, 19 pages.
United States Patent and Trademark Office, Office Action dated Mar. 6, 2007, pertaining to U.S. Appl. No. 11/002,573, 16 pages.
Bromberg & Sunstein LLP, Response to Office Action dated Mar. 6, 2007, pertaining to U.S. Appl. No. 11/002,573, 21 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
United States Patent and Trademark Office, Supplemental Notice of Allowability dated Nov. 28, 2008, pertaining to U.S. Appl. No. 11/002,573, 21 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office action dated Jan. 26, 2010, pertaining to U.S. Appl. No. 11/671,745, 48 pages.
Farrar et al., "Computed Tomography Scan Scout Film for Measurement of Femoral Axis in Knee Arthroplasty," J. Arthroplasty, vol. 14, No. 8, pp. 1030-1031, 1999.
Kim et al., "Measurement of Femoral Neck Anteversion in 3D. Part 1: 3D Imaging Method," Med. And Viol. Eng. And Computing, vol. 38, No. 6, pp. 603-609, 2000.
Lam et al., "Varus/Valgus Alignment of the Femoral Component in Total Knee Arthroplasty," The Knee, vol. 10, pp. 237-241, 2003.
Mahaisavariya et al., "Morphological Study of the Proximal Femur: A New Method of Geometrical Assessment Using 3 Dimensional Reverse Engineering," Med. Eng. And Phys., vol. 24, pp. 617-622, 2002.
Testi et al., "Border Tracing Algorithm Implementation for the Femoral Geometry Reconstruction," Comp. Meth. And Programs in Biomed., vol. 65, pp. 175-182, 2001.
Alexander E.J., "Estimating the motion of bones from markers on the skin (Doctoral Disseration)," University of Illinois at Chicago (1998).
Alexander E.J. and Andriacchi, T.P., "Correcting for deformation in skin-based marker systems," Proceedings of the 3rd Annual and Clinical Movement Analysis Meeting, San Diego, CA (1998).
Alexander E.J. and Andriacchi, T.P., "Internal to external corresponding in the analysis of lower limb bone motion," Proceedings of the 1999 ASME Summer Bioengineering Conference, Big Sky, Montana (1999).
Alexander E.J. and Andriacchi, T.P., "State estimation theory in human movement analysis," Proceedings of the 1998 ASME International Mechanical Engineering Congress (1998).
Andriacchi, T.P., "Dynamics of knee Malalignment," *Orthop Clin North Am* 25:395-403 (1994).
Andriacchi and Strickland, "Gait analysis as a tool to assess joint kinetics biomechanics of normal and pathological human articulating joints," *Nijhoff, Series E* 93:83-102 (1985).
Andriacchi and Toney, "In vivo measurement of six-degrees-of-freedom knee movement during functional testing," *Transactions of the Orthopedic Research Society* pp. 698 (1995).

Bobic, V., "Arthoscopic osteochondral autograft transplantation in anterior cruciate ligament reconstruction: a preliminary clinical study," *Knee Surg Sports Traumatol Arthrosc* 3(4):262-264 (1996).
Boe S., and Hansen H., "Arthroscopic partial meniscectomy in patients aged over 50," *J. Bone Joint Surg* 68B:707 (1986).
Bregler et al., "Recovering non-rigid 3D shape from image streams," *Proc.IEEE Conference on Computer Vision and Pattern Recognition* (2000) in press.
Doherty M, Hutton C, Bayliss MT: Osteoarthritis. In: Maddison PJ, Isenberg DA, Woo P, et al., eds. Oxford Textbook of Rheumatology, vol. 1. Oxford, New York, Tokyo: Oxford University Press, 959-983 (1993).
Elting and Hubbell, "Unilateral frame distrction: proximal tibial valgus osteotomy for medial gonarthritis," *Contemp Orthop* 27(6):522-524 (1993).
Garrett, J. C., "Osteochondral allografts for reconstruction of articular defects of the knee," *Instr Course Lect* 47:517-522 (1998).
Hayes and Conway, "Evaluation of Articular Cartilage: Radiographic and Cross-Sectional Imaging Techniques," *Radiographics* 12:409-428 (1992).
Johnson, T.S., "In vivo contact kinematics of the knee joint: Advancing the point cluster technique," Ph.D. Thesis, University of Minnesota (1999).
Nizard, R.S., "Role of tibial osteotomy in the treatment of medical femorotibial osteoarthritis," *Rev Rhum Engl Ed* 65(7-9):443-446 (1998).
Steines, D., et al., Segmentation of osteoarthritic femoral cartilage using live wire, ISMRM Eight Scientific Meeting, Denver Colorado, 2000.
Yan, C.H., "Measuring changes in local volumetric bone density," new approaches to quantitative computed tomography, Ph.D. thesis, 1998, Dept. of Electrical Engineering, Stanford University.
U.S. Appl. No. 11/410,515, filed Apr. 25, 2009, Lang et al. Van der Linden et al. "Mar imaging of hyaline cartilage of 0.5 T: a quatitative and qualitative in virto evalution of three types of sequences." *Skeletal Radiol* 1998, 27:297-305.
Atheshian et al., "A B-Spline Least—Squares Surface-Fitting Method for Articular Surfaces of Diarthrodial Joints," *Journal of Biomechanical Engineering Division,* Transactions of the ASME, vol. 115, pp. 366-373, Nov. 1993.
Athesian et al., "Curvature Characteristics and Congruence of the Thumb Carpometacarpal Joint—Differences Between Female and Male Joints," *J. Biomechanics,* vol. 25, No. 6, pp. 591-607, 1992.
Athesian et al., "Quanitation of Articular Surface Topography and Cartilage Thickness in Knee Joints Using Stereogrammetry," *Biomechanics,* vol. 24, No. 8, pp. 761-776, 1991.
Borgefors, Gunilla, "Distance Transformations in Digital Images," Computer Vision, Graphics, and Image Processing 34, pp. 344-371, 1986.
Embrechts et al., "A Parallel Euclidean Distance Transformation Algorithm," *Vision and Image Understanding,* vol. 63, No. 1, pp. 15-26, 1996.
Kiryati, Nahum, "On Length Estimators, Distance Tranformations and Digital Lines in Three Dimensions," *Progress in Image Analysis and Processing III, Proc. of the 7th International Conference in Image Analysis and Processing, Capitolo, Italy,* pp. 22-29, 1993.
Ragnemalm, Ingemar, "The Euclidean Distance Transform in Arbitrary Dimensions," *Pattern Recognition Letters, North-Holland,* vol. 14, No. 11, pp. 883-888, Nov. 1993.
Warfield et al., "Automatic Segmentation of MRI of the Knee," *Medical Image Alanysis 4(1), Proc. ISMRM,* p. 563, 1998.
Herberhold C, et al., "An MR-Based Technique for Quantifying the Deformation of Articular Cartilage During Mechanical Loading in an Intact Cadaver Joint," *Magnetic Resonance in Medicine* 1998, 39(5): 843-850.
Adam D, et al. "MR Imaging of the Knee: Three-Dimensional Volume Imaging Combined with Fast Processing," *J Comput Asst Tomogr* Nov.-Dec. 1989; 13(6): 984-988.
Adams ME, et al. "Quanitative Imaging of Osteoarthritis." *Semin Arthritis Rheum* Jun. 1991; 20(6) Suppl. 2:26-39.
Ahmad CS, et al. "Biomechanical and Topographic Considerations for Autologous Osteochondral Grafting in the Knee." *Am J Sports Med* Mar-Apr. 2001; 29(2): 201-206.
Aro HT, et al. "Clinical Use of Bone Allografts." *Ann Med* 1993; 25: 405-412.
Beckmann N, et al. "Noninvasive 3D MR Microscopy as a Tool in Pharmacological Research: Application to a Model of Rheumatoid Arthritis." *Magn Reson Imaging* 1995; 13(7): 1013-1017.
Burgkart R, et al. "Magnetic Resonance Imaging-Based Assessment of Cartilage Loss in Severe Osteoarthritis." *Arth Rheum* Sep. 2001; 44(9): 2072-2077.
Castriota-Scanderberg A, et al. "Precision of Sonographic Measurement of Articular Cartilage: Inter-and Intraobserver Analysis." *Skeletal Radiol* 1996; 25: 545-549.
Clarke IC, et al. "Human Hip Joint Geometry and Hemiarthroplasty Selection." *The Hip.* C.V. Mosby, St. Louis; 1975. pp. 63-89.
Creamer P, et al. "Quantitative Magnetic Resonance Imaging of the Knee: A Method of Measuring Response to Intra-Articular Treatments." *Ann Rheum Dis* 1997; 56: 378-381.
Dupuy DE, et al. "Quantification of Articular Cartilage in the Knee with Three-Dimensional MR Imaging." *Acad Radiol* 1996; 3: 919-924.
Eckstein F, et al. "Accuracy of Cartilage Volume and Thickness Measurements with Magnetic Resonance Imaging." *Clin Orthop* 1998; 352: 137-148.
Eckstein F, et al. "Magnetic Resonance Chondro-Crassometry (MR CCM): A Method for Accurate Determination of Articular Cartilage Thickness?" *Magn Reson Med* 1996; 35: 89-96.
Eckstein F, et al. "The Influence of Geometry on the Stress Distribution in Joints—A Finite Element Analysis." *Anat Embryol* 1994; 189: 545-552.
Eckstein F, et al. "The Morphology of Articular Cartilage Assessed by Magnetic Resonance Imaging: Reproducibility and Anatomical Correlation." *Surg Radiol Anat* 1994; 16: 429-438.
Gerscovich EO. "A Radiologist's Guide to the Imaging in the Diagnosis and Treatment of Developmental Dysplasia of the Hip." *Skeletal Radiol* 1997; 26: 447-456.
Haubner M, et al. "A Non-Invasive Technique for 3-Dimensional Assessment of Articular Cartilage Thickness Based on MRI Part 2: Validation Using CT Arthrography." *Magn Reson Imaging* 1997; 15(7): 805-813.
Herrmann JM, et al. "High Resolution Imaging of Normal Osteoarthritic Cartilage with Optical Coherence Tomography." *J Rhematol* 1999; 26: 627-635.
Hughes SW, et al. "Technical Note: A Technique for Measuring the Surface Area of Articular Cartilage in Acetabular Fractures." *Br J Radiol* 1994; 67: 584-588.
Husmann O, et al. "Three-Dimensional Morphology of the Proximal Femur." *J Arthroplasty* Jun. 1997; 12(4): 444-450.
Ihara H. "Double-contrast CT Arthrography of the Cartilage of the Patellofemoral Joint." *Clin Orthop* Sep. 1985 ; 198: 50-55.
Iida H, et al. "Socket Location in Total Hip Replacement: Preoperative Computed Tomography and Computer Simulation," *Acta Orthop Scand* 1998; 59(1):1-5.
Jonsson K, et al. "Precision of Hyaline Cartilage Thickness Measurements." *Acta Radiol* 1992; 33(3): 234-239.
Kaneuji A, et al. "Three-Dimensional Morphological Analysis of the Proximal Femoral Canal, Using Computer-Aided Design System, in Japanese Patients with Osteoarthrosis of the Hip." *H Orthop Sci* 2000; 5(4): 361-368.
Karvonen RL, et al. "Articular Cartilage Defects of the Knee: Correlation Between Magnetic Resonance Imaging and Gross Pathology." *Ann Rheum Dis* 1990; 49: 672-675.
Koh HL, et al. "Visualization by Magnetic Resonance Imaging of Focal Cartilage Lesions in the Excised Mini-Pig Knee." *J Orthop Res* Jul. 1996; 14(4): 554-561.
Korkala O, et al. "Autogenous Osteoperiosteal Grafts in the Reconstruction of Full-Thickness Joint Surface Defects." *Int Orthop* 1991; 15(3): 233-237.
Kwak SD, et al. "Anatomy of Human Patellofemoral Joint Articular Cartilage: Surface Curvature Analysis." *J Orthop Res* 1997; 15: 468-42.
Lefebvre F, et al. "Automatic Three-Dimensional Reconstruction and Characterization of Articular Cartilage from High-Resolution Ultrasound Acquisitions." *Ultrasound Med Biol* Nov. 1998; 24(9): 1369-1381.

Lin CJ, et al. "Three-Dimensional Characteristics of Cartilagenous and Bony Components of Dysplastic Hips in Children: Three-Dimensional Computed Tomography Quantitative Analysis." *J Pediatr Orthop* 1997; 17: 152-157.
Marshall KW, et al. "Quantitation of Articular Cartilage Using Magnetic Resonance Imaging and Three-Dimensional Reconstruction." *J Orthop Res* 1995; 13: 814-823.
Mattila KT, et al. "Massive Osteoarticular Knee Allografts: Structural Changes Evaluated with Ct." *Radiology* 1995; 196: 657-660.
Milz S, et al. "The Thickness of the Subchondral Plate and Its Correlation with the Thickness of the Uncalcified Articular Cartilage in the Human Patell." *Anat Embryol* 1995 ; 192: 437-444.
Minas T. "Chondrocyte Implantation in the Repair of Chondral Lesions of the Knee: Economics and Quality of Life." *Am J Orthop* 1998 Biv; 27: 739-744.
Moussa M. "Rotational Malalignment and Femoral Torsion in Osteoarthritic Knees with Patellofemoral Joint Involvement: A CT Scan Study." *Clin Orthop* Jul. 1994; 304: 176-183.
Myers SL, et al. "Experimental Assessment by High Frequency Ultrasound of Articular Cartilage Thickness and Osteoarthritic Changes," *J Rheumatol* 1995; 22: 109-116.
Peterfy CG, et al. "Emerging Applications of Magnetic Resonance Imaging in the Evaluation of Articular Cartilage." *Radiol Clin North Am* Mar. 1996; 34(2): 195-213.
Rushfeldt PD, et al. "Improved Techniques for Measuring In Vitro the Geometry and Pressure Distribution in the Human Acetabulum-I. Ultrasonic Measurement of Acetabular Surfaces, Sphericity and Cartilage Thickness." *J Biomech* 1981; 14(4) 253-260.
Saied A, et al. "Assessment of Articular Cartilage and Subchondral Bone: Subtle and Progressive Changes in Experimental Osteoarthritis Using 50 MHz Echography In Vitro" *J Bone Miner Res* 1997; 12(9): 1378-1386.
Sittek H, et al. "Assessment of Normal Patellar Cartilage Volume Thickness Using MRI: and Analysis of Currently Available Pulse Sequences." *Skeletal Radiol* 1996; 25: 55-62.
Soslowsky LJ, et al. "Articular Geometry of the Glenohumeral Joint." *Clin Orthop* Dec. 1992; 181-190.
Tyler JA, et al. "Detection and Monitoring of Progressive Degeneration of Osteoarthritici Cartilage by MRI." *Acta Orthop Scand* 1995; 66 Suppl. 266: 130-138.
Van Leersum MD, et al. "Thickness of Patellofemoral Articular Cartilage as Measured on MR Imagin: Sequence Comparison of accuracy, reproducibility, and interobserver variation." *Skeletal Radiol* 1995; 24:431-435.
Waterton JC, et al. "Magnetic Resonance Methods for Measurement of Disease Progression in Rheumatoid Arthritis." *Magn Reson Imaging* 1993; 11: 1033-1038.
Watson PJ, et al. "MR Protocols for Imaging the Guinea Pig Knee." *Magn Reson Imaging* 1997; 15(8): 957-970.
Wayne JS, et al. "Finite Element Analyses of Repaired Articular Surfaces." *Proc Instn Mech Eng* 1991; 205(3): 155-162.
Chan et al., "Osteoarthritis of the knee: comparison of radiography, CT, and MR imaging to asse extent and severity," *AJR Am J Roentrgenol* 157(4):799-806, 1991.
Mills et al, "Magnetic resonance imaging of the knee: evaluation of meniscal disease," *Curr. Opin. Radiol* 4(6):77-82, 1992.
Mundinger et al., "Magnetic resonance tomography in the diagnosis of peripheral joints," *Schweiz Med. Wochenschr* 121(15):517-527, 1991.
Pilch et al,. "Assessment of cartilage volume in the femorotbial joint with magnetic resonance imaging and 3D computer reconstruction," *J. Rheumatol.*21(12):2307-2321, 1994.
Bashir et al., "Validation of Gadolinium—Enhanced MRI of GAG Measurement in Human Cartilage".
Butterworth et al., Depts of Biomedical Engineering, Medicine, Neurolory, & Center for Nuclear Imaging Research, University of Alabama at Birmingham, USA.
Gandy et al., "One-year longitudinal study of femoral cartilage lesions in knee arthritis", 1999.

ASSESSING THE CONDITION OF A JOINT AND DEVISING TREATMENT

Matter enclosed in heavy brackets [ ] appears in the original patent but forms no part of this reissue specification; matter printed in italics indicates the additions made by reissue.

This application claims the benefit of U.S. Provisional Application Ser. No. 60/112,989, filed Dec. 16, 1998 and is a [continuation] *continuation-in-part* of PCT/US99/30265, filed Dec. 16, 1999, both of which are herein incorporated by reference.

This invention was supported in part by a National Institute of Health Grant No. PAR-97-014, and the government may have rights in this invention.

BACKGROUND OF THE INVENTION

1. Field of Invention

This invention relates to assessing the condition of a joint and the use of the assessment in aiding in prevention of damage to the joint or treatment of diseased cartilage in the joint.

2. Background

Osteoarthritis is the most common condition to affect human joints as well as a frequent cause of locomotor pain and disability. More particularly, osteoarthritis (OA) of the knee occurs in a substantial portion of the population over the age of fifty.

In spite of its societal impact and prevalence, however, there is a paucity of information on the factors that cause osteoarthritis to progress more rapidly in some individuals and not in others. Previously considered a "wear and tear" degenerative disease with little opportunity for therapeutic intervention, osteoarthritis is now increasingly viewed as a dynamic process with potential for new pharmacologic and surgical treatment modalites such as cartilage transplantation, osteochondral allo- or autografting, osteotomies and tibial corticotomies with angular distraction.

However, the appropriate deployment and selection of treatment interventions for OA is dependent on the development of better methods for the assessment of the condition of a patient's joint and the degeneration process.

There is, therefore, a need for improved methods for examining the factors that influence as well as quantification of the progression of the disease.

Magnetic resonance imaging (MRI) is an accurate non-invasive imaging technique for visualization of articular cartilage in osteoarthritis, particularly in knees. However, current MRI techniques cannot provide information on the relationship between the location of the cartilage loss and variations in the load bearing areas during the walking cycle. This information is important since it has been shown that dynamic loads during walking are related to the progression of knee OA. Thus, the ability to locate cartilage defects or areas of cartilage thinning relative to the load bearing areas of the knee could be valuable in evaluating factors influencing the progression of osteoarthritis.

REFERENCES

1. Alexander E J: Estimating the motion of bones from markers on the skin [Doctoral Dissertation]. University of Illinois at Chicago; 1998.

2. Alexander E J, Andriacchi T P: Correcting for deformation in skin-based marker systems. Proceedings of the 3rd. Annual Gait and Clinical Movement Analysis Meeting, San Diego, Calif., 1998.
3. Alexander E J, Andriacchi T P: Internal to external correspondence in the analysis of lower limb bone motion. Proceedings of the 1999 ASME Summer Bioengineering Conference, Big Sky, Mont., 1999.
4. Alexander E J, Andriacchi T P: State estimation theory in human movement analysis. Proceedings of the 1998 ASME International Mechanical Engineering Congress, 1998.
5. Alexander E J, Andriacchi T P, Lang P K: Dynamic functional imaging of the musculoskeletal system. ASME Winter International Congress and Exposition, Nashville, Tenn., 1999.
6. Alexander E J, Andriacchi T P, Naylor D L: Optimization techniques for skin deformation correction. International Symposium on 3-D Human Movement Conference, Chattanooga, Tenn., 1998.
7. Allen P R, Denham R A, Swan A V: Late degenerative changes after meniscectomy: factors affecting the knee after operations. J Bone Joint Surg 1984; 66B: 666-671.
8. Alley M T, Shifrin R Y, Pelc N J, Herfkens R J: Ultrafast contrast-enhanced three dimensional MR angiography: state of the art. Radiographics 1998; 18: 273-285.
9. Andriacchi T P: Dynamics of knee malalignment. Orthop Clin North Am 1994; 25: 395-403.
10. Andriacchi T P, Alexander E J, Toney M K, Dyrby C O, Sum J: A point cluster method for in vivo motion analysis: applied to a study of knee kinematics. J Biomech Eng 1998; 120(12): 743-749.
11. Andriacchi T P, Lang P, Alexander E, Hurwitz D: Methods for evaluating the progression of osteoarthritis. J Rehab Res Develop 2000; 37, 2: 163-170.
12. Andriacchi T P, Sen K, Toney M K, Yoder D: New developments in musculoskeletal testing. Proceedings of the Canadian Society of Biomechanics, 1994.
13. Andriacchi T P, Strickland A B: Gait analysis as a tool to assess joint kinetics biomechanics of normal and pathological human articulating joints. Nijhoff, Series E 1985; 93: 83-102.
14. Andriacchi T P, Toney M K: In vivo measurement of six-degrees-of-freedom knee movement during functional testing. Transactions of the Orthopedic Research Society 1995: 698.
15. Beaulieu C F, Hodge D K, Bergman A G: Glenohumeral relationships during physiological shoulder motion and stress testing: initial experience with open MRI and active scan-plane registration. Radiology 1999: accepted for publication.
16. Beaulieu C F, Hodge D K, Thabit G, Lang P K, Bergman A G: Dynamic imaging of glenohumeral instability with open MRI. Int. Society for Magnetic Resonance in Medicine, Sydney, Australia, 1998.
17. Benedetti M G, Cappozzo A: Anatomical landmark definition and identification in computer aided movement analysis in a rehabilitation context II (Internal Report). U Degli Studi La Sapienza 1994: 1-31.
18. Bergman A G, Beaulieu C F, Pearle A D, et al.: Joint motion: assessment by upright interactive dynamic near-real time MR imaging. Radiological Society of North America, 83rd Scientific Assembly and Annual Meeting, Chicago, Ill., 1997.
19. Biswal S, Hastie T, Andriacchi T, Bergman G, Dillingham M F, Lang P: The rate of progressive cartilage loss at the knee is dependent on the location of the lesion: a longitudinal MRI study in 43 patients. Arthritis&Rheumatism 2000: submitted for publication.

20. Bobic V: Arthoscopic osteochondral autograft transplantation in anterior cruciate ligament reconstruction: a preliminary clinical study. Knee Surg Sports Traumatol Arthrosc 1996; 3 (4): 262-264.
21. Boe S, Hansen H: Arthroscopic partial meniscectomy in patients aged over 50. J Bone Joint Surg 1986; 68B: 707.
22. Bregler C, Hertzmann A, Biermann H: Recovering non-rigid 3D shape from image streams. Proc. IEEE Conference on Computer Vision and Pattern Recognition 2000: in press.
23. Brittberg M, Lindahl A, Homminga G, Nilsson A, lsaksson O, Peterson L: A critical analysis of cartilage repair. Acta Orthop Scand 1997; 68 (2)186-191.
24. Brittberg M, Lindahl A, Nilsson A, Ohlsson C, Isaksson O, Peterson L: Treatment of deep cartilage defects in the knee with autologous chondrocyte transplantation. N Engl J Med 1994; 331 (14): 889-895.
25. Broderick L S, Turner D A, Renfrew D L, Schnitzer T J, Huff J P, Harris C: Severity of articular cartilage abnormality in patients with osteoarthritis: evaluation with fast spin-echo MR vs arthroscopy. AJR 1994; 162: 99-103.
26. Butts K, Pauly J M, Kerr A B, Bergman A G, Beaulieu C F: Real-Time MR imaging of joint motion on an open MR imaging scanner. Radiological Society of North America, 83rd Scientific Assembly and Annual Meeting, Chicago, Ill., 1997.
27. Cohen Z A, McCarthy D M, Kwak, S D, Legrand P, Fogarasi F, Ciaccio E J, Ateshian G A: Knee cartilage topography, thickness, and contact areas from MRI: in-vitro calibration and in-vivo measurements. Osteoarthritis and Cartilage 1999; 7: 95-109.
28. Daniel. B, Butts K, Glover G, Herfkens R: Breast cancer: gadolinium-enhanced MR imaging with a 0.5T open imager and three-point Dixon technique. Radiology 1998; 207 (1): 183-190.
29. Disler D G: Fat-suppressed three-dimensional spoiled gradient-recalled MR imaging: assessment of articular and physeal hyaline cartilage. AJR 1997; 169: 1117-1123.
30. Disler D G, McCauley T R, Kelman C G, et al.: Fat-suppressed three-dimensional spoiled gradient-echo MR imaging of hyaline cartilage defects in the knee: comparison with standard MR imaging and arthroscopy. AJR 1996; 167: 127-132.
31. Disler D G, McCauley T R, Wirth C R, Fuchs M D: Detection of knee hyaline cartilage defects using fat-suppressed three-dimensnional spoiled gradient-echo MR imaging: comparison with standard MR imaging and correlation with arthrosocpy. AJR 1995; 165: 377-382.
32. Doherty M, Hutton C, Bayliss M T: Osteoarthritis. In: Maddison P J, Isenberg D A, Woo P, et al., eds. Oxford Textbook of Rheumatology, vol 1. Oxford, N.Y., Tokyo: Oxford University Press, 1993; 959-983.
33. Dougados M, Gueguen A, Nguyen M, et al.: Longitudinal radiologic evaluation of osteoarthritis of the knee. J Rheumatol 1992; 19: 378-384.
34. Du Y P, Parker D L, Davis W L: Vessel enhancement filtering in three-dimensional MR angiography. J Magn Res Imaging 1995; 5: 151-157.
35. Du Y P, Parker D L, Davis W L, Cao G: Reduction of partial-volume artifacts with zero-filled interpolation in three-dimensional MR angiography. J Magn Res Imaging 1994; 4: 733-741.
36. Dumoulin C L, Souza S P, Darrow R D: Real-time position monitoring of invasive devices using magnetic resonance. Magn Reson Med 1993; 29: 411-5.
37. Dyrby C O: The three-dimensional kinematics of knee joint motion: functional differences in two populations [Master's Thesis]. University of Illinois at Chicago; 1998.
38. Eckstein F, Westhoff J, Sittek H, et al.: In vivo reproducibility of three-dimensional cartilage volume and thickness measurements with MR imaging. AJR 1998; 170(3): 593-597.
39. Elting J J, Hubbell J C: Unilateral frame distraction: proximal tibial valgus osteotomy for medial gonarthritis. Contemp Orthop 1993; 27(6): 522-524.
40. Falcão A X, Udupa J K, Samarasekera S, Sharma S: User-steered image segmentation paradigms: Live wire and live lane. Graphical Models and Image Processing 1998; 60: 233-260.
41. Felson D T, Zhang Y, Anthony J M, Naimark A, Anderson J J: Weight loss reduces the risk for symptomatic knee osteoarthritis in women: the Framingham study. Ann Intern Med 1992; 116: 535-539.
42. Garrett J C: Osteochondral allografts for reconstruction of articular defects of the knee. Instr Course Lect 1998; 47: 517-522.
43. Ghosh S, Newitt D C, Majumdar S: Watershed segmentation of high resolution articular cartilage image. International Society for Magnetic Resonance in Medicine, Philadelphia, 1999.
44. Gouraud H: Continuous shading of curved surfaces. IEEE Trans on Computers 1971; C-20(6).
45. Gray A: Modern Differential Geometry of Curves and Surfaces. 1993: CRC Press, Inc.
46. Hargreaves B A, Gold G E, Conolly S M, Nishimura D G: Technical considerations for DEFT imaging. International Society for Magnetic Resonance in Medicine, Sydney, Australia, Apr. 17-24, 1998.
47. Hargreaves B A, Gold G E, Lang P K, Bergman G, Conolly S M, Nishimura D G: Imaging of articular cartilage using driven equilibrium. International Society for Magnetic Resonane in Medicine, Sydney, Australia, Apr. 17-24, 1998.
48. Hayes C, Conway W: Evaluation of articular cartilage: radiographic and cross-sectional imaging techniques. Radiographics 1992; 12: 409-428.
49. Henkelman R M, Stanisz G, Kim J, Bronskill M: Anisotropy of NMR properties of tissues. Magn Res Med 1994; 32: 592-601.
50. Hoppenfeld S, Huton R: Physical Examination of the Knee. In: Hoppenfeld S. ed. Physical Examination of the Spine and Extremities: Appleton-Century-Crofts/Prentice-Hall, 1976; 171-196.
51. Hyhlik-Durr A, Faber S, Burgkart R, et al.: Precision of tibial cartilage morphometry with a coronal water-excitation MR sequence. European Radiology 2000; 10 (2): 297-303.
52. Irarrazabal P, Nishimura D G: Fast three-dimensional magnetic resonance imaging. Mag Res Med 1995; 33: 656-662.
53. Johnson F, Leitl S, Waugh W: The distribution of load across the knee. A comparison of static and dynamic measurements. J Bone Joint Surg 1980; 62B: 346-349.
54. Johnson T S: In vivo contact kinematics of the knee joint: Advancing the point cluster technique. Ph.D. thesis, University of Minnesota 1999.
55. Johnson T S, Andriacchi T P, Laurent M: Development of a knee wear method based on prosthetic in vivo slip velocity. Transactions of the Orthopedic Research Society, 46th Annual Meeting, March, 2000.

56. LaFortune M A, Cavanagh P R, Sommer H J, Kalenak A: Three dimensional kinematics of the human knee during walking. J. Biomechanics 1992; 25: 347-357.
57. Lang P, Alexander E, Andriacchi T: Funcional joint imaging: a new technique integrating MRI and biomotion studies. International Society for Magnetic Resonance in Medicine, Denver, Apr. 18, 2000-Apr. 24, 2000, 2000.
58. Lang P. Biswal S, Dillingham M, Bergman G, Hastie T, Andriacchi T: Risk factors for progression of cartilage loss: a longitudinal MRI study. European Society of Musculoskeletal Radiology, 6th Annual Meeting, Edinburgh, Scotland, 1999.
59. Lang P, Hargreaves B A, Gold G, et al.; Cartilage imaging: comparison of driven equilibrium with gradient-echo, SPGR, and fast spin-echo sequences. International Society for Magnetic Resonance in Medicine, Sydney, Australia, Apr. 17-24, 1998.
60. Ledingham J, Regan M, Jones A, Doherty M: Factors affecting radiographic progression of knee osteoarthritis. Ann Rheum Dis 1995; 54: 53-58.
61. Lorensen W E, Cline H E: Marching cubes: a high resolution 3d surface construction algorithm. Comput to Graph 1987; 21: 163-169.
62. Losch A, Eckstein F, Haubner M, Englmeier K H: A non-invasive technique for 3-dimensional assessment of articular cartilage thickness based on MRI part 1: development of a computational method. Magn Res Imaging 1997; 15, 7: 795-804.
63. Lu T W, O'Connor J J: Bone position estimation from skin marker co-ordinates using globals optimisation with joint constraints. J Biomechanics 1999; 32: 129-134.
64. Lucchetti L, Cappozzo A, Cappello A, Della Croce U: Skin movement artefact assessment and compensation in the estimation of knee joint kinematics. J Biomechanics 1998; 31: 977-984.
65. Lynch J A, Zaim S, Zhao Stork A, Genant H K: Cartilage segmentation of 3D MRI scans of the osteoarthritic knee combining user knowledge and active contours. Proc. SPIE 3979 Medical Imaging, San Diego, February 2000.
66. Maki J H, Johnson G A, Cofer G P, MacFall J R: SNR improvement in NMR microscopy using DEFT. J Mag Res 1988.
67. Meyer C H, Pauly J M, Macovski A, Nishimura D G: Simultaneous spatial and spectral selective excitation. Magn Res Med 1990; 15: 287-304.
68. Mollica Q, Leonardi W, Longo G, Travaglianti G: Surgical treatment of arthritic varus knee by tibial corticotomy and angular distraction with an external fixator. Ital J Orthop Traumatol 1992; 18 (1): 17-23.
69. Nizard R S: Role of tibial osteotomy in the treatment of medial femorotibial osteoarthritis. Rev Rhum Engl Ed 1998; 65 (7-9): 443-446.
70. Noll D C, Nishimura D, Macovski A: Homodyne detection in magnetic resonance imaging. IEEE Trans Med Imag10 1991; 10 (2): 154-163.
71. Ogilvie-Harris D J, Fitsialos D P: Arthroscopic management of the degenerative knee. Arthroscopy 1991; 7: 151-157.
72. Pearle A, Bergman A G, Daniels B, et al.: Use of an external MR-tracking coil for active scan plane registration during dynamic musculoskeletal MR imaging in a vertically open MRT unit. American Roentgen Ray Society, San Francisco, Calif., 1998.
73. Pearle A D, Daniel B L, Bergman A G: Joint motion in an open MR unit using MR tracking. JMRI 1999; 10 (10): 1566-1576.
74. Peterfy C, van Dijke C, Lu Y, et al.: Quantification of the volume of articular cartilage in the metacarpophalangeal joints of the hand: accuracy and precision of three-dimensional MR imaging. AJR 1995; 165: 371-375.
75. Peterfy C G, Majumdar S, Lang P, van Dijke. C, Sack K, Genant H K: MR imaging of the arthritic knee: improved discrimination of cartilage, synovium, and effusion with pulsed saturation transfer and fat-suppressed T1-weighted sequences. Radiology 1994; 191(2): 413-419.
76. Peterfy C G, van Dijke C F, Janzen D L, et al.: Quantification of articular cartilage in the knee with pulsed saturation transfer subtraction and fat-suppressed MR imaging: optimization and validation. Radiology 1994; 192(2): 485-491.
77. Piplani M A, Disler D G, McCauley T R, Holmes T J, Cousins J P: Articular cartilage volume in the knee: semi-automated determination from three-dimensional reformations of MR images. Radiology 1996; 198: 855-859.
78. Potter H G, Linklater J M, Allen AA, Hannafin J A, Haas S B: Magnetic resonance imaging of articular cartilage in the knee: an evaluation with use of fast-spin-echo imaging. J Bone Joint Surg 1998; 80-A(9): 1276-1284.
79. Prodromos C C, Andriacchi T P, Galante J O: A relationship between gait and clinical changes following high tibial osteotomy. J Bone Joint Surg 1985; 67A: 1188-1194.
80. Radin E L, Burr D B, Caterson B, Fyhrie D, Brown T D, Boyd R D: Mechanical determinants of osteoarthrosis. Sem Arthr Rheum 1991; 21(3): 12-21.
81. Radin E L, Burr D B, Fyhrie D: Characteristics of joint loading as it applies to osteoarthrosis. In: Mow V C, Woo S-Y, Ratcliffe T, eds. Symposium on Biomechanics of Diarthrodial Joints, vol 2. New York, N.Y.: Springer-Verlag, 1990; 437-451.
82. Recht M P, Piraino D W, Paletta G A, Schils J P, Belhobek G H: Accuracy of fat-suppressed three-dimensional spoiled gradient-echo FLASH MR imaging in the detection of patellofemoral articular cartilage abnormalities. Radiology 1996; 198: 209-212.
83. Recht M P, Resnick D: MR imaging of articular cartilage: current status and future directions. AJR 1994; 163: 283-290.
84. Ritter M A, Faris P M, Keating E M, Meding J B: Postoperative alignment of total knee replacement. Clin Orthop 1994; 299: 153-156.
85. Saito T, Toriwaki J-I: New algorithms for Euclidean distance transformation of an n-dimensional digitized picture with applications. Pattern Recognition 1994; 27 (11): 1551-1565.
86. Schipplein O D, Andriacchi T P: Interaction between active and passive knee stabilizers during level walking. J Orthop Res 1991; 9: 113-119.
87. Schouten J S A G, van den Ouweland F A, Valkenburg H A: A 12 year follow up study in the general population on prognostic factors of cartilage loss in osteoarthritis of the knee. Ann Rheum Dis 1992; 51: 932-937.
88. Sharif M, George E, Shepstone L, et al.: Serum hyaluronic acid level as a predictor of disease progression in osteoarhritis of the knee. Arthritis Rheum 1995; 38: 760-767.
89. Sharma L, D. E. H, Thonar E J M A, et al.: Knee adduction moment, serum hyaluronic acid level, and disease severity in medial tibiofemoral osteoarthritis. Arthritis and Rheumatism 1998; 41(7): 1233-40.
90. Shoup R R, Becker E D: The driven equilibrium Fourier transform NMR technique: an experimental study. J Mag Res 1972; 8.
91. Slemenda C, Mazzuca S, Brandt K, Katz B: Lower extremity lean tissue mass and strength predict increases in pain and in functional impairment in knee osteoarthritis. Arthritis Rheum 1996; 39(suppl): S212.

92. Slemenda C, Mazzuca S, Brandt K, Katz B: Lower extremity strength, lean tissue mass and bone density in progression of knee osteoarthritis. Arthritis Rheunm 1996; 39(suppl): S169.

93. Solloway S, Hutchinson C E, Waterton J C, Taylor C J: The use of active shape models for making thickness measurements of articular cartilage from MR images. Mag Res Med 1997; 37:943-952.

94. Spoor C W, Veldpas F E: Rigid body motion calculated from spatial coordinates of markers. J Biomechanics 1980; 13: 391-393.

95. Stammberger T, Eckstein F, Englmeier K H, Reiser M: Determination of 3D cartilage thickness data from MR imaging: computational method and reproducibility in the living. Mag Res Med 1999; 41: 529-536.

96. Stammberger T, Eckstein F, Michaelis M, Englmeier K H, Reiser M: Interobserver reproducibility of quantitative cartilage measurements: Comparison of B-spline snakes and manual segmentation. Mag Res Imaging 1999; 17:1033-1042.

97. Steines D, Berger F, Cheng C, Napel S, Lang P: 3D thickness maps of articular cartilage for quantitative assessment of osteoarthritis. To be presented at ACR 64th Annual Scientific Meeting, Philadelphia, October 2000.

98. Steins D, Cheng C, Wong A, Berger F, Napel S, Lang P: Segmentation of osteoarthritic femoral cartilage from MR images. CARS-Computer-Assisted Radiology and Surgery, 578-583, San Francisco, 2000.

99. Steines D, Napel S, Lang P: Measuring volume of articular cartilage defects in osteoarthritis using MRI. To be presented at ACR 64th Annual Scientific Meeting, Philadelphia, October 2000.

100. Stevenson S, Dannucci G A, Sharkey N A, Pool R R: The fate of articular cartilage after transplantation of fresh and cryopreserved tissue-antigen-matched and mis-matched osteochondral allografts in dogs. J Bone Joint Surg 1989; 71 (9): 1297-1307.

101. Tieschky M, Faber S, Haubner M, et al.: Repeatability of patellar cartilage thickness patterns in the living, using a fat-suppressed magnetic resonance imaging sequence with short acquisition time and three-dimensional data processing. J Orthop Res 1997; 15(6): 808-813.

102. Tomasi C, Kanade T: Shape and motion from image streams under orthography—a factorization method. Proc Nat Acad Sci 1993; 90(21): 9795-9802.

103. Tsai J, Ashjaee S, Adalsteinsson E, et al.: Application of a flexible loop-gap resonator for MR imaging of articular cartilage at 3.0T. International Society for Magnetic Resonance in Medicine, Denver, Apr. 18, 2000-Apr. 24, 2000, 2000.

104. Wang J W, Kuo K N, Andriacchi T P, Galante J O: The influence of walking mechanics and time on the results of proximal tibial osteotomy. J Bone Joint Surg 1990; 72A: 905-909.

105. Waterton J C, Solloway S, Foster J E, Keen M C, Gandy S, Middleton B J, Maciewicz R A, Watt I, Dieppe P A, Taylor C J: Diurnal variation in the femoral articular cartilage of the knee in young adult humans. Mag Res Med, 2000, 43: 126-132.

106. Woolf S D, Chesnick F, Frank J, Lim K, Balaban R: Magnetization transfer contrast: MR imaging of the knee. Radiology 1991; 179: 623-628.

107. Worring M, Smeulders A W M: Digital curvature estimation. CVGIP: Image Understanding, 1993. 58(3): p. 366-382.

108. Yan C H: Measuring changes in local volumetric bone density: new approaches to quantitative computed tomography, Ph.D. thesis, 1998, Dept. of Electrical Engineering, Stanford University 109. Yao L, Gentili A, Thomas A: Incidental magnetization transfer contrast in fast spin-echo imaging of cartilage. J Magn Reson Imaging 1996; 6 (1): 180-184.

110. Yao L, Sinha S, Seeger L: MR imaging of joints: analytic optimization of GRE techniques at 1.5 T. AJR 1992; 158 (2): 339-345.

111. Yasuda K, T. M, Tsuchida T, Kameda K: A 10 to 15 year follow up observation of high tibial osteotomy in medial compartment osteoarthritis. Clin Orthop 1992; 282: 186-195.

112. Kass M, Witkin A, Terzopoulos D: Snakes: Active contour models. Int J Comput Vision 1988; 1:321-331

113. Falcao A X, Udupa J K, Samarasekera S, Sharma S, Hirsch B E, Lotufo R A: User-steered image segmentation paradigms: Live wire and live lane. GMIP 1998; 60, 233-260

114. Steines, D., et al., Segmentation of osteoarthritic femoral cartilage using live wire, ISMRM Eight Scientific Meeting, Denver Colo., 2000

SUMMARY OF THE INVENTION

This invention relates to assessing the condition of a joint of a mammal, particularly a human subject, using the assessment to treat and monitor the subject as needed for cartilage degeneration problems. While the numerous aspects of the invention are useful for joints generally, they are particularly suited for dealing with the human knee. Some aspects related the static images and degeneration patterns of a cartilage, while others relate to the interaction of such images and patterns to provide a better means of assessing the condition of a cartilage.

One aspect of this invention is a method for assessing the condition of a cartilage. The method comprises obtaining an image of a cartilage, (preferably a magnetic resonance image), converting the image to a three-dimensional degeneration pattern, and evaluating the degree of degeneration in a volume of interest of the cartilage. By performing this method at an initial time T, and a later time T2, one can determine the change in the volume of interest and evaluate what steps to take for treatment.

Another aspect of this invention is a method of estimating the loss of cartilage in a joint. The method comprises obtaining a three-dimensional map of the cartilage at an initial time and calculating the thickness or regional volume of a region thought to contain degenerated cartilage so mapped at the initial time, obtaining a three-dimensional map of the cartilage at a later time, and calculating the thickness or regional volume of the region thought to contain degenerated cartilage so mapped at the later time, and determining the loss in thickness or regional volume of the cartilage between the later and initial times. The 3D map may be a thickness map, a biochemical map or a combination.

Another aspect of the invention is a method for assessing the condition of cartilage in a joint of a human, which method comprises electronically transferring an electronically-generated image of a cartilage of the joint from a transferring device to a receiving device located distant from the transferring device; receiving the transferred image at the distant location; converting the transferred image to a degeneration pattern of the cartilage; and transmitting the degeneration pattern to a site for analysis.

Another aspect of the invention is a method for determining the volume of cartilage loss in a region of a cartilage defect of a cartilage in joint of a mammal. The method comprises (a) determining the thickness, $D_N$, of the normal cartilage near the cartilage defect; (b) obtaining the thickness of the cartilage defect, $D_D$, of the region; (c) subtracting $D_D$ from $D_N$ to give the thickness of the cartilage loss, $D_L$; and (d) multiplying the $D_L$ value times the area of the cartilage defect, $A_D$, to give the volume of cartilage loss.

Still another aspect of the-invention is a method of estimating the change of a region of cartilage in a joint of a mammal over time. The method comprises (a) estimating the width or area or volume of a region of cartilage at an initial time $T_1$, (b) estimating the width or area or volume of the region of cartilage at a later time $T_2$, and (c) determining the change in the width or area or volume of the region of cartilage between the initial and the later times.

Still another aspect of the invention is a method of estimating the loss of cartilage in a joint. The method comprises (a) defining a 3D object coordinate system of the joint at an initial time, $T_1$; (b) identifying a region of a cartilage defect within the 3D object coordinate system; (c) defining a volume of interest around the region of the cartilage defect whereby the volume of interest is larger than the region of cartilage defect, but does not encompass the entire articular cartilage; (d) defining the 3D object coordinate system of the joint at a second timepoint, $T_2$; (e) placing the identically-sized volume of interest into the 3D object coordinate system at timepoint $T_2$ using the object coordinates of the volume of interest at timepoint $T_1$; (f) and measuring any differences in cartilage volume within the volume of interest between timepoints $T_1$ and $T_2$.

Another aspect of this invention is a method for providing a biochemically-based map of joint cartilage. The method comprises measuring a detectable biochemical component throughout the cartilage, determining the relative amounts of the biochemical component throughout the cartilage; mapping the amounts of the biochemical component through the cartilage; and determining the areas of cartilage deficit by identifying the areas having an altered amount of the biochemical component present.

Once a map is obtained, it can be used in assessing the condition of a cartilage at an initial time and over a time period. Thus, the biochemical map may be used in the method aspects of the invention in a manner similar to the cartilage thickness map.

Another aspect of this invention is a method for assessing the condition of cartilage in a joint from a distant location. The method comprises electronically transferring an electronically-generated image of a cartilage of the joint from a transferring device to a receiving device located distant from the transferring device; receiving the transferred image at the distant location; converting the transferred image to a degeneration pattern of the cartilage; and transmitting the degeneration pattern to a site for analysis.

Another aspect of the invention is a kit for aiding in assessing the condition of cartilage in a joint of a mammal, which kit comprises a software program, which when installed and executed on a computer reads a cartilage degeneration pattern presented in a standard graphics format and produces a computer readout showing a cartilage thickness map of the degenerated cartilage.

Another aspect of this invention is a method for assessing the condition of a subject's cartilage in a joint, the method comprises obtaining a three dimensional biochemical representation of the cartilage, obtaining a morphological representation of the cartilage, and merging the two representations, and simultaneously displaying the merged representations on a medium. The merged representations are then used to assess the condition of a cartilage, estimate the loss of cartilage in a joint, determining the volume of cartilage loss in a region of cartilage defect, or estimating the change of a region of cartilage at a particular point in time or over a period of time.

A method for correlating cartilage image data, bone image data, and opto-electrical image data for the assessment of the condition of a joint, which method comprises (a) obtaining the bone image data of the joint with a set of skin reference markers positioned in externally near the joint, (b) obtaining the opto-electrical image data of the joint with a set of skin reference markers positioned in the same manner as (a), and (c) using the skin reference markers to correlate the images obtained in (a) and (b) with each other, wherein each skin reference marker is detectable in the bone data and the opto-electrical data. The method also can be used to further evaluate cartilage image data that is obtained using a similarly positioned set of skin reference markers.

Another aspect of the invention is a skin reference marker that comprises (a) a material detectable by an imaging technique; (b) a container for holding the material, (c) a material that causes the container to adhere to the skin of a human, and (d) a reflective material placed on the surface of the container.

Another aspect of the invention is a biochemical map of a cartilage that comprises a three-dimensional representation of the distribution of the amount of the biochemical component throughout the cartilage.

Another aspect of the invention is a method for providing a biochemically-based map of joint cartilage of a mammal, wherein the joint comprises cartilage and associated bones on either side of the joint, which method comprises (a) measuring a detectable biochemical component throughout the cartilage; (b) determining the relative amounts of the biochemical component throughout the cartilage; (c) mapping th e amounts of the biochemical component in three dimensions through the cartilage; and (d) determining the areas of abnormal joint cartilage by identifying the areas having altered amounts of the biochemical component present.

Another aspect of the invention is a method for deriving the motion of bones about a joint from markers placed on the skin, which method comprises (a) placing at least three external markers on the patient's limb segments surrounding the joint, (b) registering the location of each marker on the patient's limb while the patient is standing completely still and while moving the limb, (c) calculating the principal axis, principal moments and deformation of rigidity of the cluster of markers, and (d) calculating a correction to the artifact induced by the motion of the skin markers relative to the underlying bone.

Another aspect of the invention is a system for assessing the condition of cartilage in a joint of a human, which system comprises (a) a device for electronically transferring a cartilage degeneration pattern for the joint to a receiving device located distant from the transferring device; (b) a device for receiving the cartilage degeneration pattern at the remote location; (c) a database accessible at the remote location for generating a movement pattern for the joint of the human wherein the database includes a collection of movement patterns of human joints, which patterns are organized and can be accessed by reference to characteristics such as type of joint, gender, age, height, weight, bone size, type of movement, and distance of movement; (d) a device for generating a movement pattern that most closely approximates a movement pattern for the human patient based on the characteristics of the human patient; (e) a device for correlating the movement pattern with the cartilage degeneration pattern; and (f) a device for transmitting the correlated movement pattern with the cartilage degeneration pattern back to the source of the cartilage degeneration pattern.

A method for assessing the condition of the knee joint of a human patient, wherein the knee joint comprises cartilage and associated bones on either side of the joint, which method comprises (a) obtaining the patient's magnetic resonance imaging (MRI) data of the knee showing at least the bones on either side of the joint, (b) segmenting the MRI data from step (a), (c) generating a geometrical representation of the bone of the joint from the segmented MRI data, (d) assessing the patient's gait to determine the load pattern or the cartilage contact pattern of the articular cartilage in the joint during the gait assessment, and (e) correlating the load pattern or cartilage contact pattern obtained in step (d) with the geometrical representation obtained in step (c).

Another aspect of the invention is a method of assessing the rate of degeneration of cartilage in the joint of a mammal, wherein the joint comprises cartilage and the bones on either side of the cartilage, which method comprises (a) obtaining a cartilage degeneration pattern of the joint that shows an area of greater than normal degeneration, (b) obtaining a movement pattern of the joint that shows where the opposing cartilage surfaces contact, (c) comparing the cartilage degeneration pattern with the movement pattern of the joint, and (d) determining if the movement pattern shows contact of one cartilage surface with a portion of the opposing cartilage surface showing greater than normal degeneration in the cartilage degeneration pattern.

Another aspect of the invention is a method for monitoring the treatment of a degenerative joint condition in a mammal, wherein the joint comprises cartilage and accompanying bones on either side of the joint, which method comprises (a) comparing the movement pattern of the joint with the cartilage degeneration pattern of the joint; (b) determining the relationship between the movement pattern and the cartilage degeneration pattern; (c) treating the mammal to minimize further degeneration of the joint condition; and (d) monitoring the treatment to the mammal. Still another aspect of the invention is a method of assessing the condition of a joint in a mammal, wherein the joint comprises cartilage and accompanying bones on either side of the joint, which method comprises (a) comparing the movement pattern of the joint with the cartilage degeneration pattern of the joint; and (b) determining the relationship between the movement pattern and the cartilage degeneration pattern Other aspects of the invention may be apparent upon further reading the specification and claims of the patent application.

BRIEF DESCRIPTION OF THE DRAWINGS

In the accompanying drawings:

FIG. 8A has the subject in a supine position and FIG. 8B has the subject in an upright position.

FIG. 9B is a 2D cartilage thickness map demonstrating abrupt decrease in cartilage thickness in the area of the defect (arrows). The Δ thickness between the neighboring pixels can be use to define the borders of the cartilage defect. Note defused cartilage thinning in the area enclosed by the asterisks (*).

FIG. 10A is baseline with a knee in neutral position. FIG. 10B is a follow-up with knee and external rotation with a 3D view that is the identical to the one used in 10A but the difference in knee rotation is apparent. In FIG. 10C, transformation and re-registration of Scan B to the object coordinate system of Scan A shows the anatomic match to A is excellent.

SPECIFIC DESCRIPTION

Overview

Figure 1:
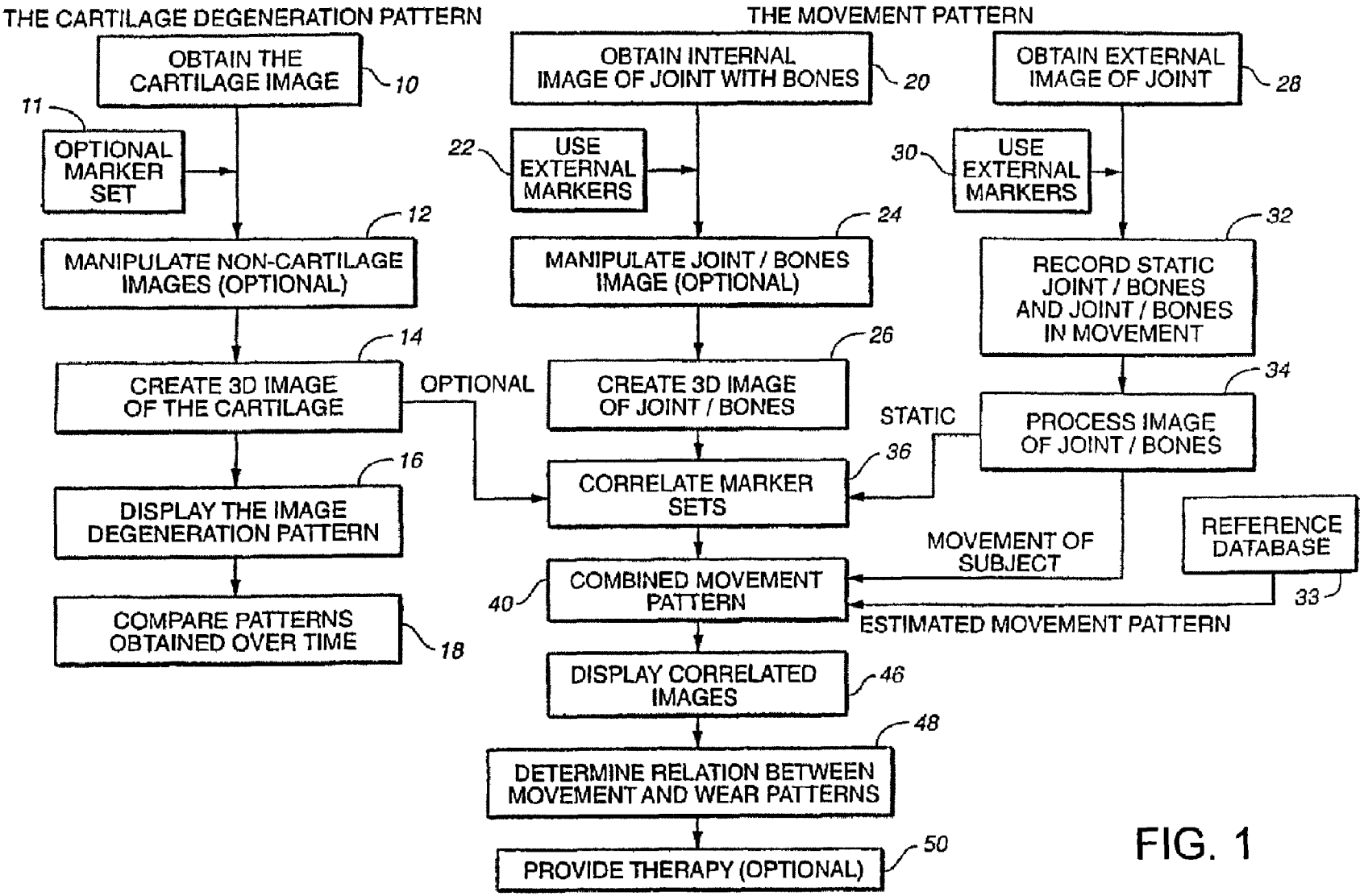
FIG. 1 shows an overview schematic representation of some aspects of the invention of this application.

FIG. 1 is a schematic overview of some of the various aspects of the invention. While a complete description of the many aspects of the invention is found in the specification and claims, the schematic overview gives some of the broad aspects of the invention.

This invention relates to assessing the condition of a joint in a mammal. One aspect is a method for such an assessment. The assessment can be done using internal images, or maps, of the cartilage alone or in combination with a movement pattern of the joint. If used alone, a map obtained at an initial time is compared with a map obtained at a later time to provide a view of the change in cartilage over time. Another aspect is a method is comparing the movement pattern for a joint of a subject being studied with the cartilage degeneration pattern of the subject, then determining the relationship between the movement pattern and the degeneration pattern. If, in determining the relationship between the two patterns, one finds that the movement pattern has caused the degeneration pattern or will continue to adversely affect the degeneration pattern, therapy can be prescribed to minimize the adverse effects, such as further degeneration or inflammation.

In overview, some of the systems and methods of this invention are illustrated by the flow chart in the attached FIG. 1. FIG. 1 is based on the full range of processes, preferably applied to a knee and surrounding cartilage.

In FIG. 1, the first step 10 represents obtaining an image of the cartilage itself. This is typically achieved using MRI techniques to take an image of the entire knee and then, optionally, manipulating (e.g., "subtracting out" or "extracting") the non-cartilage images as shown in step 12. Non-cartilage images typically come from bone and fluid. Preferably, the MRI is taken using external markers to provide reference points to the MRI image (step 11). If the cartilage is imaged with a 2D MRI acquisition technique, the resulting stack of 2D images so obtained can be combined into a 3D image, as indicated in step 14. A preferred alternative is to use 3D MRI acquisition techniques to acquire a 3D image directly. In either case, the same "non-cartilage image extraction techniques referred to in step 12 can be used.

With a full 3D image captured, various "maps" or displays of the cartilage can be constructed to give a cartilage degeneration pattern. This is represented by step 16. One such display can, for example, be a color-coding of a displayed image to reflect the thickness for the cartilage. This will allow easy visual identification of actual or potential defects in the cartilage.

Together with or independently of the cartilage imaging, and as represented by parallel step 20, a 3D image of the knee joint is taken, again preferably using MRI. Many of the same techniques as applied in steps 10 to 14 are used to do this. However, as illustrated by sub-step 22, it is useful to define and register a skin-external frame of reference around the joint. This is achieved by placing fiduciary markers on the skin around the outside of the knee (step 22) prior to taking the image.

In addition to an image extraction technique (as described above in step 12), an image is manipulated to enhance the image of the position of the markers (step 24). The resulting manipulated image is used to give a 3D image of the joint and associated bones (step 26). With the markers in place, and as shown by step 30, an additional set of markers is placed on the skin along the outside of the leg, and an external image of the limb is obtained. Using at least two cameras, images are then taken of the subject in a static state. In addition, images are also taken of the subject while moving. This is shown collectively by step 32. The images obtained are then processed to relate the movement of the skin relative to the bone. In addition, certain calculations are performed, for example, the center of mass is calculated. These manipulations are shown in Step 34. Further, as the fiduciary markers are still in place during the video image capture, a correlation between the fiduciary and the addi- tional set of markers can be made. This is shown in step 36.

Once this marker-to-marker correlation is made, the static 3D image of the joint (with associated fiduciary markers) and the movement images of the leg bones (also with fiduciary markers in place) can be combined. The fiduciary markers, therefore, serve as baseline references. The combination (step 40) of 3D cartilage image (from step 14), 3D knee joint image (step 26), and the moving leg co-ordinates (step 34) will, after appropriate corrections, result in a displayable, 3D motion image of the joint moving as per step 46.

The moving images, showing the contact areas of the knee joint can be used in conjunction with the various "maps" or displays generated at step 16 to provide a visual indication of potential or actual cartilage defects and help in determining their relation between movement and degeneration patterns. This is shown in step 48.

Furthermore, as the various images are supported by actual mathematical quantification, real measurements (such as cartilage thickness) can be taken and compared with later or earlier measurements and/or imaging. This allows the tracking of the progression of a defect, or conversely, continued tracking of healthy cartilage. This aids a health worker in providing therapy for the patients. The method allows monitoring and evaluation of remedial actions as well as possible treatment prescriptions.

Thus, this invention discloses, for example, a method to examine the relationship between articular cartilage morphology and the functional load bearing areas of a knee joint measured during movement. The method includes enhanced imaging techniques to reconstruct the volumetric and biochemical parameters of the articular cartilage in three dimensions; and a method for in vivo kinematic measurements of the knee. The kinematic measurement permits direct in vivo measurements of complete six-degrees of freedom motion of the femur or the tibia or associated bones during normal activities. This permits the study of load bearing of articular cartilage during movement. In particular, this method can aid in locating cartilage defects relative to the changing load bearing areas of the knee joint during daily activities. While the various aspects of the invention are useful in mammals generally, they are particularly useful for human patients.

Obtaining the Cartilage Degeneration Pattern

Imaging Articular Cartilage

In general, the joint of a patient is that place of union, more or less movable, between two or more bones. A joint comprises cartilage and other elements such as the accompanying bones on either side of the joint, fluid, and other anatomical elements. Joints arc classified into three general morphological types: fibrous, cartilaginous, and synovial. This invention is particularly useful for assessing synovial joints, particularly the knee.

In obtaining an image of the cartilage of a joint in a mammal, a number of internal imaging techniques known in the art are useful for electronically generating a cartilage image. These include magnetic resonance imaging (MRI), computed tomography scanning (CT, also known as computerized axial tomography or CAT), and ultrasound imaging techniques. Others may be apparent to one of skill in the art. MRI techniques are preferred.

MRI, with its superior soft tissue contrast, is the best technique available for assessing tissue and its defects, for example articular cartilage and cartilage lesions, to obtain a cartilage degeneration can provide morphologic information about the area of damage. Specifically, changes such as fissuring, partial or full thickness cartilage loss, and signal changes within residual cartilage can be detected.

The reason MR imaging techniques are particularly suitable for cartilage is because they can provide accurate assessment of cartilage thickness, demonstrate internal cartilage signal changes, evaluate the subchondral bone for signal abnormalities, and demonstrate morphologic changes of the cartilage surface.

MRI provides several important advantages over other techniques in this invention. One advantage is good contrast between cartilage, bone, joint fluid, ligaments, and muscle in order to facilitate the delineation and segmentation of the data sets. Another is the coverage of the entire region of interest in a single scan within acceptable acquisition times. For a brief discussion of the basic MRI principles and techniques, see MRI Basic Principles and Applications, Second Edition, Mark A. Brown and Richard C. Semelka, Wiley-Liss, Inc. (1999).

MRI employs pulse sequences that allow for better contrast of different parts of the area being imaged. Different pulse sequences are better fitted for visualization of different anatomic areas, for example, hyaline cartilage or joint fluid. More than one pulse sequence can be employed at the same time. A brief discussion of different types of pulse sequences is provided below.

High Resolution 3D MRI Pulse Sequences

Routine MRI pulse sequences available for imaging tissue, such as cartilage, include conventional T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement, (RARE) imaging, gradient echo acquisition in the steady state, (GRASS), and driven equilibrium Fourier transform (DEFT) imaging. As these imaging techniques are well known to one of skill in the art, e.g. someone having an advanced degree in imaging technology, each is discussed only generally hereinafter. While each technique is useful for obtaining a cartilage degeneration pattern, some are better than others.

Conventional T1 and T2-Weighted Spin-Echo Imaging

Conventional T1 and T2-weighted MRI depicts articular cartilage, and can demonstrate defects and gross morphologic changes. T1-weighted images show excellent intra-substance anatomic detail of hyaline cartilage. However, T1-weighted imaging does not show significant contrast between joint effusions and the cartilage surface, making surface irregularities difficult to detect. T2-weighted imaging demonstrates joint effusions and thus surface cartilage abnormalities, but since some components of cartilage have relatively short T2 relaxation times, these are not as well depicted as other preferred imaging.

Gradient-Recalled Echo Imaging

Gradient-recalled echo imaging has 3D capability and ability to provide high resolution images with relatively short scan times. Fat suppressed 3D spoiled gradient echo (FS-3D-SPGR) imaging has been shown to be more sensitive than standard MR imaging for the detection of hyaline cartilage defects in the knee.

Magnetization Transfer Contrast Imaging

Cartilage, as well as other ordered tissues, demonstrate the effects of magnetization transfer. Magnetization transfer imaging can be used to separate articular cartilage from adjacent joint fluid and inflamed synovium.

Fast Spin-Echo Imaging

Fast spin-echo imaging is another useful pulse sequence to evaluate articular cartilage. Incidental magnetization transfer contrast contributes to the signal characteristics of articular cartilage on fast spin-echo images and can enhance the contrast between cartilage and joint fluid. Sensitivity and specificity of fast spin-echo imaging have been reported to be 87% and 94% in a study with arthroscopic correlation.

Contrast Enhanced Imaging

The use of gadolinium for imaging of articular cartilage has been applied in several different forms. Direct magnetic resonance (MR) arthrography, wherein a dilute solution containing gadolinium is injected directly into the joint, improves contrast between cartilage and the arthrographic fluid. Indirect MR arthrography, with a less invasive intravenous injection, can also been applied. Gadolinium enhanced imaging has the potential to monitor glycosaminoglycan content within the cartilage, which may have implications for longitudinal evaluations of injured cartilage.

Driven Equilibrium Fourier Transform

Another 3D imaging method that has been developed is based on the driven equilibrium fourier transform (DEFT) pulse sequence (U.S. Pat. No. 5,671,741), and is specifically designed for cartilage imaging. DEFT provides an effective tradeoff between T2/T1 weighting and spin density contrast that delineates the structures of interest in the knee. Contrast-to-noise ratio between cartilage and joint fluid is greater with DEFT than with spoiled gradient echo (SPGR). DEFT is an alternative approach to SPGR. DEFT contrast is very well suited to imaging articular cartilage. Synovial fluid is high in signal intensity, and articular cartilage intermediate in signal intensity. Bone is dark, and lipids are suppressed using a fat saturation pulse. Hence, cartilage is easily distinguished from all of the adjacent tissues based on signal intensity alone, which will greatly aid segmentation and subsequent volume calculations.

Figure 2:
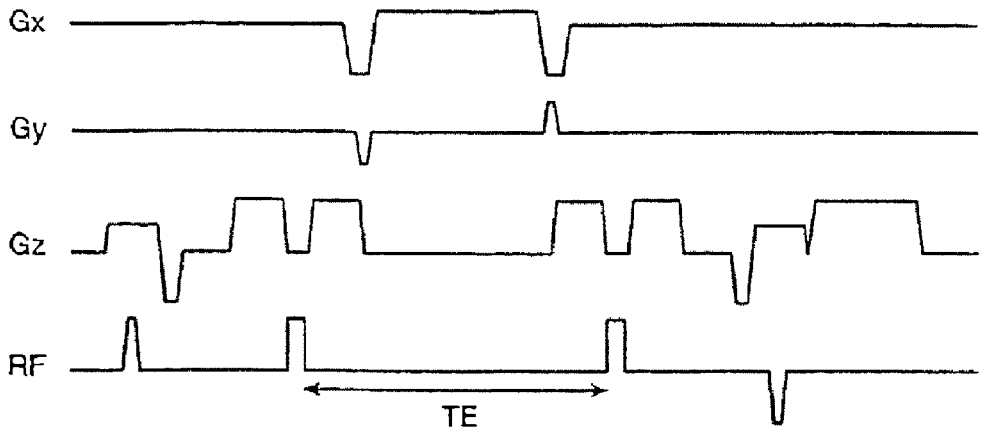
FIG. 2 shows a DEFT pulse sequence.
Figure 3A:
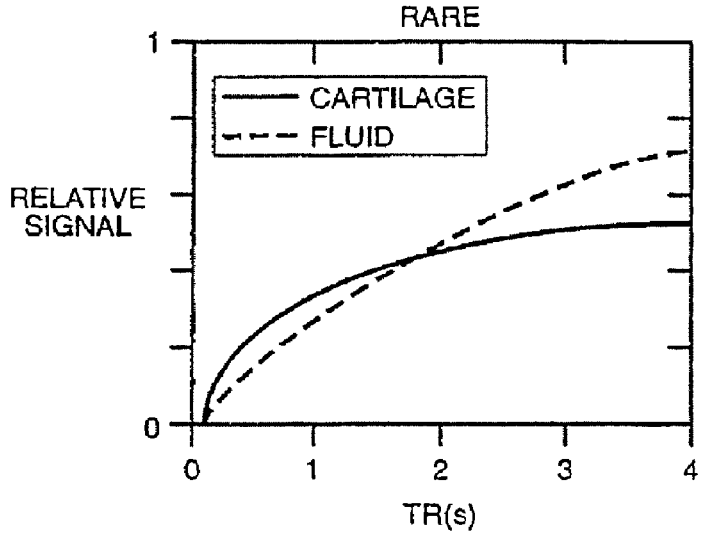
FIG. 3 shows the signal levels for cartilage and synovial fluid with RARE and DEFT pulse sequences, both TE=14 miliseconds.
Figure 3B:
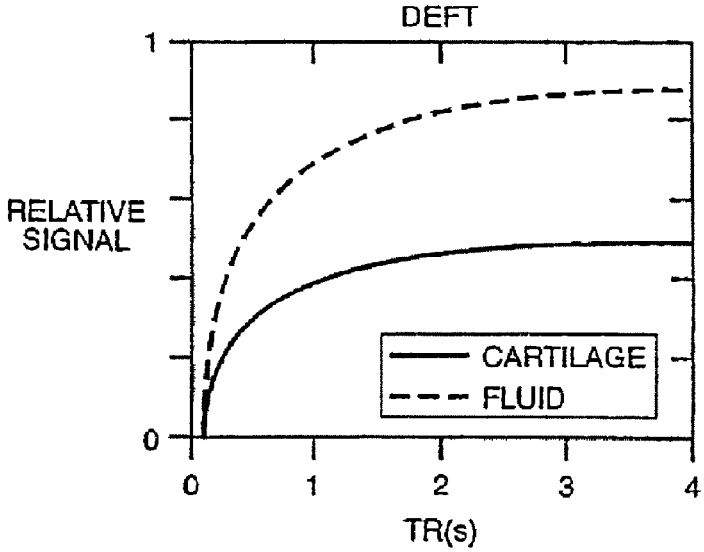

The basic DEFT pulse sequence is shown in FIG. 2. A conventional spin echo pulse sequence was followed by an additional refocusing pulse to form another echo, and then a reversed, negated, excitation pulse to return any residual magnetization to the +z axis. This preserved the magnetization of longer T2 species, such as synovial fluid. Typical MRI parameters for cartilage are a T1-relaxation time of 900 Milliseconds (ms) and a T2-relaxation time of 40 ms, while synovial fluid has a T1-relaxation time of 3000 ms and a T2-relaxation time of 200 ms. In addition, synovial fluid has a 30% greater proton density than cartilage. The signal levels of cartilage and synovial fluid were plotted in FIG. 3 for a RARE pulse sequence and for DEFT, and show that DEFT maintains excellent contrast for any relaxation time (TR). It achieves this contrast while maintaining a signal-to-noise ratio (SNR) efficiency (SNR/($T_{acquisition}$)) that is equal to or better than other methods with much lower contrast, such as T1-weighted GRASS.

DEFT was compared with a fast spin-echo (FSE), a gradient-echo (GRE), and a spoiled gradient-echo (SPGR) sequence with parameters similar to the ones published by Disler et al. The patella IS was scanned in 10 normal volunteer knees using a 1.5T whole-body system (GE Signa) with a 3 inch surface coil. All images were acquired with field of view (FOV) 10×10 cm, matrix 256×256 elements, slice thickness 4 mm using fat-saturation. DEFT (400/15 [TRITE in msec], 2 NEX (number of excitations), FSE (3500/15, echo train length [ETL] 8, 2 NEX (number of excitations), FSE (3500/15, ETL 4, 2 NEX), GRE (400/20, 30°, 2 NEX), and SPGR (50/15, 30° [flip angle], 2 NEX) images were obtained. Contrast-to-noise ratios (CNR) between cartilage and joint fluid were calculated as:

$$CNR=|(SI_{Joint\ Fluid}-SI_{cartilage})/SI_{Background\ Noise}| \quad \text{[Eq. 1]}$$

Contrast (C) between cartilage and joint fluid was calculated as:

$$C=|[(SI_{Joint\ Fluid}-SI_{cartilage})/SI_{Joint\ Fluid}]\times 100| \quad \text{[Eq. 2]}$$

Figure 4:
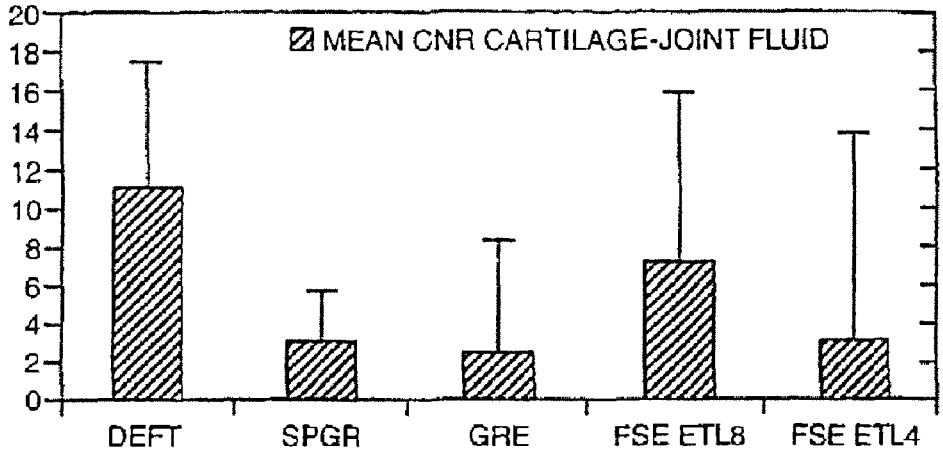
FIG. 4 shows the mean contrast to noise ratio (CNR) of cartilage to joint fluid for various MRI pulse sequences.
Figure 5:
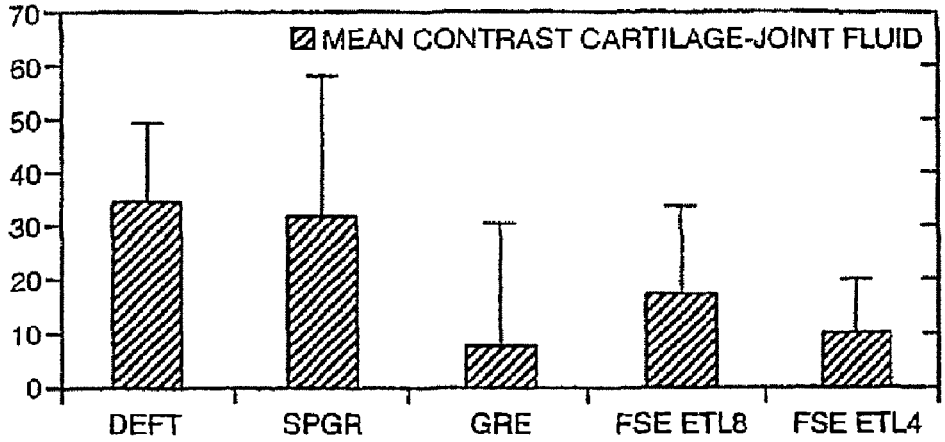
FIG. 5 shows the mean contrast for cartilage and joint fluid for various MRI pulse sequences.

In the equations SI is signal intensity. DEFT demonstrated greater contrast-to-noise ratio and contrast between cartilage and joint fluid than SPGR, GRE, and FSE sequences (FIGS. 4 & 5). Cartilage had intermediate signal intensity with DEFT, while joint fluid was high in signal intensity. The difference in CNR between DEFT and SPGR was statistically significant ($p<0.001$). Cartilage morphology, i.e. cartilage layers, were consistently best delineated with the DEFT sequence. At the resolution used in this study, FSE sequences suffered from image blurring. Blurring was improved with ETL 4 when compared to ETL8; nonetheless, even with ETL 4, cartilage morphology seen on FSE images was inferior to the DEFT sequence. In light of these results, DEFT imaging is a preferred MRI technique.

Another Application of DEFT

Figure 6:
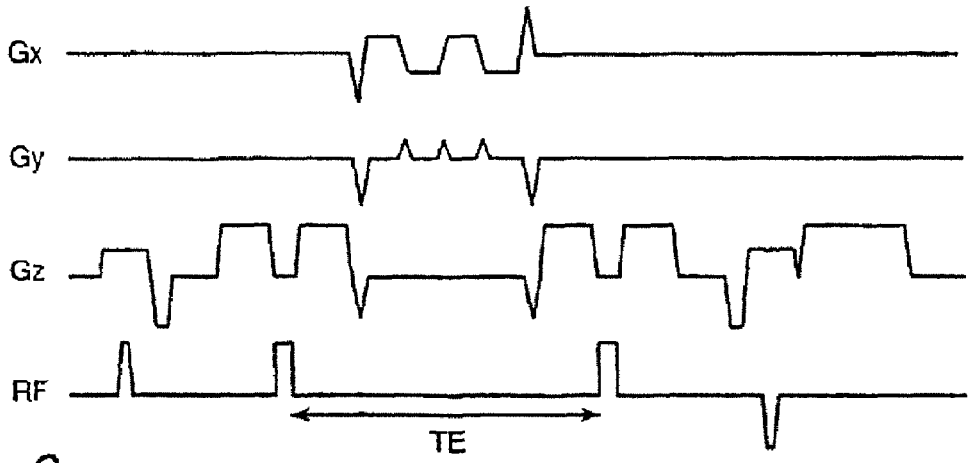
FIG. 6 shows a DEFT acquisition using non-selective refocusing pulses to maximize the SNR efficiency and a partial K-Echo-Plainer acquisition gradients in order to minimize the required scan time for 3D volume.

DEFT was combined with a partial k-space echo-planar data acquisition. This pulse sequence is illustrated in FIG. 6 above. A slab selective pulse in z defines the imaging volume, which is then resolved with phase-encoding gradients in the y and z axes, and an oscillating EPI gradient in the x axis.

Figure 7:
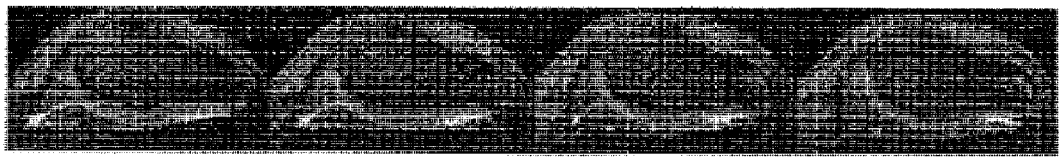
FIG. 7 shows four sample images acquired with a DEFT pulse sequence combined with a partial K- Echo-Plainer acquisition in order to provide efficient 3D coverage.

Example images acquired with this approach are shown in FIG. 7. This case was optimized for resolution, in order to image the patellar cartilage. The EPI readout acquired 5 echoes for each DEFT sequence. Partial k-space acquisition collected only 60% of the data along the x-axis. Correction for the missing data was performed using a homodyne reconstruction. The image matrix was 192×192×32, with a resolution of 0.5×0.5×2.5 mm, resulting in a 10×10×8 cm FOV. The echo time TE was 22 ms, and the TR was 400 ms. Fat was suppressed with a fat presaturation pulse. The total scan time for this acquisition was 5 minutes.

Additional image studies that can be performed using this approach may require greater spatial coverage, but one can permit slightly less spatial resolution, and a longer scan time similar to the one used with the 3D SPGR approach. If one relaxes the resolution to 0.75×0.75×1.5 mm, and doubles the z slab thickness and z phase encodes, the result will be a FOV of 15×15×16 cm, and a total scan time of approximately 15 minutes, which exactly fits the desired scan protocol. Similar to the 3D SPGR acquisition, one can acquire a first 3D DEFT scan in the sagittal plane with fat saturation. The 3D DEFT acquisition can then be repeated without fat saturation using the identical parameters and slice coordinates used during the previous acquisition with fat saturation. The resultant non-fat-saturated 3D DEFT images can be used for 3D rendering of the femoral and tibial bone contours.

In summary, Driven Equilibrium Fourier Transform is a pulse sequence preferred for cartilage imaging that provides higher contrast-to-noise ratios and contrast between cartilage and joint fluid than SPGR, GRE, and FSE sequences. Cartilage morphology is better delineated with DEFT sequences than with SPGR, GRE, and FSE images. The combination of high anatomic detail and high cartilage-joint fluid CNR and contrast may render this sequence particularly useful for longitudinal studies of cartilage in patients with osteoarthritis.

A Representative Example of MR Imaging is described below:

A MR image can be performed using a whole body magnet operating at a field strength of 1.5 T (GE Signa, for example, equipped with the GE SR-120 high speed gradients [2.2 Gauss/cm in 184 μsec risetimes]). Prior to MR imaging, external markers filled with Gd-DTPA (Magnevist®, Berlex Inc., Wayne, N.J.) doped water (T1relaxation time approximately 1.0 sec) can be applied to the skin around the knee joint and optionally at the same positions used for gait analysis in a biomotion laboratory (discussed below). The external markers can be included in the field of view of all imaging studies. Patients can be placed in the scanner in supine position. After an axial scout sequence, coronal and sagittal T1-weighted images of the femur can be acquired using the body coil (spin-echo, TR=500 msec, TE=15 msec, 1 excitation (NEX), matrix 256×128 elements, field of view (FOV) 48 cm, slice thickness 7 mm, interslice spacing 1 mm). The scanner table can then be moved to obtain coronal and sagittal images of the knee joint and tibia using the same sequence parameters. These T1-weighted scans can be employed to identify axes through the femur and tibia which can be used later for defining the geometry of the knee joint. The knee can then be placed in the knee coil with the joint space located in the center of the coil. The knee can be secured in the coil with padding. Additionally, the foot and ankle region can be secured in neutral position to the scanner table using adhesive tape in order to minimize motion artifacts. A rapid scout scan can be acquired in the axial plane using a gradient echo sequence (GRASS, 2D Fourier Transform (2DFT), TR=50 msec, TE=10 msec, flip angle 40°, 1 excitation (NEX), matrix 256×128 elements, field of view (FOV) 24 cm, slice thickness 7 mm, interslice spacing 3 mm). This scout scan can be used to demonstrate the position of the knee joint space in the coil and to prescribe all subsequent high resolution imaging sequences centered over the joint space. Additionally, using the graphic, image based sequence prescription mode provided with the scanner software, the scout scan can help to ensure that all external markers around the knee joint are included in the field of view of the high resolution cartilage sensitive MR sequences.

Figure 8A:
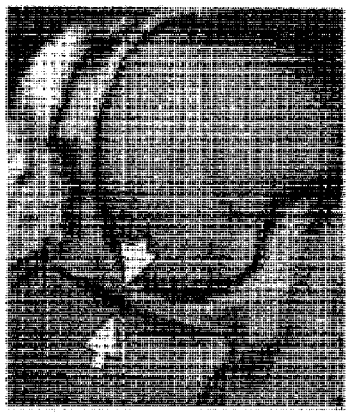
FIGS. 8A and 8B show a 3-point Dixon GRE image of the articular cartilage of medial femorotibial compartment in a normal 35-year old volunteer.
Figure 8B:
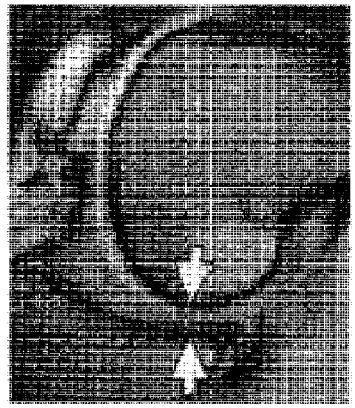
Figure 9A:
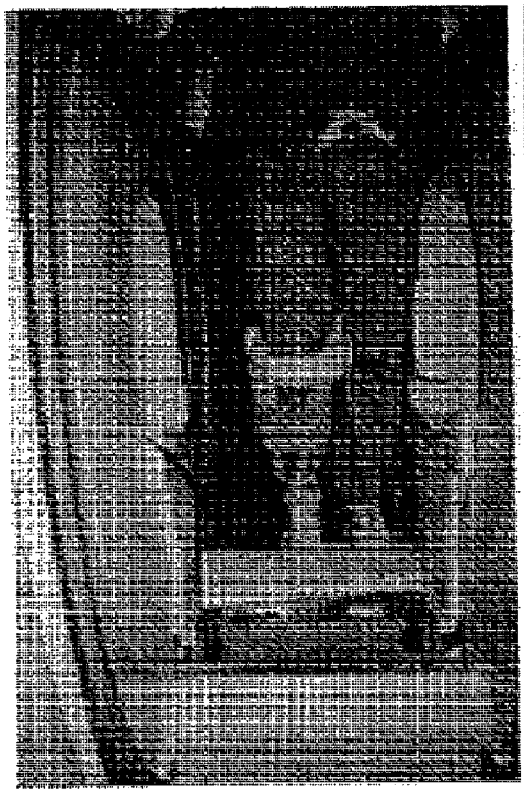
FIGS. 9A-9C show patient position and application of imaging coil and tracker coil for kinetic MR imaging of the knee. Patient is in upright weight-bearing position for active flexion and extension study of the knee.
Figure 9B:
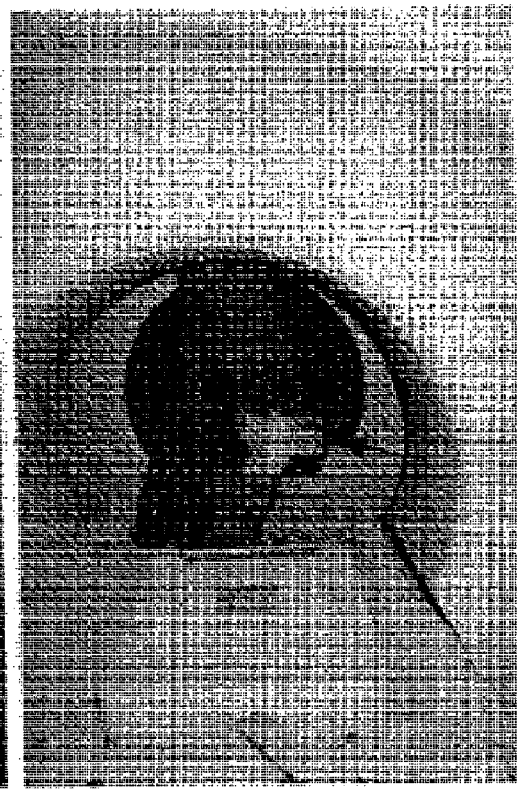
Figure 9C:
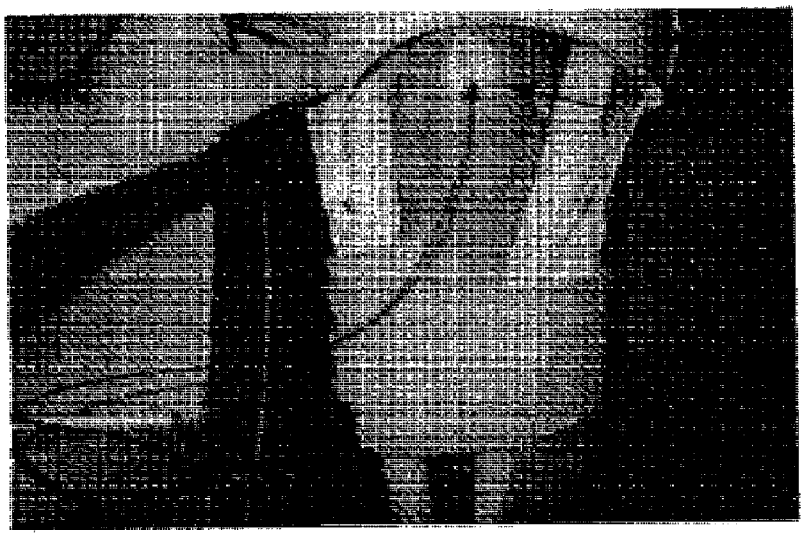

There are several issues to consider in obtaining a good image. One issue is good contrast between cartilage, bone, joint fluid, ligaments, and muscle in order to facilitate the delineation and segmentation of the data sets. Another is the coverage of both condyles of the knee in a single scan within acceptable acquisition times. In addition, if there are external markers, these must be visualized. One way to address these issues is to use a three-dimensional spoiled gradient-echo sequence in the sagittal plane with the following parameters (SPGR, 3DFT, fat-saturated, TR=60 msec, TE=5 msec, flip angle 40°, 1 excitation (NEX), matrix 256×160 elements rectangular FOV 16×12 cm, slice thickness 1.3 mm, 128 slices, acquisition time approximately 15 min). Using these parameters, one can obtain complete coverage across the knee joint and the external markers both in mediolateral and anteroposterior direction while achieving good spatial resolution and contrast-to-noise ratios between cartilage, bone and joint fluid (FIGS. 8 and 9). The fat-saturated 3D SPGR sequences can be used for rendering the cartilage in three dimensions (see description below). The 3D SPGR sequence can then be repeated in the sagittal plane without fat saturation using the identical parameters and slice coordinates used during the previous acquisition with fat saturation. The resultant non-fat-saturated 3D SPGR images demonstrate good contrast between low signal intensity cortical bone and high signal intensity bone marrow thereby facilitating 3D rendering of the femoral and tibial bone contours. It is to be understood that this approach is representative only and should not be viewed as limiting in any way.

Volumes of Interest (VOI)

The invention allows a health practitioner to determine cartilage loss in a reproducible fashion and thus follow the progression of a cartilage defect over time.

In one embodiment of the invention, one can use a 2D or a 3D surface detection technique to extract the surface of the joint, e.g. the femoral condyles, on both baseline and follow-up scans. For example, a T1-weighted spin-echo sequence can be used for surfaces extraction of the femoral condyles. The T1-weighted spin-echo sequence provides high contrast between low signal intensity cortical bone and high signal intensity fatty marrow. For detection of the surface of the femoral condyles, a step-by-step problem solving procedure, i.e., an algorithm, can convolve a data set with a 3D kernel to locate the maximum gradient location. The maximum gradient location corresponds to the zero crossing of a spatial location. When the kernel is designed properly, then there will be only one zero crossing in the mask. Thus, that zero crossing is the surface. This operation is preferably three-dimensional rather than two-dimensional. The surface of the joint, e.g. the femoral condyles, on the baseline scan can be registered in an object coordinate system A. The surface of the joint, e.g. the femoral condyles, on the follow-up scan can be registered in an object coordinate system B. Once these surfaces have been defined, a transformation B to B' can be performed that best matches B' with A. Such transformations can, for example, be performed using a Levenberg Marquardt technique. Alternatively, the transformations and matching can be applied to the cartilage only. The same transformation can be applied to the cartilage sensitive images on the follow-up scan in order to match the cartilage surfaces.

Using the 3D surface registration of the joint on the baseline scan and resultant object coordinate system A, one can place volumes of interest over the area of a cartilage defect seen on the cartilage sensitive images. For example, in the knee joint, the size of the targeted volumes of interest can be selected to exceed that of the cartilage defect in anteroposterior and mediolateral direction, e.g. by 0.5 to 1 cm. If the defect is located high on the femoral condyle or in the trochlear region, the targeted VOI can be chosen so that its size exceeds that of the cartilage defect in supero-inferior and mediolateral direction. The third dimension of the targeted VOI (parallel to the surface normal of the cartilage) can be fixed, for example at 1 cm. VOI size and placement can be manual or automatic on the baseline study. Once the targeted VOI has been placed on the image using visual or automated computer control, the 3D coordinates of the targeted VOI relative to the 3D contour of the joint and object coordinate system A can be registered and saved. On follow-up studies, e.g. scans inadvertently obtained with slightly different patient position, the 3D surface of the joint is registered to match the orientation of the baseline scan and the targeted VOI is then automatically placed on the joint using object coordinate system B' and the coordinates saved on the baseline study. Cartilage volume within the targeted VOI on baseline and follow-up studies can, for example, be determined using standard thresholding and seed growing techniques.

Reference Markers

When obtaining the MR images for use in this invention, whether the MRI is of cartilage or of bone, external reference markers can be placed on the skin around the joint of the subject being imaged. The external marker can be designed not only to show up in the MRI, but also to show up if an external image of the joint is obtained. The importance and value of such unique reference markers will be discussed in more detail hereinafter.

Thus, one embodiment of the invention is a skin reference marker that can be used in the assessment of the condition of a joint of a human. Multiple skin reference markers can be placed upon one or more limbs of a patient prior to internal imaging and external imaging. Each skin reference marker comprises a material detectable by an imaging technique, a container for the material in which the container preferably has multiple surfaces, a means for affixing the container to the skin (e.g. an adhesive placed on at least one surface of the container in an amount sufficient to adhere the container to the skin of a human), and a reflective material (preferably retro-reflective) placed on another surface of the container located away from the adhesive. Several imaging techniques can be used that are able to detect the marker. For example, magnetic resonance imaging is preferred, but, ultrasound, or X-ray are also useful. In the case of X-ray, further manipulations must be performed in which multiple X-ray images are assimilated by a computer into a 2 dimensional cross-sectional image called a Computed Tomography (CT) Scan. The material detectable by an imaging can be either in a liquid form or a solid form. The material can be any imaging contrast agent or solution, e.g. a paramagnetic material. The material can be a lanthanide, such as one belonging to the yttrium group of rare earth metals. More specifically, the material can be gadolinium. The shape of the container can be any shape allowing it to be placed on the skin of a human. For example, it can be cubical, spherical, elliptical, discoid or cylindrical. The size of the container can be any size, but optimally a size allowing it to be recorded by an imaging machine. The longest dimension of the container can be up to 5.0 cm, but preferably is about 0.25 to 2.0 cm. The reflective or retro-reflective material can be any material that is able to reflect light directly back to the source of the light so that the position of the reference marker is captured by the opto-electrical recording means, e.g. a video camera. 3M Corporation makes several retro-reflective materials.

Manipulating Images

Once a magnetic resonance image is obtained, it can be manipulated to improve the image by reducing unwanted, non-cartilage images.

Segmentation

To prepare the data set for 3D rendering, the cartilage can be segmented image by image using a signal-intensity-based threshold combined with a seed growing technique. The femoral, tibial, and patellar cartilage can be segmented separately based on the fat-saturated 3D SPGR or 3D DEFT sequence. Manual disarticulation can be performed by outlining the cartilage contour in areas where the signal intensity of the articular cartilage is similar to that of adjacent structures. The contours of the femoral, tibial, and patellar bone can be segmented separately using the non-fat-saturated 3D SPGR or 3D DEFT sequence. Segmentation software can allow for manual editing of cartilage thickness maps and cartilage defects detected using the above embodiments. In this fashion, the operator can correct erroneous detection of cartilage defects in areas where the cartilage may be naturally thinner. Such software includes seed-growing algorithms and active-contour algorithms that are run on standard PC's. A sharp interface is present between the high signal intensity bone marrow and the low signal intensity cortical bone thereby facilitating seed growing. Fat-saturated and non-fat-saturated 3D sequences can be acquired with the same field of view, slice thickness and slice positions, thereby enabling superimposition and cross registration of any resultant 3D renderings of the femoral, tibial, and patellar cartilage and bone. External reference markers can aid in registering the 3D data in the same object coordinate system.

3D maps of cartilage thickness can be generated using several different techniques. One representative, but not limiting, approach uses a 3D surface detection technique which is based on a 2D edge detector (Wang-Binford) that has been extended to 3D. This surface detection technique can generate surface points and their corresponding surface normal. To smooth the contour, the program samples 25 percent of the surface points and fits a cubic spline to the sample points. The program can compute the curvature along sample spline points and find two sample points that have the maximum curvature and are separated by about half the number of voxels on the contour. These points partition the spline into two subcontours. For each subcontour, the program can compute the average distance between the points and the center of the mass. The program can designate the subcontour with the smaller average distance as the inner cartilage surface and the other subcontour as the outer cartilage surface (OCS). The intersect between the inner cartilage surface (ICS) (located at the subchondral bone interface) and the outer cartilage surface with the surface normal can be used to compute the 3D thickness of the articular cartilage on a pixel-by-pixel basis.

Creating A Three Dimensional (3D) Image of the Cartilage

Three Dimensional Geometric Model Generation

After the 3D image of cartilage and the 3D image of joint with bones (as discussed hereinafter), are obtained, for example, the set of segmented two dimensional MR images can be transformed to a voxel representation using a computer program developed in the AVS Express (Advanced Visual Systems, Inc., Waltham, Mass.). Every voxel has a value of zero if it is not within an object of interest or a value ranging from one to 4095, depending on the signal intensity as recorded by the MRI machine. An isosurface can then be calculated that corresponds to the boundary elements of the volume of interest. A tesselation of this isosurface can be calculated, along with the outward pointing normal of each polygon of the tesselation. These polygons are written to a file in a standard graphics format (Virtual Reality Modeling Language Version 1.0: VRML output language).

Visualization Software

One possible choice for the software program used to assess the cartilage degeneration pattern, the bones of the joint, and the motion pattern of the patient is a user controllable 3D visual analysis tool. The program can read in a scene, which scene consists of the various 3D geometric representations or "actors" (for example, VRML files of the tibia, tibia cartilage, femur, femoral cartilage), the static relationship transformations between these actors, and, if available, sequence of transformations describing how these actors move with respect to each other as the patient performs some activity, such as walking, jogging, etc.

The program can allow the user, through the use of the mouse and/or keyboard, the ability to observe the scene from arbitrary angles; to start and stop the animation derived from the motion profiles and to observe the contact line and any cartilage lesions while the animation is running. Additionally, the user can derive quantitative information on the scene through selecting points with the mouse.

The software program can be written in the CTT computer language and can be compiled to run on both Silicon Graphics Workstations and Windows/Intel personal computers.

Cartilage Thickness Maps

Cartilage thickness can be determined by several methods. One example is detecting the locations of the bone—cartilage and the cartilage—joint fluid interface along the surface normal using the same edge detector described below, and subtracting them. This procedure can be repeated for each pixel located along the bone—cartilage interface. The x, y, and z position of each pixel located along the bone—cartilage interface can be registered on a 3D map or multiple. 2D maps and thickness values are translated into color values. In this fashion, the anatomic location of each pixel at the bone cartilage interface can be displayed simultaneously with the thickness of the cartilage in this location.

The edge detector can produce accurate surface points and their corresponding surface normal. The detector can be applied to the baseline and the follow-up data set. For the baseline data set, both the surface points and surface normals can be used to form locally supporting planes (for each voxel). These planes can form an approximated surface for the baseline skeletal site. As for the follow-up data set, the surface points can be matched in the registration procedure onto the surface of the baseline data set. One can use a newly developed 3D surface detection technique to extract the surface of the skeletal site on both the baseline scan and the follow-up scan. Once these surfaces are detected, one can use the Levenberg Marquardt procedure to find the transformation that best matches these two surfaces.

A possible approach for calculating the cartilage thickness is based on a 3D Euclidian distance transformation (EDT). After thresholding, the voxels on the edge of the cartilage structure can be extracted using a slice by slice 8-neighbor search, resulting in a binary volume with the voxels on the cartilage surface having a value of 1 and all others being 0. To classify these surface points as part of the ICS or OCS, a semi-automatic approach, which requires the user to enter a point that lies outside the cartilage structure and faces the ICS, can be useful. From this point, rays are cast in all directions of the volume using a modified Bresenham's line drawing algorithm. If a ray hits a voxel with a value of 1, this point is classified as part of the ICS. After a complete sweep of the volume, for initialization of the EDT the ICS voxels are given a value of 0, whereas all other voxels are set to 1.

For computation of the EDT, the following representative algorithm can be useful. It can decompose the calculation into a series of 3 one-dimensional transformations and can use the square of the actual distances, which accelerates the process by avoiding the determination of square roots.

First, for a binary input picture $F=\{f_{ijk}\}$ ($1 \leqq i \leqq L$, $1 \leqq j \leqq M, \leqq 1 \leqq k \leqq N$) a new picture $G=\{g_{ijk}\}$ can be derived using equations (3-5) ($\alpha$, $\beta$, and $\gamma$ denote the voxel dimensions). Here F is a set of all voxels initially and G is a set of all voxels at the later time.

$$g_{ijk} = \min_{x}\{(\alpha(i-x))^2;\ f_{xjk} = 0;\ 1 \le x \le L\} \qquad \text{[Eq. 3]}$$

Thus, each point can be assigned the square of the distance to the closest feature point in the same row in i-direction. Second, G can be converted into $H=\{h_{ijk}\}$ using equation (4).

$$h_{ijk} = \min_{y}\{g_{iyk} + (\beta(j-y))^2;\ 1 \le y \le M\} \qquad \text{[Eq. 4]}$$

The algorithm can search each column in the j-direction. According to the Pythagorean theorem, the sum of the square distance between a point (i,j,k) and a point (i,y,k) in the same column, $(\beta(j-y))^2$, and the square distance between (i,y,k) and a particular feature point, $g_{iyk}$, equals the square distance between the point (i,j,k) and that feature point. The minimum of these sums is the square distance between (i,j,k) and the closest feature point in the two-dimensional i-j-plane. The third dimension can be added by equation (5), which is the same transformation as described in the equation for the k-direction (4).

$$s_{ijk}=\min\{h_{ijz}+(\gamma(k-z))^2;\ 1\leqq z\leqq N\} \quad \text{[Eq. 5]}$$

After completion of the EDT, the thickness of the cartilage for a given point (a,b,c) on the OCS equals the square root of $S_{abc}$. The x, y, and z position of each pixel located along the bone—cartilage interface can be registered on a 3D map and thickness values are translated into color values. In this fashion, the anatomic location of each pixel at the bone cartilage interface can be displayed simultaneous with the thickness of the cartilage in this location.

Displaying the Degeneration Pattern

In an approach the cartilage thickness maps obtained using the algorithm described above display only a visual assessment of cartilage thickness along the articular surface. In another approach, in order to derive a true quantitative assessment of the location, size, and depth of a focal cartilage defect, one can use an iterative approach comparing cartilage thickness of neighboring pixels located along the bone cartilage interface.

For example, assuming an image resolution of 0.5×0.5×1.0 mm and an average thickness of the articular cartilage in the femoral condyles ranging between 2 to 3 mm, a 25% decrement in cartilage thickness will be the smallest change that can be observed with most current imaging sequences. Therefore, for example, pixels along the bone—cartilage interface that demonstrate a decrease exceeding the smallest change observable on a given MRI pulse sequence, in this example 25% or greater, in overlying cartilage thickness when compared to cartilage thickness at the neighboring bone—cartilage interface pixels, can be used to define the margins of a focal cartilage defect. Other criteria can be employed to define a cartilage defect based on comparisons of neighboring pixels. For example, a fixed value can be used. If the difference in cartilage thickness between neighboring pixels exceeds the fixed value, e.g. 1mm, the pixel where this difference is observed can be used to define the margin of the cartilage defect. This comparison can be performed for each pixel located along the bone—cartilage interface for the entire data set. This comparison is preferably performed in three dimensions. Pixels that demonstrate a decrease in cartilage thickness exceeding defined criteria but that are completely surrounded by other pixels fulfilling the same criteria may not be considered to be part of the margin of the cartilage defect, but will typically be considered to lie inside the cartilage defect.

The invention provides for means for calculating the area covered by the cartilage defect $A_{cartilage\ defect}$ and the mean thickness of the cartilage in the region of the defect $D_{cartilage\ defect}$ as well as the mean thickness of a defined area of surrounding normal cartilage. The thickness of the cartilage previously lost in the defect can be estimated then as:

$$D_{cartilage\ loss}=D_{normal\ cartilage}-D_{cartilage\ defect} \quad \text{[Eq. 6]}$$

Since the area A of the cartilage defect is known, the volume of cartilage loss can be computed as:

$$V_{cartilage\ loss}=A_{cartilage\ defect}\times D_{cartilage\ loss} \quad \text{[Eq. 7]}$$

Figure 22A:
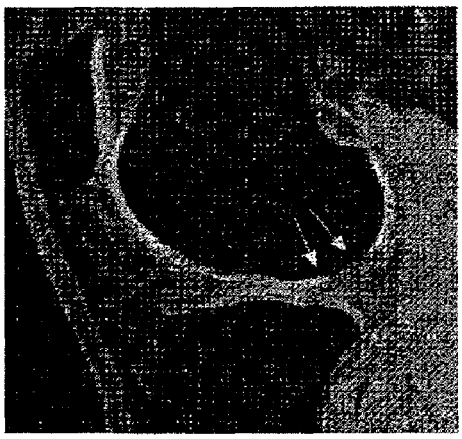
FIGS. 22A and 22B show a 2D MRI (3D SPGR) and 3D cartilage thickness map.
Figure 22B:
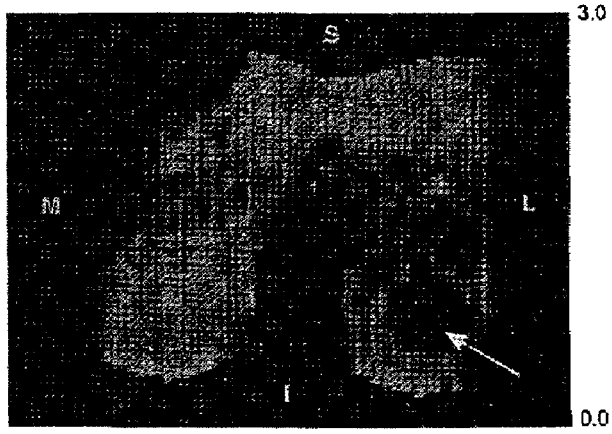
Figure 23A:
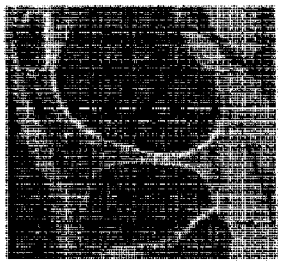
FIGS. 23A-E show the matching of 3D thickness maps generated from MR images obtained with a knee neutral position and external rotation.
Figure 23B:
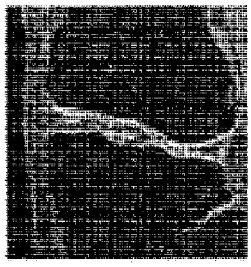
Figure 23C:
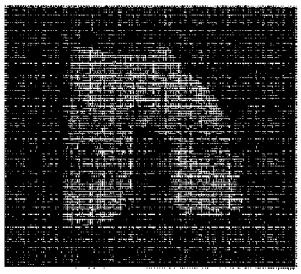
Figure 23D:
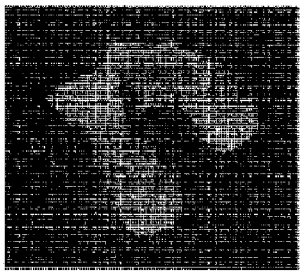
Figure 23E:
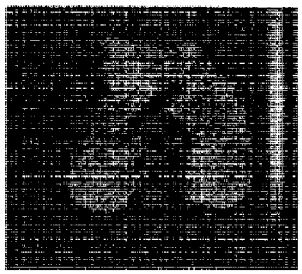

Turning now to FIGS. 22A and 22B, one can see a 2D MRI (3D SPGR) and 3D cartilage thickness map. In A, the 2D MRI demonstrates a full thickness cartilage defect in the posterior lateral femorl condyle (arrows). FIG. 22B shows a 3D cartilage thickness map generated using a 3D Euclidian distance transformation. The thickness of the articular cartilage is color encoded and displayed on a pixel-by-pixel basis along the 3D surface of the articular cartilage. The cartilage defect is black reflecting a thickness of zero (arrows) (M: medial, L: lateral, S: superior, I: inferior).

In FIGS. 23A-23E, one can see the matching of 3D thickness maps generated from MR images obtained with the knee in neutral position and in external rotation. A. Sagittal baseline MR image (3D SPGR) with-the knee in neutral position. B. Sagittal follow-up MR image of the same volunteer obtained two weeks later with the knee in 40 degree external rotation (note the artificially widened appearance of the femur resulting from the rotation). C. 3D thickness map generated based on baseline MRI in neutral position. D. 3D thickness map generated based on follow-up MRI in external rotation (note segmentation error between condyles in trochlear region). E. Transformation of D into the object coordinate system of C. Despite extreme differences in joint orientation between baseline and follow-up MRI scans and despite segmentation errors, the thickness distribution on the matched follow-up scan demonstrates great similarity with that seen on the baseline scan in neutral position (in C.).

Having now described how to obtain an image of a cartilage of a joint, both with and without external reference markers; how to enhance the image by manipulating non-cartilage images, and creating and displaying 3-D images of the cartilage, i.e. a 3-D map, certain aspects of the invention are apparent.

One aspect is a method of estimating the loss of cartilage in a joint. The method comprises (a) obtaining a three-dimensional map of the cartilage at an initial time and calculating the thickness or regional volume of a region thought to contain degenerated cartilage so mapped at the initial time, (b) obtaining a three-dimensional map of the cartilage at a later time, and calculating the thickness or regional volume of the region thought to contain degenerated cartilage so mapped at the later time, and (c) determining the loss in thickness or regional volume of the cartilage between the later and initial times.

Preferably, this aspect of the invention is directed to a volume of interest in the cartilage, i.e., a region of the cartilage that includes a cartilage defect. Such a defect may be the result of a disease of the cartilage (e.g., osteoarthritis) or the result of degeneration due to overuse or age.

This invention allows a health practitioner to evaluate and treat such defects. The volume of interest may include only the region of cartilage that has the defect, but preferably will also include contiguous parts of the cartilage surrounding the cartilage defect.

Another aspect of the invention is a method for assessing the condition of cartilage in a joint of a human, which method comprises (a) electronically transferring an electronically-generated image of a cartilage of the joint from a transferring device to a receiving device located distant from the transferring device;

(b) receiving the transferred image at the distant location;

(c) converting the transferred image to a degeneration pattern of the cartilage; and (d) transmitting the degeneration pattern to a site for analysis.

Another aspect of the invention is a method for determining the volume of cartilage loss in a region of a cartilage defect of a cartilage in joint of a mammal. The method comprises (a) determining the thickness, $D_N$, of the normal cartilage near the cartilage defect; (b) obtaining the thickness of the cartilage defect, $D_D$, of the region; (c) subtracting $D_D$ from $D_N$ to give the thickness of the cartilage loss, $D_L$; and (d) multiplying the $D_L$ value times the area of the cartilage defect, $A_D$, to give the volume of cartilage loss. The method is useful for situations wherein the region of cartilage defect is limited to the defective cartilage and preferably wherein the region of the cartilage defect includes a portion of the cartilage contiguous to the defect.

Alternatively, for step (a) the normal thickness of the defect area could be estimated. It may be estimated from measurements of cartilage of other subjects having similar characteristics such as gender, age, body type, height, weight, and other factors. It may be estimated from measurements of a similar normal" cartilage from another corresponding joint (e.g., if the right knee has the defect, measure the normal left knee). It may have been measured at an initial time $T_1$ when the cartilage was normal to provide a baseline. Other means of determining the normal thickness may be available to one of skill in the art. Once the thickness $D_N$ is obtained and the thickness $D_D$ is obtained the two are subtracted to give the $D_L$. The $D_L$ is multiplied by the area of the defect $A_D$ to give the volume of cartilage loss. By determining the volume of cartilage loss at an initial $T_1$ and again at a later time $T_2$, one can determine the change in volume loss over time.

Still another aspect of the invention is a method of estimating the change of a region of cartilage in a joint of a mammal over time. The method comprises (a) estimating the thickness or width or area or volume of a region of cartilage at an initial time $T_1$, (b) estimating the thickness or width or area or volume of the region of cartilage at a later time $T_2$, and (c) determining the change in the thickness or width or area or volume of the region of cartilage between the initial and the later times. The method is particularly useful for regions of degenerated cartilage or diseased cartilage.

Still another aspect of the invention is a method of estimating the loss of cartilage in a joint. The method comprises (a) defining a 3D object coordinate system of the joint at an initial time, $T_1$; (b) identifying a region of a cartilage defect within the 3D object coordinate system; (c) defining a volume of interest around the region of the cartilage defect whereby the volume of interest is larger than the region of cartilage defect, but does not encompass the entire articular cartilage; (d) defining the 3D object coordinate system of the joint at a second timepoint, $T_2$; (e) placing the identically-sized volume of interest into the 3D object coordinate system at timepoint $T_2$ using the object coordinates of the volume of interest at timepoint $T_1$; (f) and measuring any differences in cartilage volume within the volume of interest between timepoints $T_1$ and $T_2$.

Therapeutic Planning, Devising New Therapies

In another embodiment of the invention, thickness of the articular cartilage can be estimated using an imaging test. This imaging test can be an x-ray, ultrasound, CT scan or MRI scan. Thickness can be determined using a 3D Euclidian distance transformation as well as other techniques feasible for this purpose. Thickness can be determined in selected regions or across the entire cartilage of a joint. Thickness can be determined in areas adjacent to diseased cartilage, in areas of diseased cartilage and in areas of normal cartilage.

Furthermore, the curvature of the cartilage can be determined. For this purpose, the curvature of the inner cartilage surface, i.e. the surface facing the subchondral bone, or the outer cartilage surface, i.e. the surface facing the joint cavity, can be determined. Preferably, the inner cartilage surface at the interface with the subchondral bone will be used, since the outer cartilage surface may be subject to fraying, fissuring or more advanced stages of cartilage loss. Alternatively, the curvature of the subchondral bone can be determined. In this case, the curvature of the subchondral bone can serve as an approximation of the curvature of the articular cartilage. Curvature can be determined from an imaging test, typically an ultrasound, a CT or an MRI scan. Curvature can be determined from a three-dimensional model of the cartilage. The three-dimensional model of the cartilage can be determined using the 3D Euclidian distance transformation mentioned above. Curvature can be determined in selected regions or across the entire cartilage of a joint. Curvature can be determined in areas adjacent to diseased cartilage, in areas of diseased cartilage and in areas of normal cartilage.

Using information on thickness and curvature of the cartilage, a physical model of the surfaces of the articular cartilage and of the underlying bone can be created. This physical model can be representative of a limited area within the joint or it can encompass the entire joint. For example, in the knee joint, the physical model can encompass only the medial or lateral femoral condyle, both femoral condyles and the notch region, the medial tibial plateau, the lateral tibial plateau, the entire tibial plateau, the medial patella, the lateral patella, the entire patella or the entire joint.

In another embodiment, the location of a diseased area of cartilage can be determined, for example using a 3D coordinate system or a 3D Euclidian distance transformation in combination with some of the techniques outlined above. In another embodiment of the invention, the anteroposterior, mediolateral or superoinferior dimension of an area or multiple areas of diseased cartilage can be determined. Furthermore, the area, depth and volume of a cartilage defect can be determined, for example using a 3D Euclidian distance transformation in combination with some of the techniques outlined above In one embodiment of the invention, information on thickness of the cartilage, information on curvature of the cartilage, information on curvature of the subchondral bone or information on the location, dimensions, area, depth and volume of a defect or combinations thereof can be used to devise a treatment. For example, the dimensions of a defect determined in this manner can be used to determine the dimensions of a cartilage transplant, a cartilage graft, a cartilage implant, a cartilage replacement material, a cartilage scaffold or a cartilage regenerating material or any cartilage repair system. Additionally, the curvature of the inner cartilage surface or the subchondral bone can be measured and this information can be used to determine the shape of a cartilage transplant, a cartilage graft, a cartilage implant, a cartilage replacement material, a cartilage scaffold or a cartilage regenerating material or any cartilage repair system. Additionally, the thickness of normal cartilage adjacent to the defect can be measured and the thickness values measured in this fashion can be used to determine the optimal thickness for a cartilage transplant, a cartilage graft, a cartilage implant, a cartilage replacement material, a cartilage scaffold or a cartilage regenerating material or any cartilage repair system. Alternatively, the thickness of the cartilage can be measured in the contralateral joint, e.g. the knee joint, in an area corresponding to the area of diseased cartilage in the affected joint. Using any of these techniques or, preferably, a combination thereof, an optimal fit can be achieved between the surrounding normal cartilage and a cartilage transplant, a cartilage graft, a cartilage implant, a cartilage replacement material, a cartilage scaffold or a cartilage regenerating material or any cartilage repair system thereby minimizing incongruity at the joint surface and improving the therapeutic result.

The invention provides for means to create a cast or a mold for shaping a cartilage transplant, a cartilage graft, a cartilage implant, a cartilage replacement material, a cartilage scaffold or a cartilage regenerating material or any cartilage repair system. This can be generated using computer devices and automation, e.g. computer assisted design (CAD) and, for example, computer assisted modeling (CAM).

In another embodiment, the invention provides for means to measure and visualize the curvature of the surfaces of cartilage and bone. In another embodiment, the invention provides for means to compare the thickness and the curvatures of surfaces of a cartilage transplant and a transplantation site, a cartilage graft and a graft site, a cartilage implant and an implantation site, a cartilage replacement material and an implantation site, a cartilage scaffold and a cartilage defect, a cartilage regenerating material and an area of diseased cartilage, or a cartilage repair system and an area of diseased cartilage.

The invention is useful for determining the shape, dimensions and thickness of a cartilage transplant, a cartilage graft, a cartilage implant, a cartilage replacement material, a cartilage scaffold or a cartilage regenerating material or any cartilage repair system prior to treatment. For example, the shape, dimensions and thickness of a cartilage transplant, a cartilage graft, a cartilage implant, a cartilage replacement material, a cartilage scaffold or a cartilage regenerating material or any cartilage repair system can be designed to follow the physical shape and thickness of the cartilage adjacent to an area of diseased cartilage determined using the imaging test.

The invention is applicable to a host of current and future treatments of arthritis including but not limited to cartilage transplants, cartilage implants, cartilage grafts, cartilage replacement materials, cartilage scaffolds, cartilage regenerating materials, auto-, allo- and xeno-transplants, osteochondral allo- and autografting, stem cell based repair systems and transfer systems, and, principally, any other current and future treatments and devices for cartilage repair or regeneration.

The example described below shows one possibility how aspects of the invention can be implemented. It demonstrates one possible way how the invention can be practiced. It is in no way meant to limit the invention. One skilled in the art will easily recognize other means of practicing the invention.

In a first step, the cartilage and bone contours can be segmented from the MR images using for example a modified live wire technique [Steines D, Cheng C, Wong A, Berger F, Napel S, Lang P. CARS—Computer-Assisted Radiology and Surgery, p. 578-583, San Francisco, 2000].

From the segmented data, a 3-dimensional surface representation can be created, which yields a triangular tesselation of the surface. For this calculation, a 3-dimensional Wang-Binford edge detector [Yan C H: Measuring changes in local volumetric bone density: new approaches to quantitative computed tomography, Ph.D. thesis, 1998, Dept. of Electrical Engineering, Stanford University] or the marching cubes algorithm [Lorensen W E, Cline H E. Comput Graph 1987; 21: 163-169] can be used. This surface representation can be imported into a CAD system, which is used to generate a physical model or a cast by means of rapid prototyping techniques.

The segmented data can also be used for measuring the surface curvature at the surface points. The curvature is calculated according to formula xx. If $\alpha(a,b)\rightarrow IR^2$ is a curve defined over the parameter interval (a,b) by $\alpha(t)=(x(t),y(t))$, then the curvature $\kappa$ is given by [Gray A: Modern Differential Geometry of Curves and Surfaces. 1993; CRC Press]:

$$\kappa(t) = \frac{x'(t)y''(t) - x''(t)y'(t)}{(x'^2(t) + y'^2(t))^{\frac{3}{2}}} \quad \text{[Eq. 8]}$$

For the digitized contours that result from the segmentation, smooth derivatives for equation (8) can be obtained by convolution with differentiated Gaussian kernels [Worring M, Smeulders A W M. CVGIP: Image Understanding, 1993. 58(3): p. 366-382].

The curvature values can be calculated for each pixel on the segmented surface in each slice. They can subsequently be color-mapped onto a 3-dimensional rendering of the surface for visualization purposes.

For full curvature information this procedure can be repeated for a direction perpendicular to the imaging plane. Of the remaining two main directions the one with the lower degree of parallelism to the surface can be chosen, and reformatted slices of the MR data set can be obtained for this direction. For instance, when curvature values for the femoral condyles are calculated from sagittal MR images of the knee, the data set would typically be reformatted for a coronal slicing plane.

The procedure of segmentation and curvature calculation can then be repeated for the reformatted images. A second curvature map can be calculated, yielding complementary information to the first one.

In order to compare curvature values for different surface patches, these can be manually or automatically registered, overlaying one surface patch on top of the other. Corresponding curvature values that are calculated in the same directions can now be subtracted from each other, thereby yielding a measure of how well curvatures of two surfaces match.

An example how aspects of the invention can be practiced clinically in a patient is given below. It demonstrates one possible way how the invention can be practiced. It is in no way meant to limit the invention. One skilled in the art will easily recognize other means of practicing the invention.

A patient with arthritis of the knee joint is referred for an MRI scan. The MRI scan is performed using a cartilage sensitive MRI pulse sequence such as a fat saturated spoiled gradient echo sequence or a water selective 3D gradient echo sequence using a spectral spatial pulse. The MR images are transferred via a local network or, for example, the internet into a computer workstation. The computer workstation uses software to extract or segment the articular cartilage from the surrounding tissue. Such software can include snake algorithms, livewire algorithms, signal intensity based thresholding, or seed growing algorithms as well as any other technique useful for this purpose. The software can then generate a three-dimensional map of cartilage thickness across the femoral condyles, the tibial plateau, or the patella. This can be achieved using a 3D Euclidian distance transformation. Additionally, the software can provide information on cartilage curvature or curvature of the subchondral bone as described above. Furthermore, the software can determine the location, dimensions, size, area, depth, or volume of areas of diseased cartilage.

The information generated in this fashion can be used to generate a physical model of the area of diseased cartilage. For example, a bone replacement material can be formed with a CAD/CAM system using the above information. One of the surfaces of the bone replacement material can be shaped so that it matches the 3D curvature of the subchondral bone subjacent to the area of diseased cartilage. Additionally, the anteroposterior, mediolateral or superoinferior dimensions of this surface of the bone replacement material can be such that it matches the dimensions of the area of diseased cartilage. Cartilage cells can be affixed to the bone replacement material and can be grown on the bone replacement material until the thickness of the resultant cartilage matches that of the thickness of the cartilage adjacent to the area of diseased cartilage measured on the 3D cartilage thickness map. Alternatively, a layer of cartilage of known thickness can be applied to the bone replacement material whereby the thickness can be chosen to match the thickness of the cartilage adjacent to the area of diseased cartilage measured on the 3D cartilage thickness map.

Alternatively, an artificial non-human material with properties similar to cartilage can be applied to the bone replacement material whereby the thickness of this material can be chosen to match the thickness of the cartilage adjacent to the area of diseased cartilage measured on the 3D cartilage thickness map.

Alternatively, cartilage can be grown on a mold matching the curvature of the subchondral bone in an area of diseased cartilage whereby the dimensions of the surface of the mold on which the cartilage is grown matches the dimensions of an area of diseased cartilage. Cartilage can then be grown on the mold until its thickness matches the thickness of cartilage adjacent to the area of diseased cartilage as measured, for example, on a 3D cartilage thickness map. At this point, for example, an orthopedic surgeon can excise the area of diseased cartilage and can implant the cartilage or cartilage replacement material. Since the curvature of the cartilage or cartilage replacement material matches that of the underlying subchondral bone and since the thickness of the cartilage or cartilage replacement material matches that of the cartilage adjacent to the area of excised diseased cartilage, normal or near normal joint congruity can be achieved with a resultant decrease in wear on the implanted cartilage or cartilage replacement material and also a decrease in wear on the adjacent cartilage or the cartilage of the opposing joint surface.

Display of Biochemical Information In addition to providing a 2D or 3D representation of the morphological properties of cartilage, the invention provides for techniques to represent one or more biochemical components of articular cartilage.

A biochemical component includes, but is not limited to, glycosaminoglycan, water, sodium, or hyaluronic acid. Biochemical data can be generated with other magnetic resonance based techniques including the use of signal intensity measurements, relaxation time measurements, paramagnetic and other contrast media and sodium rather than proton MR imaging. Other imaging tests such as positron emission tomography scanning can also be used for this purpose. Thus, one aspect of this invention is a method for providing a biochemically-based map of joint cartilage. The method comprises (a) measuring a detectable biochemical component throughout the cartilage,
(b) determining the relative amounts of the biochemical component throughout the cartilage;
(c) mapping the amounts of the biochemical component through the cartilage; and
(d) determining the areas of cartilage deficit by identifying the areas having an altered amount of the biochemical component present.

Once a map is obtained, it can be used in assessing the condition of a cartilage at an initial time and over a time period. Thus, the biochemical map may be used in the method aspects of the invention in a manner similar to the cartilage thickness map.

For example, one aspect is a method of estimating the loss of cartilage in a joint. The method comprises (a) obtaining a relaxation time or biochemical map of the cartilage at an initial time and analyzing the relaxation time or biochemical content of a region thought to contain degenerated cartilage so mapped at the initial time,
(b) obtaining a relaxation time or biochemical map of the cartilage at a later time, and time analyzing the relaxation time or biochemical content of the region thought to contain degenerated cartilage so mapped at the later time, and
(c) determining the change in relaxation time or biochemical content of the cartilage between the later and initial times.

Preferably, this aspect of the invention is directed to a volume of interest in the cartilage, i.e., a region of the cartilage that includes a cartilage defect. Such a defect may be the result of a disease of the cartilage (e.g., osteoarthritis) or the result of degeneration due to overuse or age. This invention allows a health practitioner to evaluate and treat such defects. The volume of interest may include only the region of cartilage that has the defect, but preferably will also include contiguous parts of the cartilage surrounding the cartilage defect.

As discussed herein before, another aspect of the invention is a method for assessing the condition of cartilage in a joint using a relaxation time or the biochemical map. The method comprises (a) electronically transferring an electronically-generated relaxation time or biochemically based image of a cartilage of the joint from a transferring device to a receiving device located distant from the transferring device;
(b) receiving the transferred image at the distant location;
(c) converting the transferred image to a degeneration pattern of the cartilage; and
(d) transmitting the degeneration pattern to a site for analysis.

Another aspect of the invention is a method for determining the change of biochemical content in a region of a cartilage defect of a cartilage in joint of a mammal. The method comprises (a) determining the biochemical content ($BC_N$) of the normal cartilage near the cartilage defect;
(b) obtaining the biochemical content of the cartilage defect ($BC_D$) of the region; and
(c) subtracting $BC_D$ from $BC_N$ to give the value of the cartilage change, $BC_D$. The method is useful for situations wherein the region of cartilage defect is limited to the defective cartilage and preferably wherein the region of the cartilage defect includes a portion of the cartilage contiguous to the defect.

Alternatively, for step (a) the normal content of the defect area could be estimated. It may be estimated from measurements of cartilage of other subjects having similar characteristics such as gender, age, body type, height, weight, and other factors. It may be estimated from measurements of a similar 'normal" cartilage from another corresponding joint (e.g., if the right knee has the defect, measure the normal left knee). It may have been measured at an initial time $T_1$ when the cartilage was normal to provide a baseline. Other means of determining the normal content may be available to one of skill in the art. Once $BC_N$ is obtained and $BC_D$ is obtained the two are subtracted to give the $\Delta$. By determining the change of content at an initial $T_1$ and again at a later time $T_2$, one can determine the change in biochemical content over time.

Once a relaxation time or biochemically-based map is provided, morphological maps of articular cartilage obtained with MR imaging can be superimposed, merged or fused with the biochemical map or data. Several different techniques can be applied in order to superimpose, merge, or fuse morphological data with biochemical data. For example, 2D or 3D morphological data of articular cartilage can be acquired with the same object coordinates as the biochemical data. Morphological data and biochemical data can then be easily displayed simultaneously using different colors, opacities, and or gray scales. Alternatively, 2D or 3D morphological data or articular cartilage can be acquired with different object coordinates as the biochemical data. In this case, a 3D surface registration can be applied in order to superimpose, merge, or fuse the morphological data and the biochemical data. As an alternative to 3D object coordinates, anatomic landmarks can be used to register the morphological data and subsequently the biochemical data in a 3D object coordinate system. 3D object coordinate systems can then be matched by matching the landmarks obtained from the morphological data with those obtained from the biochemical data.

Thus, another aspect of this invention is a method for assessing the condition of a subject's cartilage in a joint, the method comprises obtaining a three dimensional biochemical representation of the cartilage, obtaining a morphological representation of the cartilage, and merging the two representations, and simultaneously displaying the merged representations on a medium. The merged representations are then used to assess the condition of a cartilage, estimate the loss of cartilage in a joint, determining the volume of cartilage loss in a region of cartilage defect, or estimating the change of a region of cartilage at a particular point in time or over a period of time. One can see that similar steps would be followed as spelled out for the use of a thickness map or biochemical map.

Simultaneous display of morphological data with biochemical data provides a useful tool to assess longitudinal changes in morphology or articular cartilage and biochemical composition of articular cartilage, for example during treatment with chondroprotective and chondroregenerative agents.

Part of the unique aspect of this technology is that it lends itself to assessment of a patient from a distant position after an image is taken of the joint under evaluation. Thus one aspect of this invention is a method for assessing the condition of cartilage in a joint from a distant location. The method comprises (a) electronically transferring an electronically-generated image of a cartilage of the joint from a transferring device to a receiving device located distant from the transferring device;

(b) receiving the transferred image at the distant location;

(c) converting the transferred image to a degeneration pattern of the cartilage; and (d) transmitting the degeneration pattern to a site for analysis.

The degeneration pattern includes a measure of cartilage thickness or regional cartilage volume.

The electronically generated image of the cartilage preferably is an MR image and the degeneration pattern can be displayed as a three-dimensional image as a thickness pattern, a biochemical content pattern or a merged thickness biochemical pattern. The electronically generated image is transmitted via Dicom, using the international standards for transmission of such images.

Another aspect of the invention is a kit for aiding in assessing the condition of cartilage in a joint of a mammal, which kit comprises a software program, which that when installed and executed on a computer reads a cartilage degeneration pattern presented in a standard graphics format and produces a computer readout showing a cartilage thickness map of the degenerated cartilage.

The software can be installed in a PC, a Silicon Graphics, Inc. (SGI) computer or a Macintosh computer. Preferably, the software calculates the thickness or regional volume of a region of degeneration of the cartilage which does not include the entire volume of the articular cartilage.

THE MOVEMENT PATTERN

To acquire a movement pattern of a joint in accordance with this invention, one obtains an internal image of the bones in a joint, preferably using MRI techniques, and obtains an external image of the bones in motion. The images are correlated, preferably through the use of external marker sets, to give a pattern that shows a static or moving condition. The correlated images are then displayed and the relation between the movement and degeneration patterns is determined.

Obtaining An Internal Image of Joint with Bones

To obtain an internal image of a joint with the associated bones, one preferably uses MRI techniques that provide an image of the bones on either side of the joint. Here, it is important to use the imaging technique that gives the best image of the bones and how they interact. Because the internal image of the bones can be combined with the image of the bones obtained by external measurements, it is particularly useful, and therefore preferred, to use external reference markers that can be similarly-positioned to the markers used in obtaining the external measurements. The external markers can be placed at any landmarks about the joint of interest. At least three markers are used for each limb being imaged. Preferably the markers will be made of a material that not only will be detected by MRI imaging techniques, but also will be detected by external imaging techniques. The markers will be associated with a means to affix them to the skin and preferably have an adhesive portion for adhering to the skin and a detectable entity that will show up on the MRI image.

The preferred MRI imaging technique useful for obtaining an internal image is a spoiled 3D gradient echo, a water selective 3D gradient echo or a 3D DEFT sequence. A further discussion may be found hereinbefore or in the 2$^{nd}$ Edition of Brown and Semelka's book entitled "MRI Basic Principles and Applications."

Once an MR image is obtained the image is manipulated to enhance the image of the bones. Procedures similar to those discussed hereinbefore for cartilage may be used, but modified for application to bone images.

Creating Three-Dimensional (3D) Image of Joint/Bones

Three-Dimensional Geometric Model Generation

After the 3D image of a joint with bones, the set of segmented two dimensional MR images can be transformed to a voxel representation inside AVS Express (Advanced Visual Systems, Inc., Waltham, Mass.). Every voxel has a value of zero if it is not within an object of interest or a value ranging from one to 4095, depending on the signal intensity as recorded by the 1.5 T MR. An isosurface can then be calculated that corresponds to the boundary elements of the region of interest. A tesselation of this isosurface can be calculated, along with the outward pointing normal of each polygon of the tesselation. These polygons can then be written to a file in a standard graphics format (Virtual Reality Modeling Language Version 1.0).

As discussed hereinbefore, the use of reference markers on the skin around the joint and the bones can provide an image that can later be matched to the reference markers for the cartilage image and the bone images obtained from external measurements.

Alternatively, a semi-automated, 3D surface-based registration technique that does not require the use of an external frame or fiducial markers can be used. This 3D surface-based registration technique can be used to match the anatomic orientation of a skeletal structure on a baseline and a follow-up CT or MRI scan. We extended a robust and accurate 2D edge detector (Wang-Binford) to 3D. This detector is described hereinbefore.

Figure 10A:
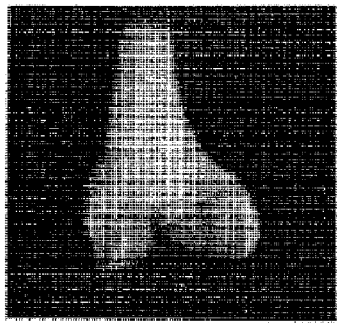
FIGS. 10A-10C show a 3D surface registration of femoral condyles based on T1-weighted spin-echo MR images.
Figure 10B:
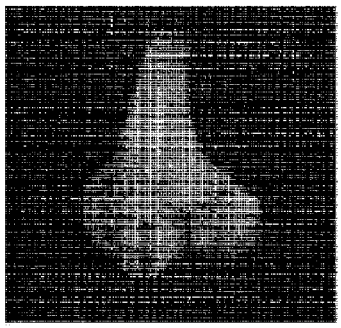
Figure 10C:
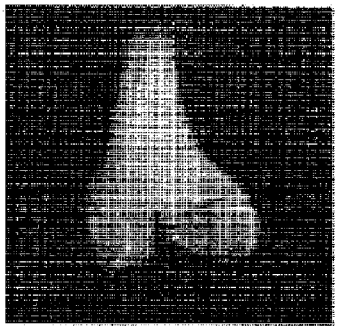

A registration technique for the femoral condyles and the tibial plateau is shown in FIG. 10. It shows an example where 3D surfaces of the femoral condyles were extracted from two differently oriented T1-weighted spin-echo MRI scans (baseline A and follow-up B, respectively) obtained in the same patient in neutral position (A) and in 40 degree external rotation (B). The 3D surfaces were used to derive a coordinate transformation relating the two scans. FIG. 10C demonstrates the use of the derived transformation to re-register scan B in the object coordinate system of scan A. Such a transformation relating two T1-weighted scans can then be used to register DEFT cartilage-sensitive scans that are acquired in the same respective orientations as the A and B T1-weighted scans.

We performed the registration using a Sun Sparc 20 workstation with 128 MBytes of memory. The surface detection algorithm extracted approximately 12,000 surface patches from each data set. The surface extraction and registration routines took about 1 hour in total.

Figure 11A:
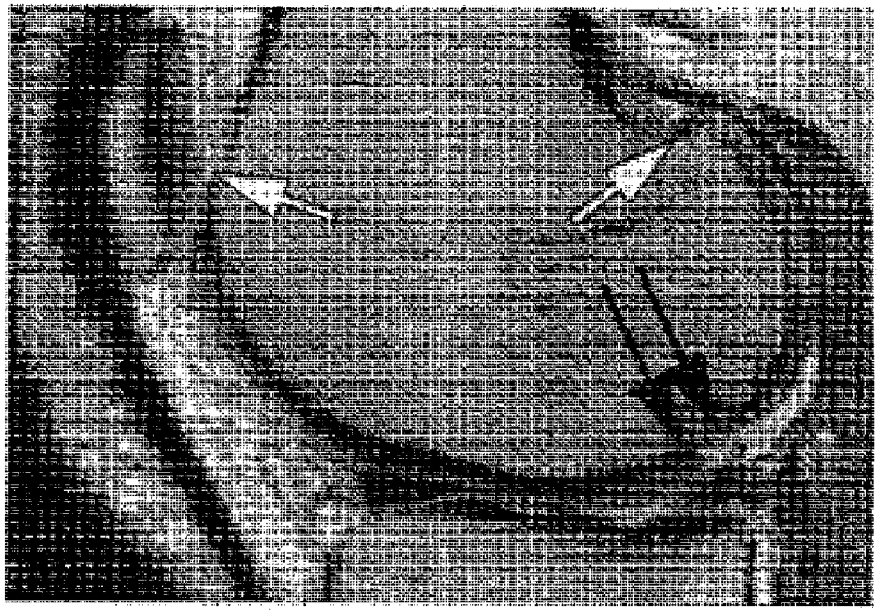
FIG. 11B is a 2D cartilage thickness map demonstrating abrupt decrease in cartilage thickness in an area of the defect (arrows). The Δ thickness between the neighboring pixels can be used to define the borders of the cartilage defect. Note diffuse cartilage thinning in the area enclosed by the asterisks (*).
Figure 11B:
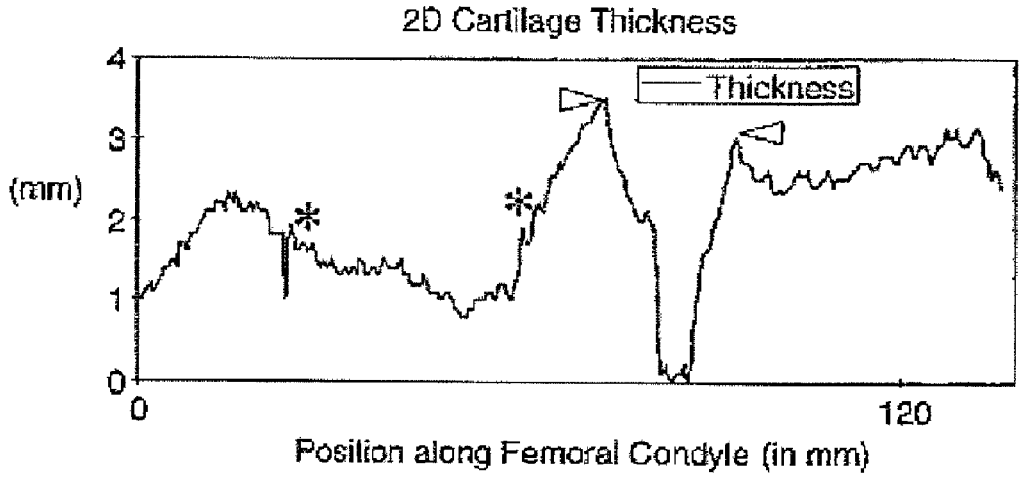

Since the algorithm for 3D surface registration of the femoral condyles also computes the surface normals for the medial and lateral femoral condyles on a pixel-by-pixel basis, it can form the basis for developing maps of cartilage thickness. FIG. 11 shows an example of a 2D map of cartilage thickness derived from the surface normals of the lateral femoral condyle. FIG. 11A shows a proton density fast spin-echo MR image that demonstrates a focal cartilage defect in the posterior lateral femoral condyle (black arrows). White arrows indicate endpoints of thickness map. FIG. 11B is a 2D cartilage thickness map that demonstrates abrupt decrease in cartilage thickness in the area of the defect (arrows). The Δ thickness between neighboring pixels can be used to define the borders of the cartilage defect. Note diffuse cartilage thinning in area enclosed by the astericks (*).

In another embodiment, cartilage sensitive images can be used instead of T1-weighted or T2-weighted scans and the surface match can be performed based on the cartilage contour.

Alternatively, anatomic landmarks present on both baseline and follow-up scans can be used to match the data obtained during the baseline and those obtained during the follow-up scan. Another alternative for matching the baseline and the follow-up scan includes the use of external or internal fiducial markers that can been detected with MR imaging. In that case, a transformation is performed that matches the position of the markers on the follow-up scan with the position of the markers on the baseline scan or vice versa.

Obtaining An External Image of Joint/Bones

Before merging or superimposing morphological maps of articular cartilage obtained by MR imaging with biomechanical data, one must obtain the biomechanical data. Such biomechanical data include, but are not limited to, estimations of static loading alignment in standing or weight-bearing position and lying or non-weight-bearing position, as well as during joint motion, e.g., the movement of load-bearing pathway on the cartilage in the knee joint during gait. Biomechanical data may be generated using theoretical computations, based on data stored in a database that can be accessed by calling up and screening for certain characteristics. Alternatively, gait analysis may be performed for an individual and data obtained during gait analysis may be merged or fused with morphological MRI data. Morphological data and biomechanical data can then be easily displayed simultaneously using different colors, opacities, and or gray scales. Additionally, the load-bearing pathway, for example around a cartilage defect, can be plotted or superimposed onto morphological maps.

Preferably, reference markers or fiducial markers can be applied to the external surface on the skin overlying the joint. These markers adhere to the skin are typically made of materials that can be detected with MRI and that can be used to register joint motion during biomechanical analysis, e.g. gait analysis. These markers can then be used to correlate the morphological with the biomechanical data.

Simultaneous display of morphological data with biomechanical data provides a useful tool to assess the load pathway applied to articular cartilage and inside and around cartilage defects. Estimation of load pathway applied in and around a cartilage defect can be used to assess a cartilage defect and to guide the choice of therapy, e.g. treatment with chondroprotective or chondroregenerative agents, osteochondral allografting, cartilage transplantation, femoral or tibial osteotomy, or joint replacement surgery.

Recording Static Joint/Bones and Joint/Bones in Movement

In obtaining an external image of the bones on either side of a joint, one must record a static image as well as a moving image of the subject joint and bones. For analysis of the knee joint, gait analysis techniques have been shown to be very effective in generating accurate, reproducible data on the six degree of freedom motion of the knee. The motion of the knee joint can be quantified in terms of flexion, rotation and displacement. Fidelity in the dynamic visualizations of subject specific MR generated knee geometry and subsequent contact surface determination call for a high degree of accuracy for the motion capture portion of the studies.

Gait Analysis Activities

In performing a gait analysis, a subject is tested standing still, laying down, walking or running on a level surface, flexing a leg in a standing position, ascending and descending stairs, flexing the leg in a seated position, and the like. The level walking measurements can include, but is not limited to, six stride cycles for each side over a range of walking speeds. The subject can be instructed to walk at a comfortable speed (normal), slower than normal and faster than normal. Typically, this protocol produces gait measurements over a range of walking speeds. The standing and laying portions of the protocol can be used in the cross registration to the MR data. The instrumentation preferably includes, at least a two camera, video-based opto-electronic system for 3-D motion analysis, a multi-component force plate for measurement of foot-ground reaction force and a computer system for acquisition, processing and analysis of data.

Anatomic Coordinate Systems

Figure 12A:
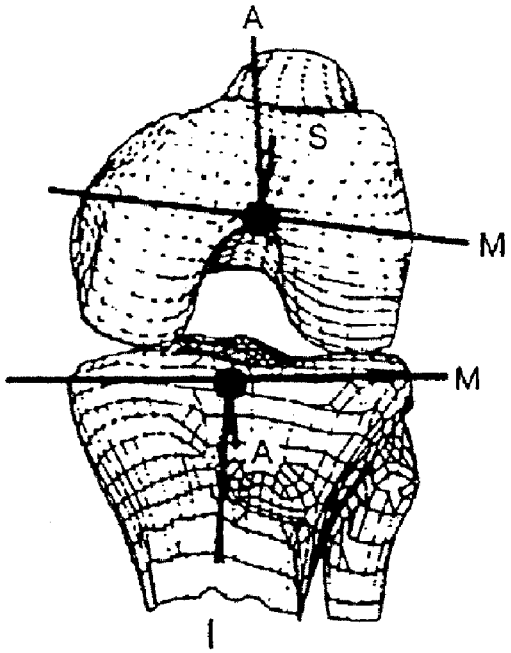
FIG. 12 shows the anatomic coordinate system in the femur and in the tibia.
Figure 12B:
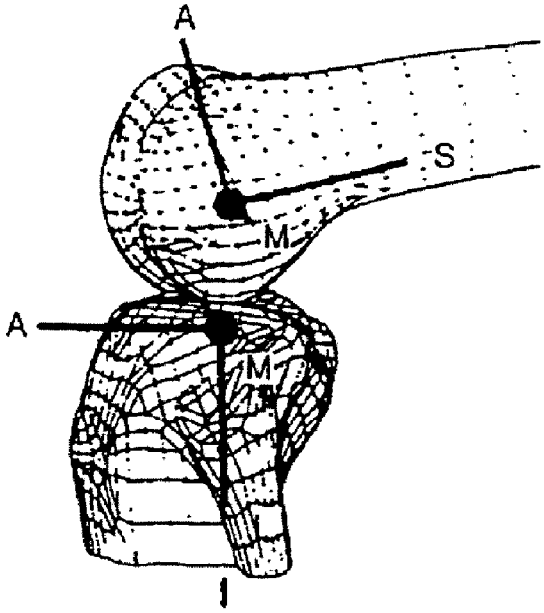
Figure 13:
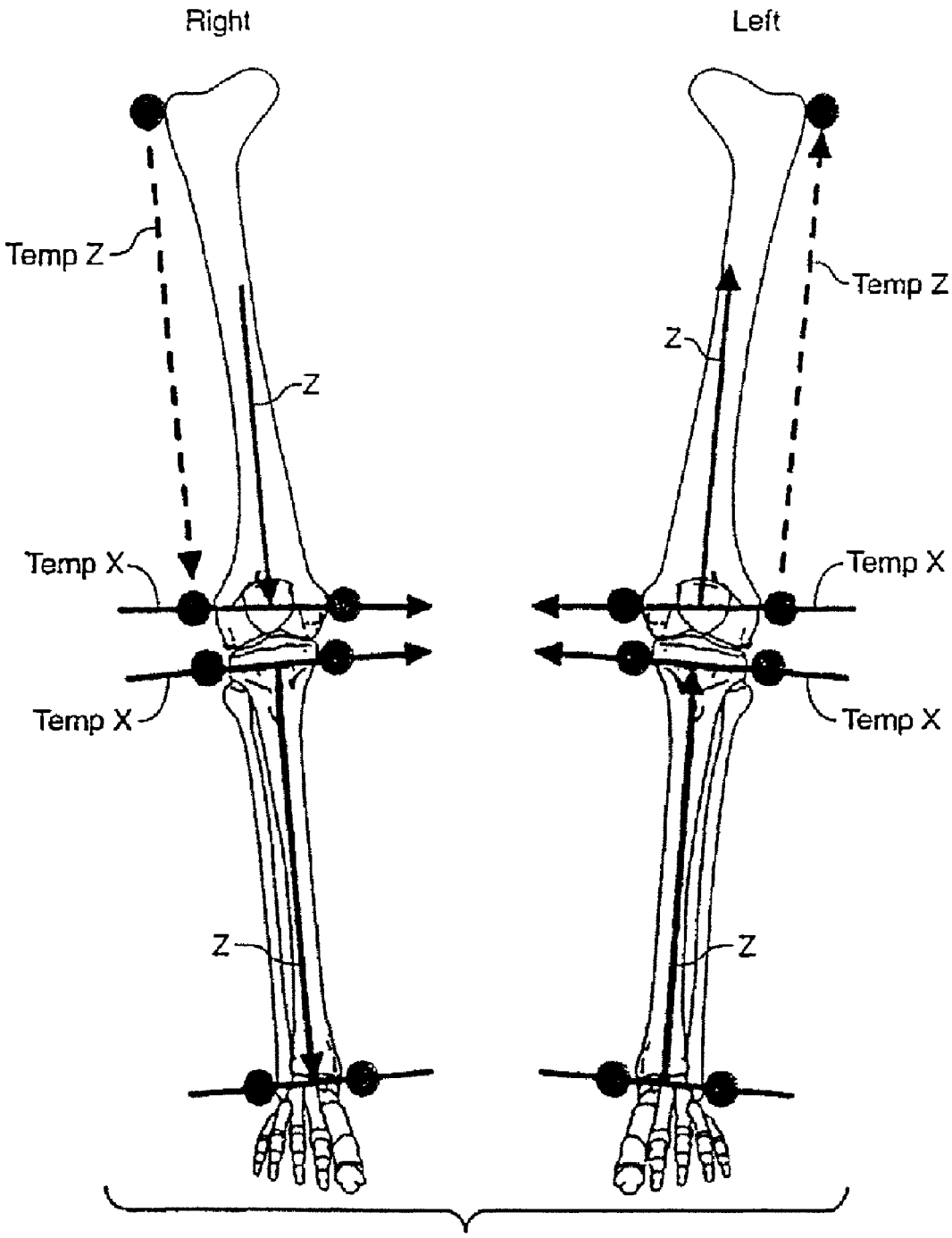
FIG. 13 shows calculation of the anatomic coordinate system from palpable bony landmarks.

Currently, the anatomic coordinate systems are defined through bony landmarks which can be identified through palpation. To describe the motion of the underlying bones in terms of the global coordinate system a subset of the markers in a point cluster technique (discussed hereinafter) are referenced to bony landmarks on the femur and tibia. Techniques described previously by Hopenfeld and Benedetti can be used to locate these bony landmarks. The anatomic coordinate systems used can be similar to that previously described by LaFortune with the exception of the origin of the femoral coordinate system. For the thigh segment, a coordinate system is located in the femoral condyles. The femoral condyles medial(M)-lateral(L) axis (FIG. 12) runs through the trans-epicondylar line (a line drawn between the medial-lateral femoral epicondyles). The midpoint of this axis is the origin. The inferior(I)-superior(S) axis runs parallel to the long axis of the femur, passing through the midpoint of the trans-epicondylar line. The anterior(A)-posterior(P) axis is the cross product of the medial-lateral and inferior-superior axes. The final position of the inferior-superior axis is made orthogonal to the anterior-posterior and medial-lateral axis through a cross product operation (FIG. 13). For the shank segment, the tibial coordinate system begins with the medial-lateral axis running through the most medial and lateral edges of the plateau. The inferior-superior axis is perpendicular to the medial-lateral axis passing through the tibial eminence. The anterior-posterior axis is the cross product of the medial-lateral and inferior-superior axes.

Placement of Markers Prior to Activity

Figure 14B:
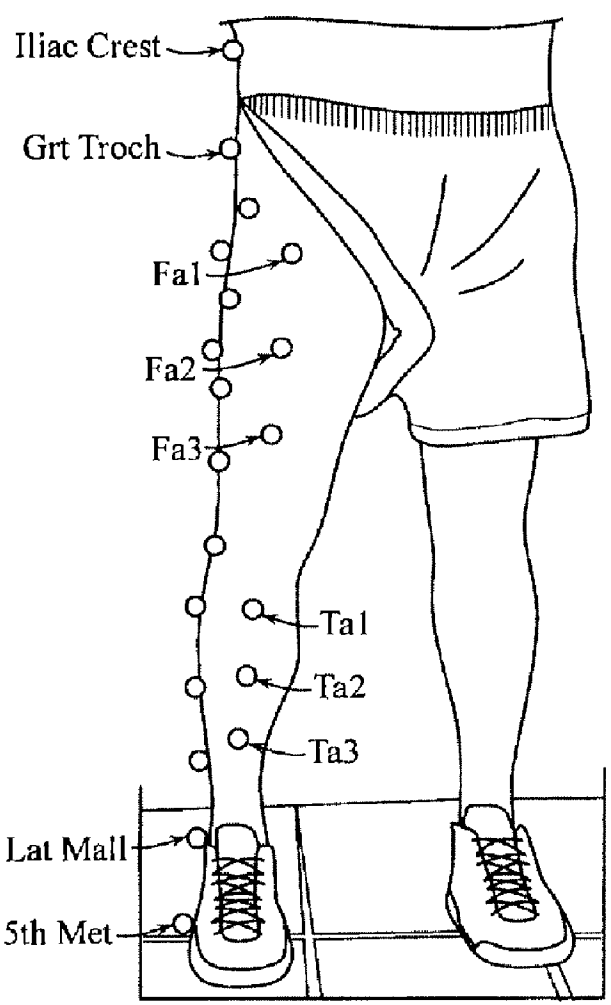
FIG. 14 shows additional marker names and locations for MR to optical cross registration.
Figure 14A:
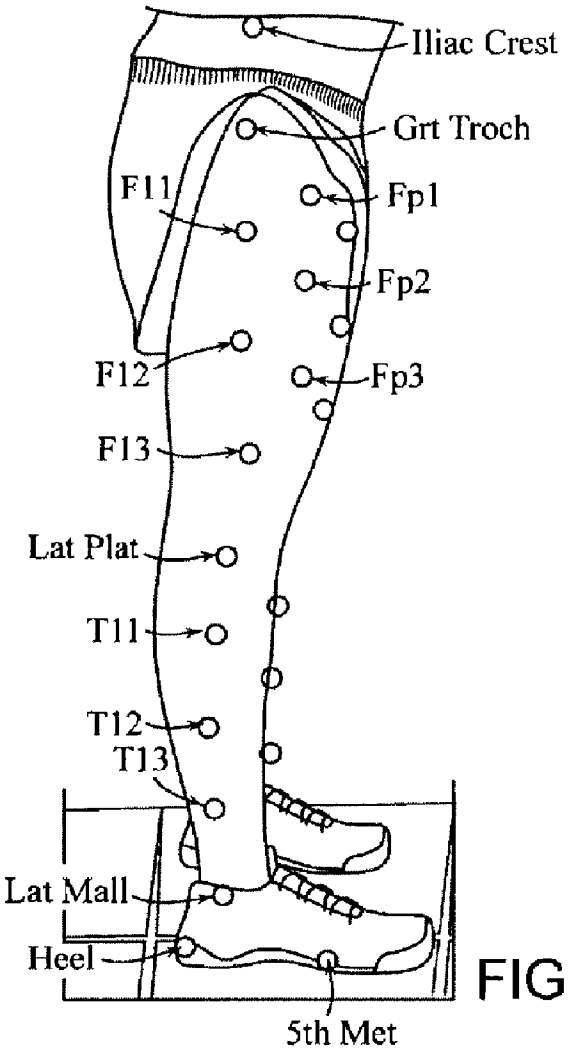
Figure 15A:
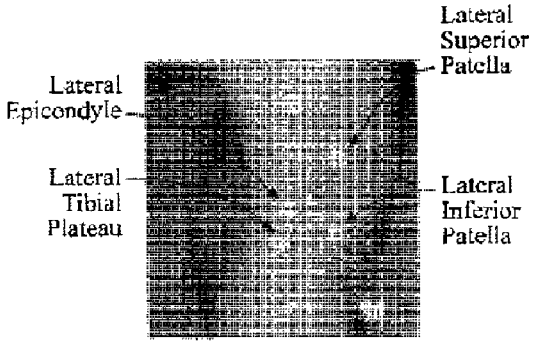
FIG. 15 shows the marker names and locations for the standard point-cluster technique protocol.
Figure 15B:
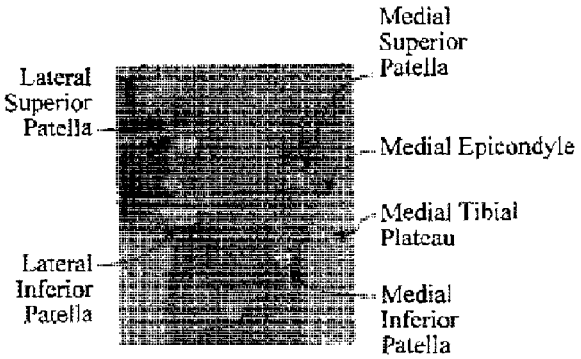
Figure 16A:
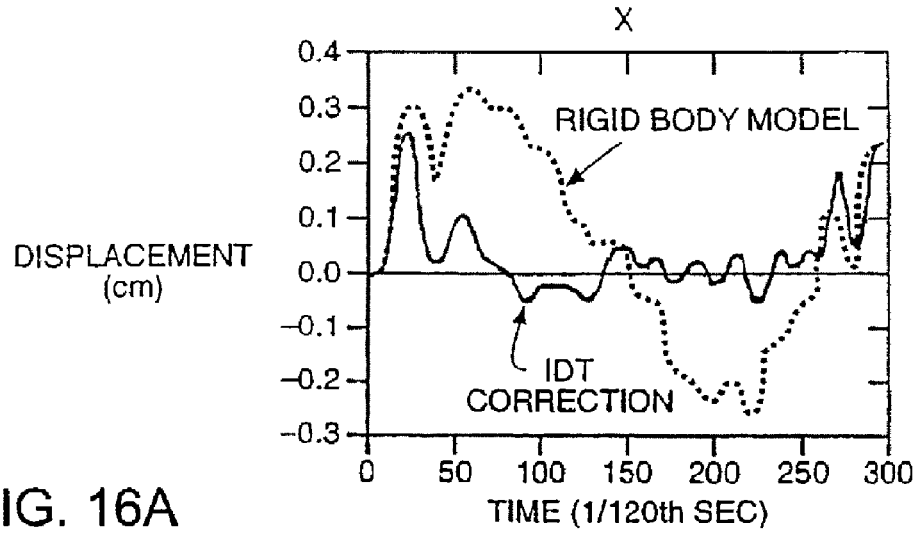
FIG. 16 shows the error in the tibial location estimate for the rigid body model and the intrical deformation correction technique.
Figure 16B:
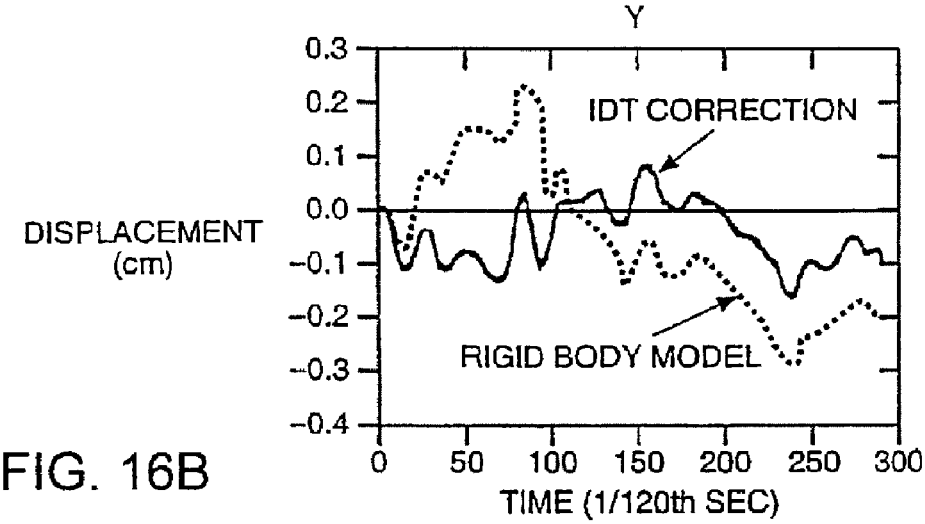
Figure 16C:
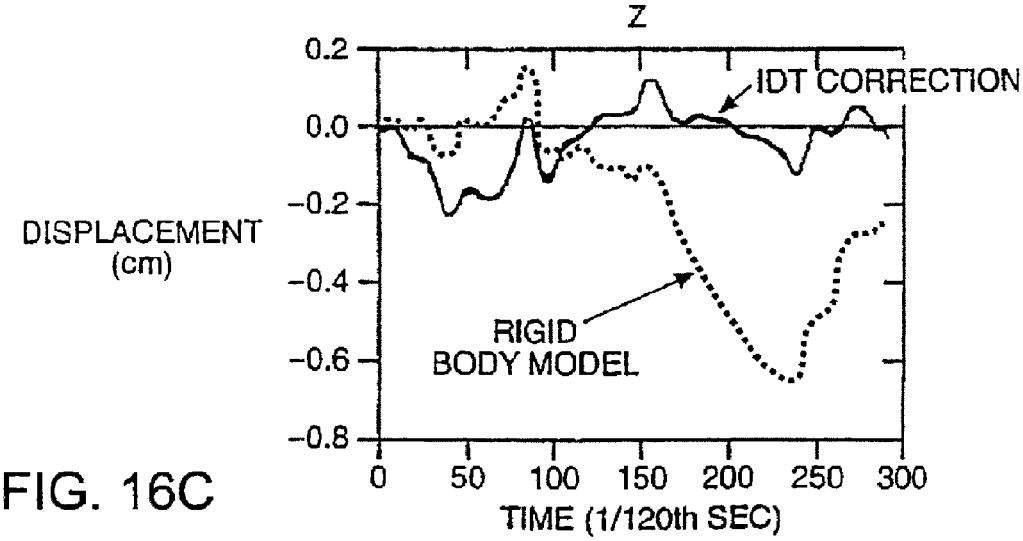
Figure 17A:
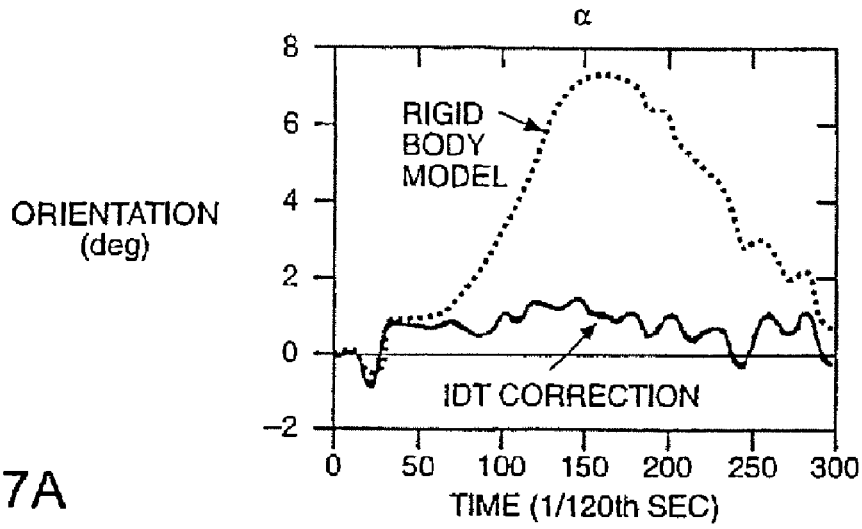
FIG. 17 shows the error in tibial orientation estimate for the rigid body model and the interval reformation correction technique.
Figure 17B:
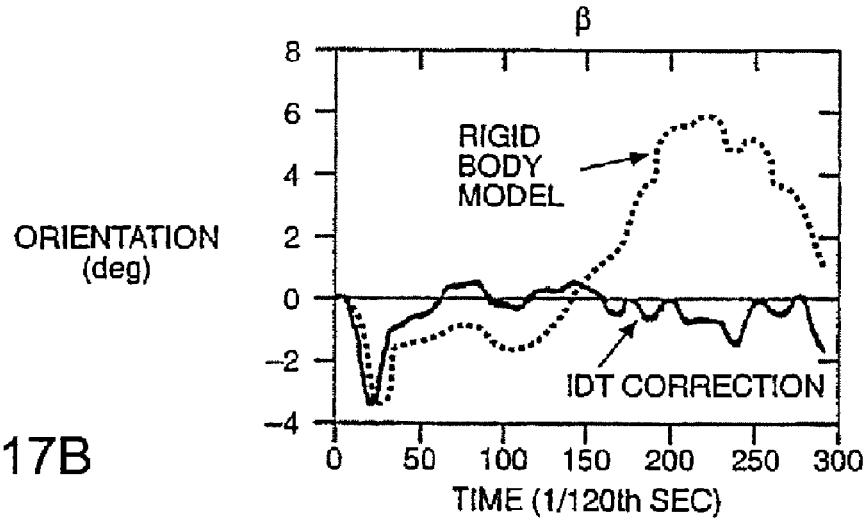
Figure 17C:
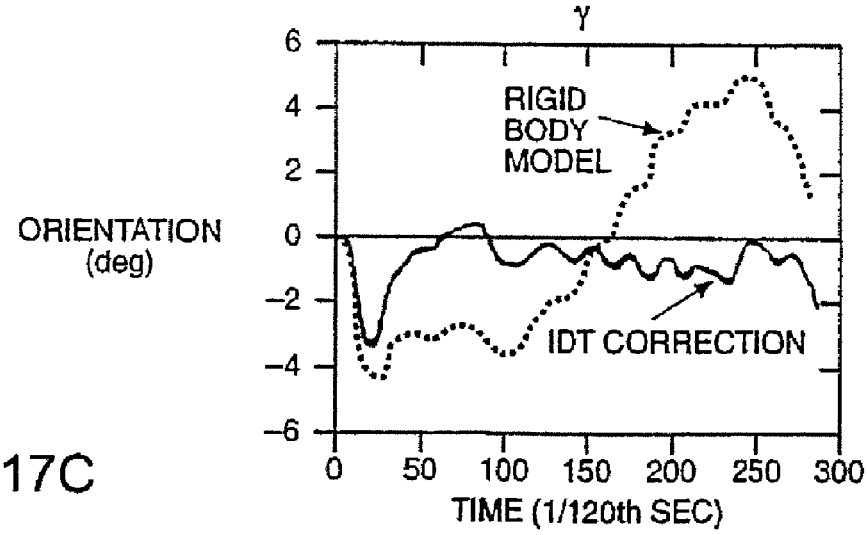

In assessing a joint, the lower extremity can be idealized as 3 segments with six degree-of-freedom joints at the knee and ankle. For the mobile activities described above, at least 3 markers per segment are used. FIG. 14 shows 21 passive retro-reflective markers located on the leg: some at bony prominences (greater trochanter, lateral malleolus, lateral epicondyle, lateral tibial plateau), some clustered on the thigh and shank (Fal-3,11-3, Fpl-3; Tal-3, T11-13). Additionally, two markers are placed on the foot at the lateral aspect of the calcaneus and base of the fifth metatarsal and one on the pelvis at theiliac crest). During the static activities (standing still, laying down) 7 additional markers are placed: medial malleolus, medial epicondyle, medial tibial plateau, medial and lateral superior patella, medial and lateral inferior patella. The eight markers nearest to the knee joint can be filled with Gadolinium, and can be be replaced at these same locations prior to the MR images (FIG. 15). The locations can be marked with a non-toxic marker-pen.

Reference Database

The reference database is typically a compendium of demographic and motion analysis data for all subjects whose data has been processed by a central processing site. This database can contain fields describing each of the subject's name, age, height, weight, injury types, orthopedic medical history, other anatomic measurements (thigh length, shank length, shoe size, etc.). The database can also contain the results of any and all gait analysis run on these patients. This can include, for all activities tested (walk, run, jog, etc.), a number of peak valves (peak knee flexing, peak hip adduction movement; toe-out, angle, etc). along with the motion trajectories of the limb segments while the subjects are performing different activities.

In order to obtain a typical motion profile, the sex, age, height, weight, limb length, and type of activity desired can be entered as an average into the database. The database searches for a set of subjects most closely watching the input average. From this set of data, a typical motion pattern is distilled and a data set is output. This data set can include, over a time interval, the motion characteristics: hip/knee/ankle/flexion/extension angles, knee/hip/ankle adduction/abduction angles, movement, stride length, cadence, etc. This data can then be used to drive an animation of the motion of the desired joint.

Process Image of Joint/Bones

Calculation of Limb Segment Parameters

Each limb segment (thigh, shank and foot) can idealized as a rigid body with a local coordinate system defined to coincide with a set of anatomical axes (the assumption of rigidity is dropped in calculating the location of the femur and tibia). The intersegmental moments and forces can be calculated from the estimated position of the bones, the ground reaction force measurements, and the limb segment mass/inertia properties. The moment at the knee can be resolved into a coordinate system fixed in a tibial reference system with axes defining flexion-extension, abduction-adduction, and internal-external rotation.

This approach provides results in a range of patients in a highly reproducible mariner. Typically the magnitudes of the moments are dependent on walking speed. To control for the influence of walking speed, the walking speed closest to 1 meter/second is used. This speed is within the normal range for the type of patients for which the invention is particularly useful. In addition to the gait trial collected at 1 meter/second, self-selected speeds can also be evaluated to give a good correlation between gait-quantitative estimates of joint load lines and other measures when using self-selected speeds. In order to test patients under their typical daily conditions, medications should not be modified prior to gait analyses.

Point Cluster Technique

The Point Cluster Technique (PCT) movement analysis protocol is an extensible and accurate approach to bone motion estimation. Basically, a number of retro-reflective markers (e.g. retro-reflective material from 3M, Corp.) are attached to each limb segment under observation. Multiple video cameras can acquire data with the subject standing still and during activities of interest. An over-abundance of markers on each limb segment is used to define a cluster coordinate system, which is tied to an anatomically relevant coordinate system calculated with the subject at rest.

The standard PCT transformations are described below. In short, each marker is assigned a unit mass and the inertia tensor, center of mass, principal axes and principal moments of inertia are calculated. By treating the center of mass and principal axes as a transformation, local coordinates are calculated. Another set of coordinate systems is established; limb segment specific anatomic landmarks are identified through palpation and a clinically relevant coordinate system defined. For the femur and tibia, these anatomic coordinate systems are shown in FIG. 12. The transformation from the reference cluster coordinate system to the anatomic coordinate system is determined with the subject at rest by vector operations. During an activity, the transformation from the global coordinate system to the cluster coordinate system is calculated at each time step. To place the anatomic coordinate in the global system during the activity, the reference coordinate system to anatomic system transformation is applied, followed by the inverse global coordinate system to cluster coordinate system transformation for each time step.

In the Point Cluster Technique (PCT) a cluster of N markers can be placed on a limb segment of the subject. The location vector of each marker in the laboratory coordinate system is denoted as G(i,t) for marker i, (i=1,2, . . . , N) at time t, $t_0 \leqq t \leqq t_f$. A unit weight factor is assigned to each marker for the purpose of calculating the center of mass, inertia tensor, principal axes and principal moments of inertia of the cluster of markers. The cluster center of mass and principal axes form an orthogonal coordinate system described as the cluster system. The local coordinates of each of the markers relative to this coordinate system are calculated. Then $$G(i,t)=C(t)+E(t)\cdot L(i,t)=T_c(t)\cdot L(i,t)\ i=1 \ldots N$$

where G(t) is a matrix of all marker coordinate vectors, C(t) is the center of mass of G(t), E(t) is the matrix of eigenvectors of the inertia tensor of G(t), and L(i,t) are the local coordinates of marker i.

These markers are observed by opto-electronic means while the subject performs activities and while standing completely still in a reference position. With the subject in this same reference position, a subset of the markers is observed relative to the underlying bones by other techniques, which might include x-rays, CT scan, or palpation.

The measured marker locations are defined with respect to the unobservable location and orientation of the bone by $$G(i, t) = P(t) + O(t) \cdot R(i, t) = T_b(t) \cdot R(i, t)$$

$$i=1\ N$$

where P(t) is the location and O(t) is the orientation of a coordinate system embedded in the bone and R(i,t), also unobservable, are the trajectories of the markers relative to the underlying rigid body coordinate system at time t. The bone and cluster systems are each orthogonal systems, related by the rigid body transformation $T_{bc}(t)$:

$$L(i,t)=T_{bc}(t)\cdot R(i,t)$$

substituting and eliminating R(i,t) yields $$T_b(t)=T_c(t)\cdot T_{cb}(t)$$

To maintain physical consistency, $T_{cb}(t)T_{bc}(t)^{-1}$ must be the inertia tensor eigendecomposition transformation of R(i,t). Once R(i,t) are specified, $T_{cb}(t)$ and subsequently $T_b(t)$ are calculable.

Point Cluster to Anatomic Coordinate System Transformation

From these equations one can also relate the global coordinate system with respect to a limb segment system. As an example of how these systems can be used to describe joint motion, one can consider the tibio-femoral joint. The motion that is of interest is how the femoral condyles move with respect to the tibial plateau. This is done by first defining a set of coordinate axes in the femoral condyles and the tibial plateau.

A coordinate system is located in both the femoral condyles and the tibial plateau. The femoral condyles medial-lateral (ML) axis runs through the trans-epicondylar line (TEL), a line drawn between the ML femoral epicondyles. The midpoint of this axis is the origin. The inferior-superior (IS) runs parallel to the long axis of the femur, passing through the midpoint of the TEL. The anterior-posterior (AP) is the cross product of the ML and IS axes. The tibial coordinate system begins with the ML axis running through the most medial and lateral edges of the plateau. The IS axis is perpendicular to the ML axis passing through the tibial eminence. The AP axis is the cross product of the ML and IS axes. These are known as the anatomic coordinate system ($A(t)_{thigh}$, $A(t)_{shank}$).

Relating the cluster system to the anatomic coordinate system is done by use of another transformation matrix. This is done by relating the thigh cluster to a cluster of markers, a sub cluster, that is related to the femoral condyles and femur (cluster to anatomic transformation).

$$R(t)_{thigh}=U(t)_{thigh}A(t)_{thigh}$$

The tibia has a similar transformation matrix.

$$R(t)_{shank}=U(t)_{shank}A(t)_{shank}$$

Therefore, from a cluster of markers in the global system, motion of the femur with respect to the tibia can be determined by:

$$TS(t)=A(t)_{thigh}\cdot G(t)_{thigh}\cdot R(t)_{shank}\cdot A(t)_{shank}$$

Here TS(t) is the motion of the thigh with respect to the shank.

Angles are calculated by a projection angle system, an axis from the femoral anatomic system and one from the tibia are projected onto a plane in the tibial coordinate system. For example, flexion/extension can be determined by projecting the IS axis of the femur and tibia onto the sagittal plane (AP-IS plane) of the tibia.

Validation of the Point Cluster Technique

The point cluster technique was evaluated as a method for measuring in vivo limb segment movement from skin placed marker clusters. An Ilizarov device is an external fixture where 5 mm diameter pins are placed directly into the bone on either side of a bony defect. The rigid external struts affixed to these pins form a rigid system fixed in the underlying bone. Two subjects were tested with Ilizarov fixation devices. One subject had the Ilizarov device placed on the femur and second subject had the device placed on the tibia. Each subject was instrumented with point clusters placed on the thigh and shank segment. In addition, markers were placed on the Ilizarov device to establish a system fixed in the underlying bone.

The relative angular movement and translational displacement between the system affixed in the bone and the point cluster coordinate system were calculated while ascending a 20-cm step (Step Test). Angular changes between the three orthogonal axes fixed in the bone versus three axes in the point cluster were calculated. The average difference over the trials for three axes were 0.95±1.26, 2.33±1.63, and 0.58±0.58 degrees. Similarly, the average error for the distance between coordinate systems was 0.28±0.14 cm. The second subject with the Ilizarov device placed on the femur could not perform the Step-Test, but was able to perform a weight-bearing flexion test where his knee flexed to approximately 20° from a standing position. The average change between the coordinate origin was 0.28±0.14 cm. The changes in axis orientation were 1.92±0.42, 1.11±0.69 and 1.24±0.16 degrees.

The simultaneously acquired motion for a coordinate system embedded in bone (Ilizarov system) and a set of skin-based markers was compared. At every time instant the location and orientation of the Ilizarov system, the rigid body model skin marker system, and the interval deformation technique skin marker system were determined. The change in the transformation from the Ilizarov system to one of the skin marker systems over time is a measure of the deformation unaccounted for in the skin marker system.

The interval deformation technique produced a substantial improvement in the estimate of the location and orientation of the underlying bone. For perfectly modeled motion there would be no relative motion between the Ilizarov system and the skin marker system over the time interval. The change in the transformation from the Ilizarov system to the skin marker systems are shown in FIGS. 14 and 15, for location and orientation respectively, for both a rigid body model and the interval deformation technique. For this single data set, the location error was reduced from 7.1 cm to 2.3 cm and the orientation error from 107 degrees to 24 degrees, with the error summed over the entire time interval. The subject performed a 10 cm step-up; the marker deformation was modeled as a single Gaussian function.

Deformation Correction

There are a number of algorithmic alternatives available to minimize the effects of skin motion, soft tissue deformation, or muscle activation that deform the externally applied markers relative to the underlying bone. The Point Cluster Technique decreases the effects of marker movement relative to the underlying bone through averaging. If more correction is required, one of a number of deformation correction techniques may be added. In order of increasing computational complexity and deformation correction ability, these are rigid body linear least square error correction, global optimization correction, anatomic artifact correlation correction and interval deformation correction.

An overview of the Interval Deformation Correction Technique is given below. In short, the technique provides a maximum likelihood estimate of the bone pose, assuming that each marker on a limb segment deforms relative to the underlying bone in some functional form. The technique parameterizes these functional forms and then performs a multi-objective non-linear optimization with constraints to calculate these parameters. This is an extremely computationally intensive technique, with the current instantiation of the algorithm requiring 6-8 hours per limb segment of running time on 266 MHz Pentium 2 computer.

Interval Deformation Technique

Since Tc can be calculated directly from the global coordinates of the markers, the remainder of this development only examines the determination of R(i,t) and subsequently $T_{cb}(t)$. For this reduced problem, the input data is the local coordinates in the cluster system L(i,t) for all i, $T_o \leqq t \leqq t_f$. It can be assumed that each marker has some parameterized trajectory, $d(a_{ij}, t)$, relative to the underlying bone at each time step, with independent and identically distributed noises v(i, j,t)

$$R_j(i, t)=d(a_{i,j}, t)+v(i, j, t)$$

$$j=1 \ldots 3$$

$$i=1 \ldots N$$

or, equivalently $$R(i, t)=F(a_i, t)+v(i, t)$$

$$i=1 \ldots N$$

where $a_{ij}$ is a vector of parameters for marker i, ordinate j; $a_i$ is a vector of parameters combining all of the parameters for all of the ordinates of marker i. Then the estimate of the data, M(i,t), can be given by $$M(i,t)=T_{bc}(t)\cdot R(i,t)$$

Without further restrictions the problem is indeterminate, as the locations of the markers in the bone system R(i,t) are never observable with the opto-electronic system. The indeterminate problem can be converted to a chi-squared estimate problem through a series of steps. An observation of the truly unobservables at the time boundaries is inferred; that is, it is assumed that $T_{cb}(t \leqq t_o)$ and $T_{cb}(t \geqq t_f)$ are observed. The value of $T_{cb}$ can be selected depending on the activity being studied. For example, consider the step up activity, where the subject starts and stops in the reference position. For this activity the body is not deforming outside the estimation interval; that is, the markers are not moving with respect to the bone:

$$T_{cb}(t<t_o)=T_{cb}(t=t_o) \text{ and } T_{cb}(t>t_f)=T_{cb}(t_f).$$

It can now be assumed that the noise functions v(i, j, t) are normal distributions with individual standard deviations a(i, j, t), the probability P(i,j,t) of the data for ordinate j, marker i, time t being a realization of the stochastic process is given by:

$$P(i, j, t) \propto \exp\left(-\frac{1}{2}\left(\frac{L(i, j, t)-M(i, j, t)}{\sigma(i, j, t)}\right)^2\right)$$

Provided the noise functions v(i, j, t) are independent of each other, the probability of the entire data set being a realization is a product of each of the individual probabilities:

$$P(i, j, t) \propto \prod_{i=l}^{N} \prod_{j=l}^{3} \prod_{t=t_o}^{f_i} \exp\left(-\frac{1}{2}\left(\frac{L(i, j, t)-M(i, j, t)}{\sigma(i, j, t)}\right)^2\right)$$

Maximizing this probability can be equivalent to minimizing the negative of its logarithm, yielding the familiar chi-square criteria. As an intermediate step the following error matrices can be defined:

$$X(a, t) \ni (X(a, t))_{i,j} = \left(\frac{L(i, j, t)-M(i, j, t))}{\sigma(i, j, t)}\right)^2$$

$$i=1 \ldots N$$

$$j=1 \ldots 3$$

$$X(a) = \sum_{t=t_o}^{t_f} X(a, t)$$

and seek a which in some sense minimizes X(a), a matrix whose elements represent the error over the entire time interval for each ordinate of each marker. If the normal noise distribution assumption is true, then this minimization results in, the maximum likelihood estimate of the parameterization, and by inference maximum likelihood estimate of the transformation from the bone system to the cluster system. If the normal noise assumption is not true, the chi-squared estimate is still appropriate for parameter estimation; the results cannot be interpreted as a maximum likelihood estimate, but, for example, confidence regions on the estimate or the formal covariance matrix of the fit can be determined.

Obtaining the parameter set a is a computationally complex operation. The approach taken was to define a scalar to represent this entire error matrix, $$f(a) = \sum_{i=l}^{N} \sum_{j=i}^{3} (X(a))_{i,j}$$

and seek a that minimizes f(a).

The limits on marker motion previously discussed can now be converted into deformation constraints, which allow the formulation of the problem as a general non-linear programming problem. The constraints arise from two sources; human limb segments do not deform outside a small range, and the locations of the markers are chosen with specific properties in mind. For computational purposes, the deformation constraints are selected to be:

1. The axes of the cluster system moves by less than 15 degrees relative to the bone system.
2. The center of mass of the cluster system moves by less than 3 cm relative to the bone system.
3. The markers move by less than 4 cm relative to the bone system.
4. Each of the principal moments of inertia of the cluster system change by less than 25 percent from the reference values.

The Point Cluster Technique marker set was designed to ensure that the cluster of points is non-coplanar and possess no axes of rotational symmetry. These properties ensure a local coordinate system that is well defined and unambiguous over the entire time interval. The constraints are then:

5. The ratio of the smallest principal moment of inertia of the cluster system to the largest is more than 5 percent; the magnitude of the smallest principal moment of inertia of the cluster system is greater than some small positive value.
6. The principal moments of each axis are different from each other by at least 5 percent.

The general problem can then be formulated:

Minimize f(a)

$$a \epsilon R^D$$

Subject to:

$g_i(a)=0 i=1 \ldots m_e$ $g_i(a) \leqq 0 i=m_e+1 \ldots m$ $a_1 \leqq a \leqq a_u$ where D is the total number of parameters; $m_e$, the number of equality constraints, is 0; and m, the total number of constraints, is 10.

The approach taken to verify the operation of the algorithm implementation began with generating a set of 50 synthetic data sets with known characteristics. The program was then applied to all of the data sets. The program results were then compared to the known, generated deformation. Error results were calculated for both the interval deformation technique descried herein and for the standard rigid body model formulation.

The 50 trial data sets were processed through the algorithm. The results over all of the trial sets are summarized in Table 1, where the center of mass and direction cosine error of the interval deformation technique and the rigid body model are compared. After processing by the interval deformation algorithm the center of mass error has been reduced to 29% and the direction cosine error has been reduced to 19% of the rigid body model error. In a t-test for paired samples, both of these decreases were significant at $p<0.001$.

Validation of the Interval Deformation Correction Technique

A subject fitted with an Ilizarov external fixation was observed with the optoelectronic system. The Point Cluster Marker set was affixed to the subject's shank (6 markers), along with a set of four markers rigidly attached to the Ilizarov device, which is rigidly connected to the tibia with bone pins. These four markers define a true bone embedded coordinate system. Data were acquired by GaitLink software (Computerized Functional Testing Corporation) controlling four Qualisys cameras operating at a video frequency of 120 Hz. Three dimensional coordinates were calculated using the modified direct linear transform.

The subject was a 46 year old male (height 1.75 m, weight 84.1 kg) fitted with a tibial Ilizarov external fixation device. The device was rigidly attached to the tibia with nine bone pins, located in three sets (top, middle, and bottom) of three (medial, anterior, and lateral). The clinical purpose of the device was tibial lengthening; the test on the subject was performed two days prior to final removal of the device. The subject exhibited a limited range of motion and was tested performing a 10 cm step-up onto a platform.

The simultaneously acquired motion for a coordinate system embedded in bone (Ilizarov system) and a set of skin-based markers was compared. At every time instant the location and orientation of the Ilizarov system, the rigid body model skin marker system, and the interval deformation technique skin marker system was determined. The change in the transformation from the Ilizarov system to one of the skin marker systems over time is a measure of the deformation unaccounted for in the skin marker system.

The interval deformation technique produced a substantial improvement in the estimate of the location and orientation of the underlying bone. For perfectly modeled motion there would be no relative motion between the Ilizarov system and the skin marker system over the time interval. The change in the transformation from the Ilizarov system to the skin marker systems are shown in FIGS. 14 and 15 for location and orientation respectively, for both a rigid body model and the interval deformation technique. For this single data set, the location error was reduced from 7.1 cm to 2.3 cm and the orientation error from 107 degrees to 24 degrees, with the error summed over the entire time interval. The subject performed a 10 cm step-up; the marker deformation was modeled as a single Gaussian function.

CORRELATING RESULTS FROM GAIT ANALYSIS AND GEOMETRICAL REPRESENTATIONS OF THE BONE

In correlating the load pattern obtained from a gait analysis using, e.g. the PCT, with the geometrical representation of the bone from the segmented MRI data, one can be guided by the general process as described below. The process allows for dynamic visualization (i.e. animations) of high-resolution geometrical representations derived from MRI scans (or other imaging techniques). The motion of the subject specific anatomic elements is generally driven by data acquired from the motion (gait) lab. Fidelity of these animations requires calculation and application of a sequence of rigid body transformations, some of which are directly calculable and some of which are the result of optimizations (the correction for skin marker deformation from rigidity does not use the rigid body assumption, but generates a correction that is applied as a rigid body transform).

The process comprises:

a) acquiring data from MRI (or other imaging techniques), and PCT gait protocols;
b) directly calculating a set of transformations from the data;
c) calculating a set of transformations from optimizations, as needed;
d) generating a 3D geometric representation of the anatomic element from the MR data; and
e) applying the transformations of (b) and (c) to the 3D geometric representation.

Each of these steps are described in detail below.

Acquiring the Data from MRI (or other imaging techniques) and PCT Gait Protocols In the Point Cluster Technique (PCT) protocol, a patient can have a number of retro-reflective markers attached to each limb segment under observation. Multiple video cameras acquire data with the subject standing still and during activities of interest.

In addition, in order to correspond activities in the gait lab with the MRI scans, another reference data set (subject standing still, prescribed posture) can be acquired using 8 additional markers clustered about the knee. These markers are filled with gadolinium-DTPA and covered with a retro-reflective material to allow for correlation between the MRI image and the video data.

Directly Calculating a Set of Transformations from the Data

The transformations are described in detail in [Andriacchi T P, Alexander E J, Toney M K, Dyrby C O, Sum J. J Biomech Eng 1998; 120(12): 743-749]. In short, each marker can be assigned a unit mass and the inertia tensor, center of mass, principal axes and principal moments of inertia can be calculated. By treating the center of mass and principal axes as a transformation, local coordinates arcan be e calculated. Another set of coordinate systems can also be required for this technique; limb segment specific anatomic landmarks can be identified through palpation and a clinically relevant coordinate system can be defined. The required transformations are summarized in Table 1 below.

Calculating a Set of Transformations from Optimizations

There are three required transformations:

Optimization 1. One can calculate the linear least square error rigid body transformation from the MRI common local coordinate system to the VID common local coordinate system.

Optimization 2. For each limb segment, one can calculate the linear least square rigid body transformation from the MRI limb segment anatomic coordinate system to the video limb segment anatomic coordinate system (obtained from the gait analysis), using a subset of common markers appropriate for each segment.

Optimization 3. One can calculate a correction for the deviation of the limb segment from rigidity during each time step of the activity, using the PCT with either the mass redistribution [Andriacchi T P, Alexander E J, Toney M K, Dyrby C O, Sum J. J Biomech Eng 1998; 120(12): 743-749] or interval deformation algorithms [Alexander E J, Andriacchi T P: Correcting for deformation in skin-based marker systems. Proceedings of the 3rd Annual Gait and Clinical Movement Analysis Meeting, San Diego, Calif., 1998].

Generating a 3D Geometric Representation of the Anatomic Element from the MR Data The MR slices are segmented for the multiple anatomic and fiducial elements. The slices are combined to a voxel representation. An isosurface can be calculated from the boundary voxel elements. A tessellation of the isosurface can be calculated, along with the outward pointing normal for each surface element. This data can then be stored in a standard 3D graphic format, the Virtual Reality Modeling Language (VRML).

Appling the Transformation Sequence to the Geometric Representation

The transformation sequence is provided below in Table 1. This transformation sequence can be applied to each of the anatomic elements over each time step of the activity, starting with sequence 6.

TABLE 1

| SEQ | FROM SYSTEM | To SYSTEM | XFORM |
|---|---|---|---|
| 1 | MR Global | MR Local | ED1 |
| 2 | MR Local | Common Local | OPT1 |
| 3 | Common Local | MR Anatomic | ANA2 |
| 4 | MR Anatomic | VID Anatomic | OPT2 |
| 5 | VID Anatomic | VID Ref | ANA3 |

TABLE 1-continued

| SEQ | FROM SYSTEM | To SYSTEM | XFORM |
|---|---|---|---|
| 6 | VID Ref | VID Deformed(t) | ED3 |
| 7 | VID Deformed(t) | VID Bone(t) | OPT3 |
| 8 | VID Bone(t) | VID Global(t) | ED4 |

Correlating Marker Sets

As pointed out at numerous places in the specification, the use of external reference markers that are detectable by both MRI and optical techniques can be an important and useful tool in the method of this invention. The use of the reference markers can form the basis for an aspect of this invention that is a method for correlating cartilage image data, bone image data, and/or optoelectrical image data for the assessment of the condition of a joint of a human. This method comprises, obtaining the cartilage image data of the joint with a set of skin reference markers placed externally near the joint, obtaining the bone image data of the joint with a set of skin reference markers placed externally near the joint, obtaining the external bone image data optoelectrical image data of the joint with a set of skin reference markers placed externally near the joint. Using the skin reference markers, one can then correlate the cartilage image, bone image and opto-electrical image with each other, due to the fact that each skin reference marker is detectable in the cartilage, bone and opto-electrical data. The cartilage image data and the bone image data can be obtained by magnetic resonance imaging, positron emission tomography, single photon emission computed tomography, ultrasound, computed tomography or X-ray. Typically, MRI will be preferred. In the case of X-ray, further manipulations must be performed in which multiple X-ray images are assimilated by a computer into a 2 dimensional cross-sectional image called a Computed Tomography (CT) Scan. The opto-electrical image data can be obtained by any means, for example, a video camera or a movie camera. Multiple skin reference markers can be placed on one or more limbs of the patient prior to imaging. The skin reference markers are described hereinbefore.

By a sequence of calculations a set of transformations that will take the subject specific geometric representation of anatomic elements determined from the MR image set to the optical reference coordinate system. From the optical reference coordinate system, the standard Point Cluster Technique transformation sequence is applied to generate dynamic visualizations of these anatomic elements during activities previously recorded in the motion lab. Fidelity of these dynamic visualizations (and subsequent contact surface determination) requires the calculation and application of a sequence of rigid body transformations. Some of these are directly calculable and some are the result of optimizations (the correction for skin marker deformation from rigidity does not use the rigid body assumption, but generates a correction that is applied as a rigid body transform).

The first required transformation can be from the MR global coordinate system to the MR center of mass/principal axis coordinate system. This can be done by calculating the center of mass of each of the individual markers, resulting in a set of eight three dimensional points. Each of these points can be assigned a unit mass, and the center of mass, inertia tensor, and principal axes can be calculated. The same procedure can be performed on these markers as determined by the optical system, providing a transformation from the optical global system to a center of mass/principal axis system.

If the relative orientation of the tibia and femur as determined by the MR system and the optical system are identical, it is only necessary to apply the optical reference system to the anatomic system transformation of the MR local data. If this is not the case, an optimization calculation can be performed to determine the rotation and translation of, for example, the femur with respect to the tibia. One then can calculate the linear least square rigid body transformation from the MR limb segment anatomic coordinate system to the video limb segment anatomic coordinate system prior to applying the Point Cluster Transformations.

Figure 18A:
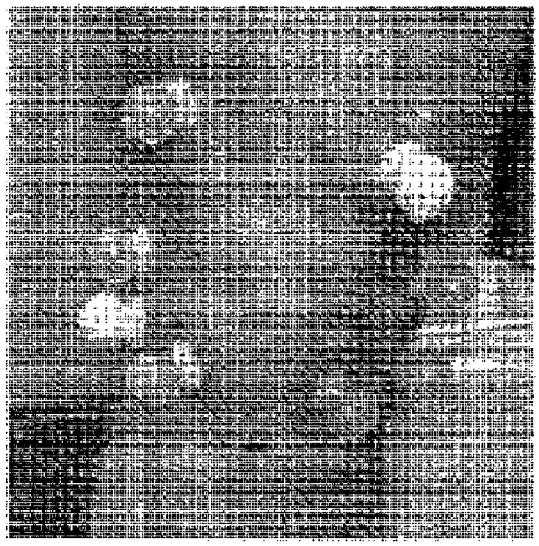
FIGS. 18A-18I show functional joint imaging.
Figure 18B:
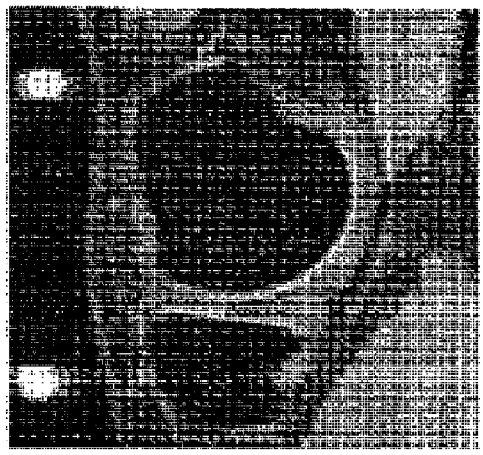
Figure 18C:
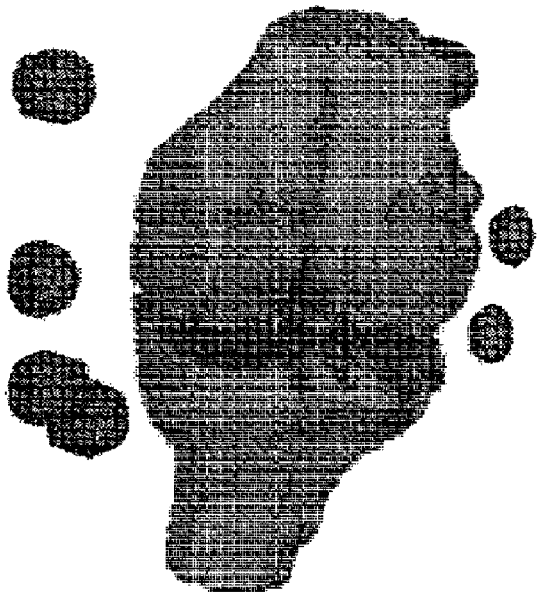
Figure 18F:
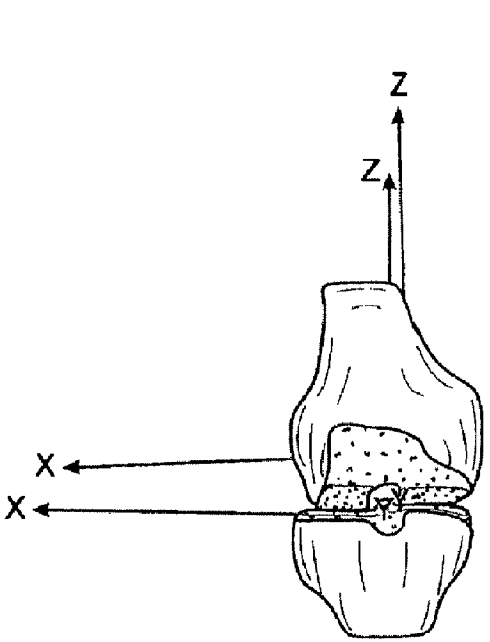
Figure 18E:
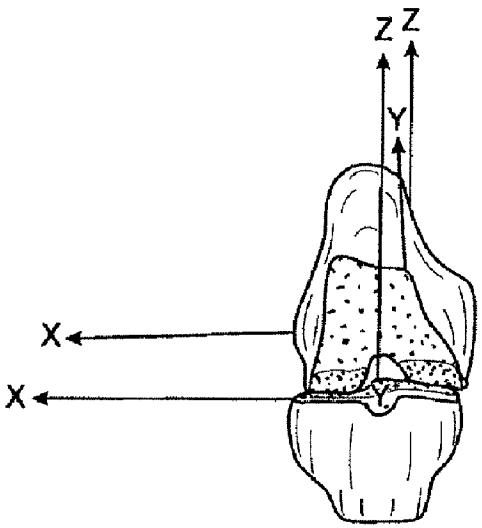
Figure 18D:
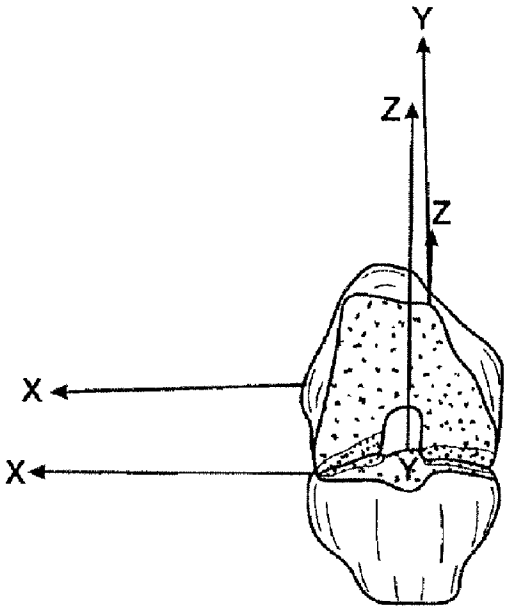
Figure 18I:
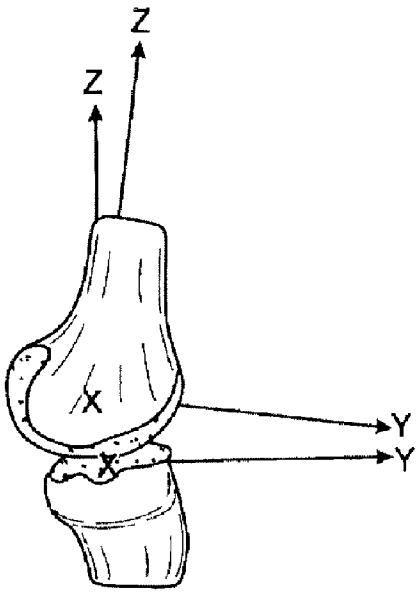
Figure 18H:
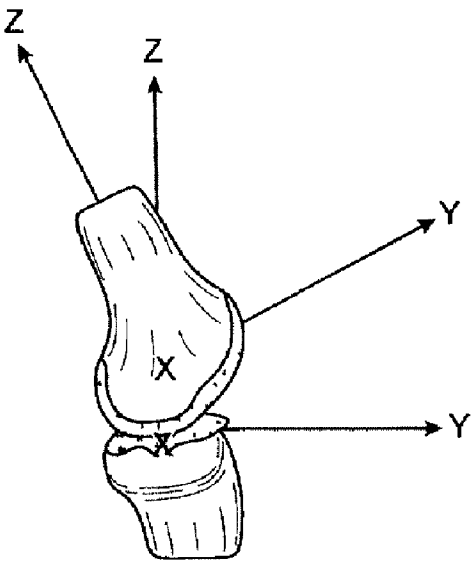
Figure 18G:
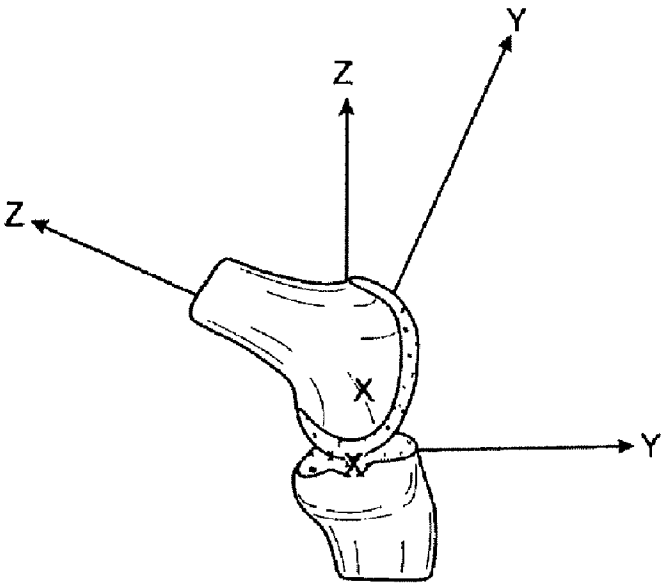

For visualization or contact surface determination, one can examine the relative motion of one segment to the other, for example the motion of the femur relative to a fixed tibial frame. This can be accomplished by applying the global to tibial anatomic system transform to all of the elements. An example of this type of visualization is given in FIG. 18. The Figure shows what can be referred to as functional joint imaging. FIG. 18A is a photograph demonstrating the position of the external markers positioned around the knee joint. The markers are filled with dilute Gd-solution. B is Sagittal 3D SPGR image through the medial femorotibial compartment. Two of the external markers are seen anteriorly as rounded structures with high signal intensity. C is 3D reconstruction of femoral and tibial bones (light grey), external markers (dark grey), femoral cartilage (red), and tibial cartilage (blue) based on the original SPGR MR images. D-I show a functional joint imaging sequence at selected phases of leg extension from a seated position, D-F, anterior projection. The vectors represent the relative location and orientation of the femur with respect to the tibia. G-I is a lateral projection. These dynamic visualizations can be used to demonstrate tibiofemoral contact areas during various phases if gait or other physical activities.

Figure 19:
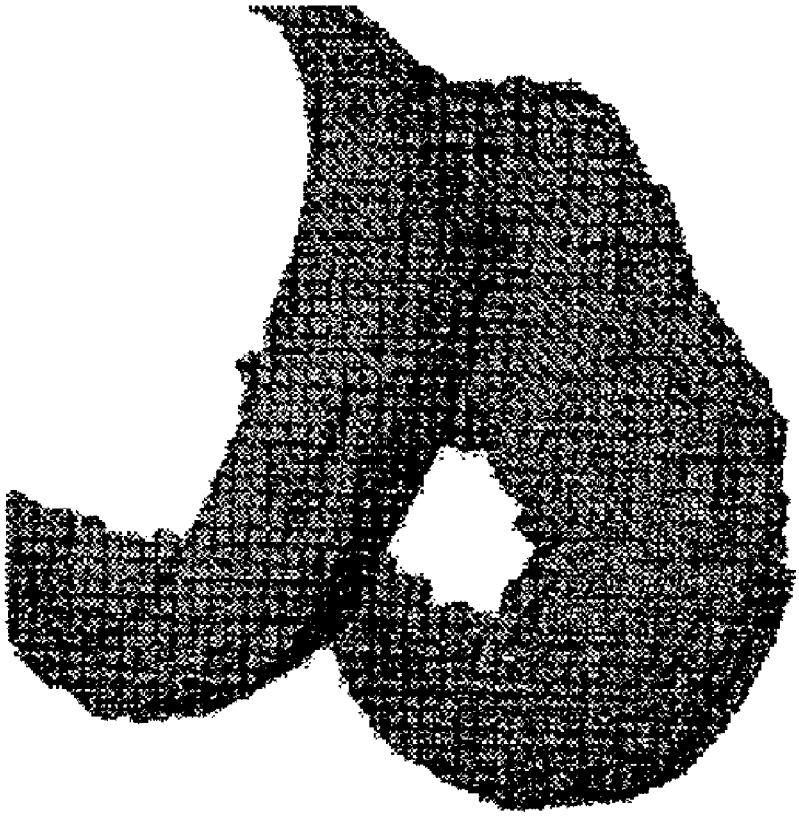
FIG. 19 shows the superimposition of the tibiofemoral contact line onto the 3D cartilage thickness map.

Superimposition of Cartilage Thickness Map onto Subject Specific Anatomic Model and Determination of Distance of Cartilage Defect from Load Bearing Line Superimposing the cartilage thickness maps onto the subject specific geometric models can follow the same approach taken to bring the MR generated geometries into the optical reference system. Since the thickness maps and the geometric models are initially in the same coordinate system; one possible approach is to perform a simple surface mapping of the thickness map onto the geometric model. Another alternative approach is to convert the thickness map directly into a geometric representation (FIG. 19).

Once the thickness map is embedded in the femoral geometry, one can define a scalar metric that characterizes the location of any cartilage lesions relative to the point of contact line. One approach is a simple 3D distance along the surface from the center of the cartilage lesion to the point of closest approach of the contact line. Another metric that could be useful would be to multiply the area of the lesion by the adduction moment at that time instant, then divide by the distance from lesion center to point of closest approach. This could result in a metric that increases with lesion area, adduction moment, and closeness of approach.

Display Correlated Images

Determination of Anatomic and Natural Reference Lines

There are two alternative approaches one can consider for determining a reference line on the cartilage surfaces. One skilled in the art will easily recognize other approaches that can be suitable for this purpose. The first approach is based on anatomic planes; the second is a natural approach building on the three dimensional cartilage thickness map.

The location of the pathway of loading relative to the femoral and tibial anatomy and geometry can be assessed by defining sagittal planes bisecting the medial femoral condyle, the lateral femoral condyle, the medial tibial plateau, and the lateral tibial plateau. For the medial femoral condyle, the operator can manually delete surface points located along the trochlea. Then, a sagittal plane parallel to the sagittal midfemoral plane can be defined through the most medial aspect of the medial femoral condyle followed by a sagittal plane parallel to the sagittal midfemoral plane through the most lateral aspect of the medial femoral condyle. The sagittal plane that is located halfway between these two planes can be defined as the "midcondylar sagittal plane". The intersection between the midcondylar sagittal plane and the external cartilage surface yields the "anatomic midcondylar cartilage line". The location of the pathway of loading can be assessed relative to the anatomic midcondylar cartilage line of the medial femoral condyle. The identical procedure can be repeated for the lateral femoral condyle.

The following method can be used for the medial tibial plateau: A plane parallel to the sagittal tibial plateau plane can be defined through the most medial point of the medial tibial plateau. A parallel plane located halfway between this plane and the sagittal tibial plateau plane can yield the "midsagittal plane of the medial tibial plateau." The intersection of the midsagittal plane of the medial tibial plateau and the external cartilage surface can yield the "anatomic midtibial plateau cartilage line" of the medial tibial plateau. The identical procedure can be repeated for the lateral tibial plateau.

Figure 20:
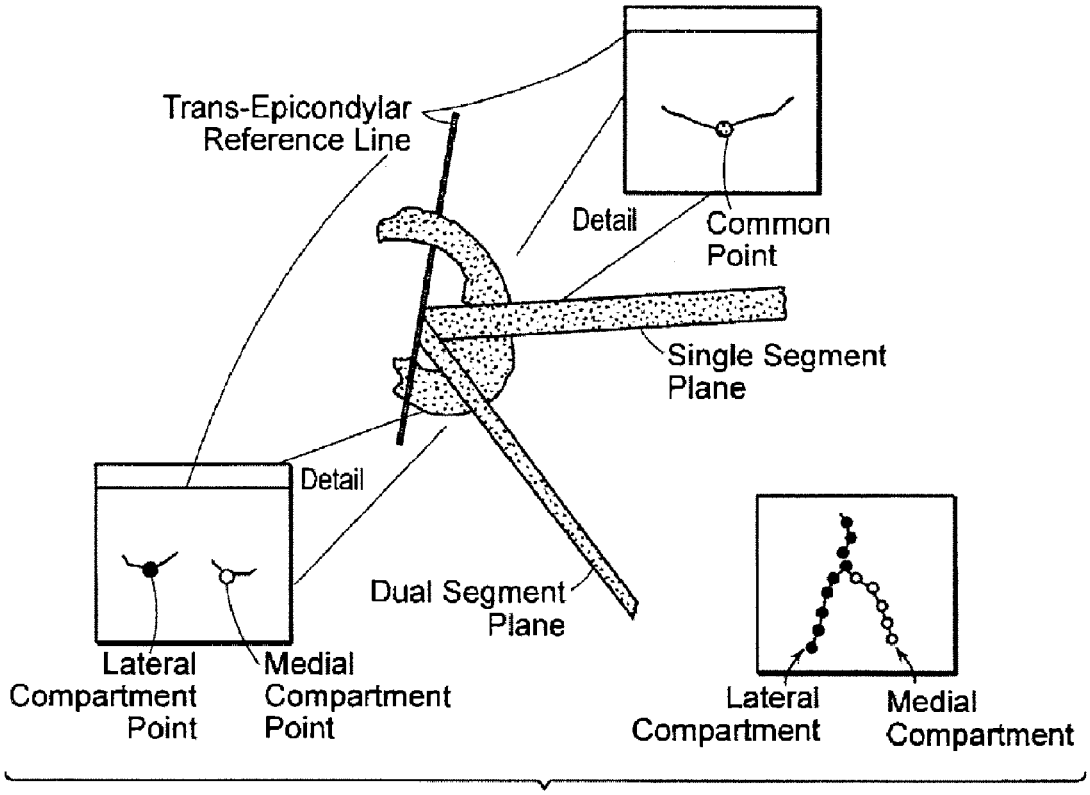
FIG. 20 shows the determination of the natural line of curvature as the cutting plain is rotated about the transepicondyear reference, the cartilage-plain intersection results in a curve.

In the second approach, one can calculate a "natural" line of curvature for each femoral cartilage component (FIG. 20). Intuitively, if one could roll the femoral condyles along a hard, flat surface, the line of contact with the flat surface would be the natural line of curvature. One can compare the actual tibiofemoral contact line to this reference line. Since one cannot physically remove the femur and roll it around, one can apply some geometric calculations to estimate this reference line. One can begin with the trans-epicondylar reference line previously described. One can then generate a plane coincident with this line oriented in an arbitrary initial position. The intersection of this plane and the external surface of the cartilage will produce a curve. One can then take the point furthest from the trans-epicondylar reference line as the natural contact point for this plane location. The next step is to rotate the plane by some increment, for example by one degree, and repeat the procedure. The operator can identify the rotation angles where the plane is intersecting the distinct medial—lateral compartments of the cartilage, and two points can be chosen, one from the medial femoral condyle and one from the lateral femoral condyle. If cartilage defects are present, in which case a compartment will not intersect in a curve but in a set of points, one can fit a spline through the points, then take the peak point of the spline as the contact point.

This can be repeated for the entire extent of the cartilage, resulting in a set of points that branch at the intercondylar notch. One can treat these points as two lines, and fit them with two splines. These can be the "natural" lines of curvature for each compartment.

Load Bearing Line Determination

Figure 21:
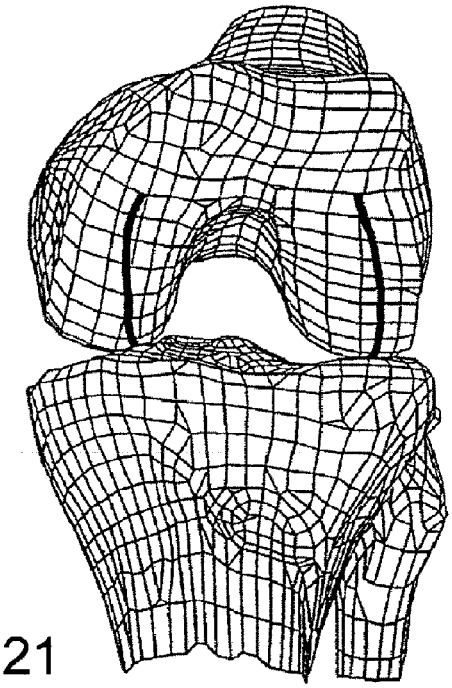
FIG. 21 shows the determination of the tibiofemoral contact line through the proximity detection and approach algorithm.

The calculations in this section can begin with the relative motion of the subject specific femoral anatomy with respect to the subject specific tibial anatomy, and end with a line describing the point of closest approach between the femur and tibia during some activity of daily living. A number of approaches to this problem have been described in the literature; Crosset, Dennis, Stiehl, and Johnson have all described techniques which might be applicable. One can implement a proximity detection and approach algorithm (PDAA) as it was specifically designed to work with the Point Cluster Technique (albeit with prosthetic knee joint components). Physically, the tibial and femoral cartilage components deform under load, leading in general to a contact patch between opposing surfaces. As the geometric models are rigid, they will not deform under this load, but will instead intersect in a non-realizable manner. The PDAA has been designed to incrementally displace and rotate one of the surfaces until a realizable contact is achieved. It is understood that this is not a true point contact line, but rather a reproducible representation of contact location (FIG. 21).

The MR generated subject specific geometries can be used to detect rigid body contact proximity when the subject is in full extension. The femoral component can then be incrementally displaced until simultaneous medial and lateral condyle contact occur. This is a first order approximation to the location of the contact point; slip velocity calculations can then be used to determine the final estimate of the contact point. The next time step in the activity can now be examined, using the previous time step solution as a starting point for the calculation. The full extension time step can be chosen to match with the static reference posture; should it be necessary, one can add in other reference postures.

Once the contact points have been determined for all time steps of the activity, one can map the locations of these points onto the femoral cartilage. A coordinate system can be defined on the surface of the femoral cartilage, choosing as a reference line the point of contact the femoral component would have had were it rolled along a flat plane. This allows one to determine a contact line relative to the subject specific anatomy.

Provide Therapy

A 2D or 3D surface registration technique can be used as an aid to providing therapy to match the anatomic orientation of the cartilage thickness map of a baseline and follow-up scan of a patient. The re-registered cartilage thickness map of the follow-up scan can then be subtracted from the baseline scan. This will yield the thickness difference, i.e. cartilage loss, as a function of x, y, and z. This can also be expressed as percentage difference.

The invention provides for techniques to assess biomechanical loading conditions of articular cartilage in vivo using magnetic resonance imaging and to use the assessment as an aid in providing therapy to a patient. In one embodiment, biomechanical loading conditions can be assessed in normal articular cartilage in various anatomic regions. In the knee joint, these anatomic regions include the posterior, central, and anterior medial femoral condyle, the posterior, central, and anterior medial tibial plateau, the posterior, central, and anterior lateral femoral condyle, the posterior, central, and anterior lateral tibial plateau, the medial and lateral aspect of the trochlea, and the medial and lateral facet and the median ridge of the patella. Since biomechanical loading conditions are assessed in vivo based on the anatomic features of each individual patient, a risk profile can be established for each individual based on the biomechanical stresses applied to cartilage. In this fashion, patients who are at risk for developing early cartilage loss and osteoarthritis can be identified. For example, patients with a valgus or varus deformity of the knee joint will demonstrate higher biomechanical stresses applied to the articular cartilage in the medial femorotibial or lateral femorotibial or patellofemoral compartments than patients with normal joint anatomy. Similarly, patients with disturbances of joint congruity will demonstrate higher biomechanical stress applied to certain regions of the articular cartilage. Such disturbances of joint congruity are often difficult to detect using standard clinical and imaging assessment. The amount of stress applied to the articular cartilage can be used to determine the patient's individual prognosis for developing cartilage loss and osteoarthritis. In another embodiment, biomechanical loading conditions can be assessed in normal and diseased articular cartilage. An intervention that can alter load bearing can then be simulated. Such interventions include but are not limited to braces, orthotic devices, methods and devices to alter neuromuscular function or activation, arthroscopic and surgical procedures. The change in load bearing induced by the intervention can be assessed prior to actually performing the intervention in a patient. In this fashion, the most efficacious treatment modality can be determined, For example, a tibial osteotomy can be simulated in the manner and the optimal degree of angular correction with regard to biomechanical loading conditions of normal and diseased cartilage can be determined before the patient will actually undergo surgery.

Estimation of biomechanical forces applied to normal cartilage can be used to determine a patient's risk for developing cartilage loss and osteoarthritis. Estimation of forces applied in and around a cartilage defect can be used to determine the prognosis of a cartilage defect and to guide the choice of therapy, e.g. treatment with chondroprotective or chondroregenerative agents, osteochondral allografting, cartilage transplantation, femoral or tibial osteotomy, or joint replacement surgery.

Having now provided a full discussion of various aspects of the technology relating to this invention, several further aspects of the invention can be seen.

One aspect of the invention is a method of assessing the condition of a joint in a mammal. The method comprises:

(a) comparing the movement pattern of the joint with the cartilage degeneration pattern of the joint; and (b) determining the relationship between the movement pattern and the cartilage degeneration pattern Another aspect of the invention is a method for monitoring the treatment of a degenerative joint condition in a mammal. The method comprises (a) comparing the movement pattern of the joint with the cartilage degeneration pattern of the joint;

(b) determining the relationship between the movement pattern and the cartilage degeneration pattern;

(c) treating the mammal to minimize further degeneration of the joint condition; and (d) monitoring the treatment to the mammal.

Still another aspect of the invention is a method of assessing the rate of degeneration of cartilage in the joint of a mammal, wherein the joint comprises cartilage and the bones on either side of the cartilage, which method comprises (a) obtaining a cartilage degeneration pattern of the joint that shows an area of greater than normal degeneration, (b) obtaining a movement pattern of the joint that shows where the opposing cartilage surface contact, (c) comparing the cartilage degeneration pattern with the movement pattern of the joint, and (d) determining if the movement pattern shows contact of one cartilage surface with a portion of the opposing cartilage surface showing greater than normal degeneration in the cartilage degeneration pattern.

Another aspect of the specification is a method for assessing the condition of the knee joint of a human patient, wherein the knee joint comprises cartilage and associated bones on either side of the joint. The method comprises (a) obtaining the patient's magnetic resonance imaging (MRI) data of the knee showing at least the cartilage on at least one side of the joint, (b) segmenting the MRI data from step (a), (c) generating a geometrical or biochemical representation of the cartilage of the joint from the segmented MRI data, (d) assessing the patient's gait to determine the cartilage surface contact pattern in the joint during the gait assessment, and (e) correlating the contact pattern obtained in step (d) with the geometrical representation obtained in step (c).

Still another aspect of this invention is a method for assessing the condition of the knee joint of a human patient, wherein the knee joint comprises cartilage and associated bones on either side of the joint. The method comprises (a) obtaining the patient's magnetic resonance imaging (MRI) data of the knee showing at least the bones on either side of the joint, (b) segmenting the MRI data from step (a), (c) generating a geometrical representation of the bone of the joint from the segmented MRI data, (d) assessing the patient's gait to determine the load pattern of the articular cartilage in the joint during the gait assessment, (e) correlating the load pattern obtained in step (d) with the geometrical representation obtained in step (c).

Another aspect of this invention is a method for deriving the motion of bones about a joint from markers placed on the skin, which method comprises (a) placing at least three external markers on the patient's limb segments surrounding the joint, (b) registering the location of each marker on the patient's limb while the patient is standing completing still and while moving the limb, (c) calculating the principal axis, principal moments and deformation of rigidity of the cluster of markers, and (d) calculating a correction to the artifact induced by the motion of the skin markers relative to the underlying bone.

Another aspect of the invention is a system for assessing the condition of cartilage in a joint of a human, which system comprises (a) a device for electronically transferring a cartilage degeneration pattern for the joint to receiving device located distant from the transferring device;

(b) a device for receiving the cartilage degeneration pattern at the remote location;

(c) a database accessible at the remote location for generating a movement pattern for the joint of the human wherein the database includes a collection of movement patterns for human joints, which patterns are organized and can be accessed by reference to characteristics such as type of joint, gender, age, height, weight, bone size, type of movement, and distance of movement;

(d) a device for generating a movement pattern that most closely approximates a movement pattern for the human patient based on the characteristics of the human patient;

(e) a device for correlating the movement pattern with the cartilage degeneration pattern; and (f) a device for transmitting the correlated movement pattern with the cartilage degeneration pattern back to the source of the cartilage degeneration pattern.

In each of these aspects of the invention it is to be understood that a cartilage degeneration pattern may be, i.a., 2D or 3D thickness map of the cartilage or a biochemical map of the cartilage.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating including evaluating the joint along one or more vectors tangent or perpendicular to the cartilage or bone surface; and selecting a therapy based on said three-dimensional evaluation.

2. The method of claim 1, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

3. The method of claim 1, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

4. The method of claim 1, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

5. The method of claim 1, wherein said electronically evaluating further comprises:

estimating the change of cartilage in a joint of a mammal over time, which method comprises, estimating the thickness or width or area or volume of a region of cartilage at an inital time $T_1$, estimating the thickness or width or area or volume of the region of cartilage at an later time $T_2$, and determining the change in the thickness or width or area or volume of the region of cartilage between the initial and the later times.

6. The method of claim 1, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the area of abnormally joint cartilage by identifying the areas having altered amounts of the biochemical component present.

7. The method of claim 1, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

8. The method of claim 1, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

9. The method of claim 1, wherein said electronic image data provides information on the thickness, shape, or curvature of said normal and said diseased tissue or the location and size of said diseased tissue.

10. The method claim 1, wherein said therapy comprises autologous chondrocyte transplantation, osteochondral allografting, osteochondral autografting, an implant, a replacement material, a scaffold, a regenerating material, a repair system, tibial corticotomy, femoral osteotomy or tibial osteotomy.

11. The method of claim 1, wherein said therapy uses cartilage or bone tissue grown ex vivo, stem cells, an artificial non-human material, an agent that stimulates repair of said diseased tissue, or an agent.

12. The method of claim 1, wherein said information is used to determine the thickness or other geometrical feature of a tissue transplant, a tissue graft, a tissue implant, a tissue replacement material, a tissue scaffold, or a tissue regenerating material or tissue repair system.

13. The method of claim 1, wherein said image is obtained using ultrasound, computed tomography, positron emission tomography, a single photon emission computed tomography scan, or MRI.

14. The method of claim 13, wherein said information is used to generate a three-dimensional representation of cartilage thickness or a physical model of said normal or said diseased tissue or both.

15. The method of claim 14, wherein said physical model is used to shape a tissue transplant, a tissue graft, a tissue implant, a tissue replacement material, a tissue scaffold or a tissue regenerating material or tissue repair system.

16. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating including evaluating the joint along one or more vectors tangent or perpendicular to the cartilage or bone surface; and determining at least one of size and shape for at least one of a transplant, a graft, an implant, a replacement material, a scaffold, a regenerating material and a repair system based on said three dimensional evaluation.

17. The method of claim 16, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

18. The method of claim 16, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

19. The method of claim 16, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

20. The method of claim 16, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of a region of cartilage at a later time $T_2$, and determining the change in the thickness or width or area or volume of the region of cartilage between the initial and the later times.

21. The method of claim 16, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the areas having altered amounts of the biochemical component present.

22. The method of claim 16, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, identifying the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

23. The method of claim 16, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

24. The method of claim 16, wherein said electronic image provides information on the thickness, shape, or curvature of said normal and said diseased tissue or the location and size of said diseased tissue.

25. The method claim 16, wherein said articular repair comprises autologous chondrocyte transplantation, osteochondral allografting, osteochondral autografting, tibial corticotomy, femoral or tibial osteotomy.

26. The method of claim 16, wherein said articular repair uses cartilage or bone tissue grown ex vivo, stem cells, an artificial non-human material, an agent that stimulates repair of said diseased tissue, or an agent.

27. The method of claim 16, wherein said information is used to determine the thickness or other geometrical feature of a tissue transplant, a tissue graft, a tissue implant, a tissue replacement material, a tissue scaffold, or a tissue regenerating material or tissue repair system.

28. The method of claim 16, wherein said image is obtained using ultrasound, computed tomography, positron emission tomography, a single photon emission computed tomography scan, or MRI.

29. The method of claim 28, wherein said information is used to generate a three-dimensional representation of cartilage thickness or a physical model of said normal or said diseased tissue or both.

30. The method of claim 29, wherein said physical model is used to shape a tissue transplant, a tissue graft, a tissue implant, a tissue replacement material, a tissue scaffold or a tissue regenerating material or tissue repair system.

31. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating including evaluating the joint along one or more vectors tangent or perpendicular to the cartilage or bone surface; and designing a therapy based on said three dimensional evaluation.

32. The method of claim 31, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

33. The method of claim 31, wherein said electronically evaluating further comprises:

assessing the condition of cartilage in a joint of of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

34. The method of claim 31, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

35. The method of claim 31, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of a region of cartilage at an later time $T_2$, and determining the change in the thickness or width or area or volume of the region of cartilage between the initial and the later times.

36. The method of claim 31, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the area of abnormally joint cartilage by identifying the areas having altered amounts of the biochemical component present.

37. The method of claim 31, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, identifying the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

38. The method of claim 31, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

39. The method of claim 31, wherein said electronic data provides information on the thickness, shape, or curvature of said normal and said diseased tissue or the location and size of said diseased tissue.

40. The mehtod of claim 31, wherein said therapy comprises autologous chondrocyte transplantation, osteochondral allografting, osteochondral autografting, an implant, a replacement material, a scaffold, a regenerating material and a repair system, tibial corticotomy, femoral or tibial osteotomy.

41. The method of claim 31, wherein said therapy uses cartilage or bone tissue grown ex vivo, stem cells, an artificial non-human material, an agent that stimulates repair of said diseased tissue, or an agent.

42. The method of claim 31, wherein said information is used to determine the thickness or other geometrical feature of a tissue transplant, a tissue graft, a tissue implant, a tissue replacement material, a tissue scaffold, or a tissue regenerating material or tissue repair system.

43. The method of claim 31, wherein said image is obtained using ultrasound, computed tomography, positron emission tomography, a single photon emission computed tomography scan, or MRI.

44. The method of claim 43, wherein said information is used to generate a three-dimensional representation of cartilage thickness or a physical model of said normal or said diseased tissue or both.

45. The method of claim 44, wherein said physical model is used to shape a tissue transplant, a tissue graft, a tissue implant, a tissue replacement material, a tissue scaffold or a tissue regenerating material or tissue repair system.

46. The method of claim 31, wherein said electronic data provides information on the thickness, shape, or curvature of said normal and said diseased tissue or the location and size of said diseased tissue.

47. A method of treating a human joint disease involving cartilage comprising:

obtaining electronic image data of a joint, wherein said image data includes both normal and diseased cartilage tissue;

electronically evaluating in three dimensions said image data to obtain information about volume, area, thickness, curvature, water content, sodium content, hyaluronic acid content, glycosaminoglycan content, signal intensity or relaxation time of said normal or diseased tissue, or three dimensional geometry of the joint, said electronically evaluating including evaluating said image data along one or more vectors tangent or perpendicular to the cartilage or bone surface; and selecting or designing a therapy based on said three dimensional evaluation.

48. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating further including:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times; and selecting a therapy based on said three-dimensional evaluation.

49. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating further including:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value time the area of the cartilage defect, $A_D$, to give the volume of cartilage loss; and selecting a therapy based on said three-dimensional evaluation.

50. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating further including:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times; and selecting a therapy based on said three-dimensional evaluation.

51. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating further including:

providing a biochemically based representation of joint cartilage of a mammal, wherein the joint comprises cartilage and associated bones on either side of the joint, which method comprises, measuring a detectable biochemical component in the cartilage, determining the relative amounts of the biochemical component in the cartilage, evaluating the amounts of the biochemical component in three dimensions in the cartilage, and determining the areas of abnormally joint cartilage by identifying the areas having altered amounts of the biochemical component present; and selecting a therapy based on said three-dimensional evaluation.

52. A method of treating a human joint disease involving cartilage comprising:

obtaining electronic image data of a joint, wherein said image data includes both normal and diseased cartilage tissue;

electronically evaluating in three dimensions said image data to obtain information about geometry of the joint, said electronically evaluating further including:

estimating the change of cartilage in a joint, wherein the joint comprises articular cartilage, which method comprises, defining a 3D object coordinate system of the joint at an initial time, T1, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$; and selecting a therapy based on said three-dimensional evaluation.

53. A method of treating a human joint disease involving cartilage comprising:

obtaining electronic image data of a joint, wherein said image data includes both normal and diseased cartilage tissue;

electronically evaluating in three dimensions said image to obtain information about geometry of the joint, said electronically evaluating further including:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data; and selecting a therapy based on said three-dimensional evaluation.

54. A method of treating a human joint disease involving cartilage comprising:

obtaining electronic data associated with an image of a joint, wherein said image data includes both normal and diseased cartilage tissue;

electronically evaluating in three-dimensions said image data to obtain information about geometry of the joint, said electronically evaluating including evaluating cartilage or bone in said image along at least three vectors, at least one of the vectors being non-coplanar and non-parallel with at least two of the other vectors defining a vector plane; and selecting or designing a therapy based on said three-dimensional evaluation.

55. The method of claim 54, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

56. The method of claim 54, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

57. The method of claim 54, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_L$ to give the thickness of the cartilage loss, $D_L$, and multiplying the $D_L$ value times the area of the cartilage defect, $A_D$, to give the volume of cartilage loss.

58. The method of claim 54, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

59. The method of claim 54, wherein said electronically evaluating further comprises:

providing a biochemically based representation of joint cartilage of a mammal, wherein the joint comprises cartilage and associated bones on either side of the joint, which method comprises, measuring a detectable biochemical component in the cartilage, determining the relative amounts of the biochemical component in the cartilage, evaluating the amounts of the biochemical component in three dimensions in the cartilage, and determining the areas of abnormal joint cartilage by identifying the areas having altered amounts of the biochemical component present.

60. The method of claim 54, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

61. A method of claim 54, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

62. The method of claim 54, wherein said electronic image provides information on the thickness, shape, or curvature of said normal and said diseased tissue or the location and size of said diseased tissue.

63. The method of claim 54, wherein said therapy comprises autologous chondrocyte transplantation, osteochondral allografting, osteochondral autografting, an implant, a replacement material, a scaffold, a regenerating material and a repair system, tibial corticotomy, femoral or tibial osteotomy.

64. The method of claim 54, wherein said therapy uses cartilage or bone tissue grown ex vivo, stem cells, an artificial non-human material, an agent that stimulates repair of said diseased tissue, or an agent.

65. The method of claim 54, wherein said information is used to determine the thickness or other geometrical feature of a tissue transplant, a tissue graft, a tissue implant, a tissue replacement material, a tissue scaffold, or a tissue regenerating material or tissue repair system.

66. The method of claim 54, wherein said image is obtained using ultrasound, computed tomography, positron emission tomography, a single photon emission computed tomography scan, or MRI.

67. The method of claim 66, wherein said information is used to generate a three-dimensional representation of cartilage thickness or a physical model of said normal or said diseased tissue or both.

68. The method of claim 67, wherein said physical model is used to shape a tissue transplant, a tissue graft, a tissue implant, a tissue replacement material, a tissue scaffold or a tissue regenerating material or tissue repair system.

69. A method of treating a human joint disease involving cartilage comprising:

obtaining electronic image data of a joint, wherein said image data includes both normal and diseased cartilage tissue;

electronically evaluating in three dimensions cartilage or bone in said image data to obtain information about geometry of the joint at a first point and a second point, wherein information related to the first point is derived based on at least one point of the joint that forms, with the first point, a first vector, wherein information related to the second point is derived based on at least one point of the joint that forms, with the second point, a second vector, and wherein the first and second vectors are non-coplanar and non-parallel; and selecting or designing a therapy based on said three-dimensional evaluation.

70. The method of claim 69, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

71. The method of claim 69, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

72. The method of claim 69, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

73. The method of claim 69, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

74. The method of claim 69, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the areas having altered amounts of the biochemical component present.

75. The method of claim 69, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

76. A method of claim 69, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

77. The method of claim 69, wherein said electronic image data provides information on the thickness, shape, or curvature of said normal and said diseased tissue or the location and size of said diseased tissue.

78. The method of claim 69, wherein said therapy comprises autologous chondrocyte transplantation, osteochondral allografting, osteochondral autografting, an implant, a replacement material, a scaffold, a regenerating material and a repair system, tibial corticotomy, femoral or tibial osteotomy.

79. The method of claim 69, wherein said therapy uses cartilage or bone tissue grown ex vivo, stem cells, an artificial non-human material, an agent that stimulates repair of said diseased tissue, or an agent.

80. The method of claim 69, wherein said information is used to determine the thickness or other geometrical feature of a tissue transplant, a tissue graft, a tissue implant, a tissue replacement material, a tissue scaffold, or a tissue regenerating material or tissue repair system.

81. The method of claim 69, wherein said image is obtained using ultrasound, computed tomography, positron emission tomography, a single photon emission computed tomography scan, or MRI.

82. The method of claim 81, wherein said information is used to generate a three-dimensional representation of cartilage thickness or a physical model of said normal or said diseased tissue or both.

83. The method of claim 82, wherein said physical model is used to shape a tissue transplant, a tissue graft, a tissue implant, a tissue replacement material, a tissue scaffold or a tissue regenerating material or tissue repair system.

84. A method of treating a human joint disease involving cartilage comprising:

imaging a joint on an imaging plane to obtain electronic image data, the image data including both normal and diseased cartilage tissue;

electronically evaluating in three dimensions said image data to obtain information about geometry of the joint, said electronically evaluating including evaluating cartilage or bone in said image along a vector that is non-parallel to the imaging plane; and selecting or designing a therapy based on said three-dimensional evaluation.

85. The method of claim 84, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional vlume of a region of degenerated cartilage evaluated at the later time, and determining the loss in thickness or regional volume of the region of degenerated cartilage between the later and initial times.

86. The method of claim 84, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferring image at the distant location, converting the transferred image to a degeneration pattern of the cartilage, and transmitting the degeneration pattern to a site for analysis.

87. The method of claim 84, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

88. The method of claim 84, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

89. The method of claim 84, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the area having altered amounts of the biochemical component present.

90. A method of claim 84, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

91. A method of claim 84, wherein said electronically evaluating further comprises:

correlating cartilage image data, bone image data, and optoelectrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

92. The method of claim 84, wherein said electronic image data provide information on the thickness, shape, or curvature of said normal and said diseased tissue or the location and size of said diseased tissue.

93. The method of claim 84, wherein said therapy comprises autologous chondrocyte transplantation, osteochondral allografting, osteochondral autografting, an implant, a replacement material, a scaffold, a regenerating material, a repair system, tibial corticotomy, femoral osteotomy or tibial osteotomy.

94. The method of claim 84, wherein said therapy uses cartilage or bone tissue grown ex vivo, stem cells, an artificial non-human material, an agent that stimulates repair of said diseased tissue, or an agent.

95. The method of claim 84, wherein said information is used to determine the thickness or other geometrical feature of a tissue transplant, a tissue graft, a tissue implant, a tissue replacement material, a tissue scaffold, or a tissue regenerating material or tissue repair system.

96. The method of claim 84, wherein said image is obtained using ultrasound, computed tomography, positron emission tomography, a single photon emission computed tomography scan, or MRI.

97. The method of claim 96, wherein said information is used to generate a three-dimensional representation of cartilage thickness or a physical model of said normal or said diseased tissue or both.

98. The method of claim 97, wherein said physical model is used to shape a tissue transplant, a tissue graft, a tissue implant, a tissue replacement material, a tissue scaffold or a tissue regenerating material or tissue repair system.

99. A method of treating a human joint disease involving cartilage comprising:

obtaining CT or MRI image data of a joint, wherein said image data includes both normal and diseased cartilage tissue;

electronically evaluating in three dimensions said image data to obtain information about geometry of the joint, said electronically evaluating including evaluating the joint along at least two non-parallel planes; and selecting a therapy based on said three-dimensional evaluation.

100. The method of claim 99, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

101. The method of claim 99, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

102. The method of claim 99, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

103. The method of claim 99, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

104. The method of claim 99, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the areas having altered amounts of the biochemical component present.

105. The method of claim 99, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, placing the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

106. The method of claim 99, wherein said electronically evaluating further comprises:

correlating cartilage image data, bone image data, and optoelctrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

107. The method of claim 99, wherein said electronic image data provides information on the thickness, shape, or curvature of said normal and said diseased tissue or the location and size of said diseased tissue.

108. The method of claim 99, wherein said therapy comprises autologous chondrocyte transplantation, osteochondral allografting, osteochondral autografting, an implant, a replacement material, a scaffold, a regenerating material, a repair system, tibial corticotomy, femoral osteotomy or tibial osteotomy.

109. The method of claim 99, wherein said therapy uses cartilage or bone tissue grown ex vivo, stem cells, an artificial non-human material, an agent that stimulates repair of said diseased tissue, or an agent.

110. The method of claim 99, wherein said information is used to determine the thickness or other geometrical feature of a tissue transplant, a tissue graft, a tissue implant, a tissue replacement material, a tissue scaffold, or a tissue regenerating material or tissue repair system.

111. The method of claim 99, wherein said information is used to generate a three-dimensional representation of cartilage thickness or a physical model of said normal or said diseased tissue or both.

112. The method of claim 111, wherein said physical model is used to shape a tissue transplant, a tissue graft, a tissue implant, a tissue replacement material, a tissue scaffold or a tissue regenerating material or tissue repair system.

113. A method of treating a human joint disease involving cartilage comprising:

obtaining CT or MRI image data of a joint, wherein said image data includes both normal and diseased cartilage tissue;

electronically evaluating in three dimensions said image data to obtain information about geometry of the joint, said electronically evaluating including evaluating said joint along at least two non-parallel planes; and determining at least one of size and shape for at least one of a transplant, a graft, an implant, a replacement material, a scaffold, a regenerating material and a repair system based on said three dimensional evaluation.

114. The method of claim 113, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

115. The method of claim 113, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

116. The method of claim 113, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

117. The method of claim 113, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

118. The method of claim 113, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the areas having altered amounts of the biochemical component present.

119. The method of claim 113, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, identifying the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

120. The method of claim 113, wherein said electronically evaluating further comprises:

correlating cartilage image data, bone image data, and optoelctrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

121. The method of claim 113, wherein said electronic image provides information on the thickness, shape, or curvature of said normal and said diseased tissue or the location and size of said diseased tissue.

122. The method of claim 113, wherein said articular repair comprises autologous chondrocyte transplantation, osteochondral allografting, osteochondral autografting, tibial corticotomy, femoral or tibial osteotomy.

123. The method of claim 113, wherein said articular repair uses cartilage or bone tissue grown ex vivo, stem cells, an artificial non-human material, an agent that stimulates repair of said diseased tissue, or an agent.

124. The method of claim 113, wherein said information is used to determine the thickness or other geometrical feature of a tissue transplant, a tissue graft, a tissue implant, a tissue replacement material, a tissue scaffold, or a tissue regenerating material or tissue repair system.

125. The method of claim 113, wherein said information is used to generate a three-dimensional representation of cartilage thickness or a physical model of said normal or said diseased tissue or both.

126. The method of claim 125, wherein said physical model is used to shape a tissue transplant, a tissue graft, a tissue implant, a tissue replacement material, a tissue scaffold or a tissue regenerating material or tissue repair system.

127. A method of treating a human joint disease involving cartilage comprising:

obtaining CT or MRI image data of a joint, wherein said image data includes both normal and diseased cartilage tissue;

electronically evaluating in three dimensions said image data to obtain information about geometry of the joint, said electronically evaluating including evaluating said joint along at least two non-parallel planes; and designing a therapy based on said three dimensional evaluation.

128. The method of claim 127, wherein said electronically evaluating further comprises:

estimating the loss of cartilage in a joint, wherein the joint comprises cartilage and accompanying bones on either side of the joint, which method comprises, obtaining a three-dimensional representation of the cartilage at an initial time and calculating the thickness or regional volume of a region of degenerated cartilage evaluated at the initial time, obtaining a three-dimensional representation of the cartilage at a later time, calculating the thickness or regional volume of a region of degenerated cartilage evaluated at the later time, and determining the loss in thickness or regional volume of the region of degenerated cartilage between the later and initial times.

129. The method of claim 127, wherein said electronically evaluating further comprises:

assessing the condition of cartilage in a joint of a human, which method comprises, electronically transferring an electronically generated image of a cartilage of the joint from a transferring device to a receiving device located distant from the transferring device, receiving the transferred image at the distant location, converting the transferred image to a degeneration pattern of the cartilage, and transmitting the degeneration pattern to a site for analysis.

130. The method of claim 127, wherein said electronically evaluating further comprises:

determining the volume of cartilage loss in a region of a cartilage defect of a cartilage in a joint of a mammal which method comprises, determining the thickness, $D_N$, of the normal cartilage near the cartilage defect, obtaining the thickness of the cartilage defect, $D_D$, of the region, subtracting $D_D$ from $D_N$ to give the thickness of the cartilage loss, $D_L$, and multiplying the $D_L$ value times the area of the cartilage defect, $A_D$, to give the volume of cartilage loss.

131. The method of claim 127, wherein said electronically evaluating further comprises:

estimating the change of cartilage in a joint of a mammal over time, which method comprises, estimating the thickness or width or area or volume of a region of cartilage at an initial time $T_1$, estimating the thickness or width or area or volume of the region of cartilage at a later time $T_2$, and determining the change in the thickness or width or area or volume of the region of cartilage between the initial and the later times.

132. The method of claim 127, wherein said electronically evaluating further comprises:

providing a biochemically based representation of joint cartilage of a mammal, wherein the joint comprises cartilage and associated bones on either side of the joint, which method comprises, measuring a detectable biochemical component throughout the cartilage, determining the relative amounts of the biochemical component throughout the cartilage, evaluating the amounts of the biochemical component in three dimensions through the cartilage, and determining the areas of abnormally joint cartilage by identifying the areas having altered amounts of the biochemical component present.

133. The method of claim 127, wherein said electronically evaluating further comprises:

estimating the change of cartilage in a joint, wherein the joint comprises articular cartilage, which method comprises, defining a 3D object coordinate system of the joint at an initial time, $T_1$, identifying a region of a cartilage defect within the 3D object coordinate system, defining a volume of interest around the region of the cartilage defect whereby the volume of interest is larger than the region of cartilage defect, but does not encompass the entire articular cartilage, defining the 3D object coordinate system of the joint at a second timepoint, $T_2$, identifying the identically-sized volume of interest into the 3D object coordinate system at timepoint $T_2$ using the object coordinates of the volume of interest at timepoint $T_1$, and measuring any differences in cartilage volume within the volume of interest between timepoints $T_1$ and $T_2$.

134. The method of claim 127, wherein said electronically evaluating further comprises:

correlating cartilage image data, bone image data, and optoelctrical image data for the assessment of the condition of a joint, which method comprises, (a) obtaining the cartilage image data of the joint with a set of skin reference markers placed externally near the joint, (b) obtaining the bone image data of the joint with a set of skin reference markers positioned in the same manner as the markers in (a), (c) obtaining the optoelectrical image data of the joint with a set of skin reference markers positioned in the same manner as (a) and (b), and (d) using the skin reference markers to correlate the images obtained in (a), (b) and (c) with each other, wherein each skin reference marker is detectable in the cartilage and bone data and the opto-electrical data.

135. The method of claim 127, wherein said therapy comprises autologous chondrocyte transplantation, osteochondral allografting, osteochondral autografting, an implant, a replacement material, a scaffold, a regenerating material, a repair system, tibial corticotomy, femoral osteotomy or tibial osteotomy.

136. The method of claim 127, wherein said therapy uses cartilage or bone tissue grown ex vivo, stem cells, an artificial non-human material, an agent that stimulates repair of said diseased tissue, or an agent.

137. The method of claim 127, wherein said information is used to determine the thickness or other geometrical feature of a tissue transplant, a tissue graft, a tissue implant, a tissue replacement material, a tissue scaffold, or a tissue regenerating material or tissue repair system.

138. The method of claim 127, wherein said information is used to generate a three-dimensional representation of cartilage thickness or a physical model of said normal or said diseased tissue or both.

139. The method of claim 138, wherein said physical model is used to shape a tissue transplant, a tissue graft, a tissue implant, a tissue replacement material, a tissue scaffold or a tissue regenerating material or tissue repair system.

140. A method of treating a human joint disease involving cartilage comprising:

obtaining CT or MRI image data of a joint, wherein said image data includes both normal and diseased cartilage tissue;

electronically evaluating in three dimensions said image data to obtain information about volume, area, thickness, curvature, water content, sodium content, hyaluronic acid content, glycosaminoglycan content, signal intensity or relaxation time of said normal or diseased tissue, or three dimensional geometry of the joint, said electronically evaluating including evaluating said joint along at least two non-parallel planes; and selecting or designing a therapy based on said three dimensional evaluation.

* * * * *

UNITED STATES PATENT AND TRADEMARK OFFICE

CERTIFICATE OF CORRECTION

PATENT NO. : RE43,282 E
APPLICATION NO. : 12/193907
DATED : March 27, 2012
INVENTOR(S) : Alexander et al.

It is certified that error appears in the above-identified patent and that said Letters Patent is hereby corrected as shown below:

In column 51, line 4
replace “an later”
with “a later”

In column 56, line 35
replace “mehtod”
with “method”

In column 64, line 26
replace “vlume”
with “volume”

Signed and Sealed this
Thirtieth Day of October, 2012

David J. Kappos

David J. Kappos
*Director of the United States Patent and Trademark Office*